(12) United States Patent
Schwarz et al.

(10) Patent No.: US 9,018,358 B2
(45) Date of Patent: Apr. 28, 2015

(54) DC-STAMP ANTIBODIES

(75) Inventors: Edward M. Schwarz, Rochester, NY (US); Kofi A. Mensah, Queens Village, NY (US); Yahui Grace Chiu, Pittsford, NY (US); Christopher T. Ritchlin, Canandaigua, NY (US)

(73) Assignee: University of Rochester, Rochester, NY (US)

(*) Notice: Subject to any disclaimer, the term of this patent is extended or adjusted under 35 U.S.C. 154(b) by 512 days.

(21) Appl. No.: 13/266,629

(22) PCT Filed: Apr. 29, 2010

(86) PCT No.: PCT/US2010/033057
§ 371 (c)(1),
(2), (4) Date: Dec. 27, 2011

(87) PCT Pub. No.: WO2010/127180
PCT Pub. Date: Nov. 4, 2010

(65) Prior Publication Data
US 2013/0209471 A1    Aug. 15, 2013

Related U.S. Application Data

(60) Provisional application No. 61/174,219, filed on Apr. 30, 2009.

(51) Int. Cl.
*C07K 16/00* (2006.01)
*C12P 21/08* (2006.01)
*C07K 16/28* (2006.01)
*C07K 14/705* (2006.01)

(52) U.S. Cl.
CPC ............ *C07K 16/28* (2013.01); *C07K 14/705* (2013.01); *C07K 2316/96* (2013.01); *C07K 2317/34* (2013.01)

(58) Field of Classification Search
None
See application file for complete search history.

(56) References Cited

U.S. PATENT DOCUMENTS

| | | |
|---|---|---|
| 2005/0142587 A1 | 6/2005 | Zlot et al. |
| 2007/0031421 A1 | 2/2007 | Nomiyama et al. |
| 2007/0081974 A1 | 4/2007 | Nomiyama et al. |
| 2007/0191279 A1 | 8/2007 | Cronstein et al. |

FOREIGN PATENT DOCUMENTS

JP     2005255674     9/2005

OTHER PUBLICATIONS

Klimka et al., 2000, British J. Cancer. vol. 83: 252-260.*
Dryberg et al., 1986, J. Exp. Med. vol. 164: 1344-49.*
Sawatani et al., "The role of DC-STAMP in maintenance of immune tolerance through regulation of dendritic cell function," Int. Immunol. 20:1259-68 (2008).
Schwarz et al., "Autoimmunity and bone," Ann. NY Acad. Sci. 1068:275-83 (2006).
Staege et al., "Two novel genes FIND and LIND differentially expressed in deactivated and *Listeria*-infected human macrophages," Immunogenetics 53:105-13 (2001).
Sunderkotter et al., "Subpopulations of mouse blood monocytes differ in maturation stage and inflammatory response," J. Immunol. 172:4410-7 (2004).
Takayanagi et al., "RANKL maintains bone homestasis through c-Fos-dependent induction of interferon-b," Nature 416:744-9 (2002).
Takeshita et al., "Identification and characterization of the new osteoclast progenitor with macrophage phenotypes being able to differentiate into mature osteoclasts," J. Bone Miner. Res. 15:1477-88 (2000).
Teitelbaum, "Bone resportion by osteoclasts," Science 289:1504-8 (2000).
Valleala et al., "Two year-randomized controlled trial of etidronate in rheumatoid arthritis: changes in serum aminoterminal telopeptides correlate with radiographic progression of disease," J. Rheumatol. 30:468-73 (2003).
Vandooren et al., "In vitro spontaneous osteoclastogenesis of human peripheral blood mononuclear cells is not crucially dependent on T lymphocytes," Arthritis Rheum. 60:1020-5 (2009).
Vignery et al., "Macrophage fusion: the making of osteoclasts and giant cells," J. Exp. Med. 202:337-40 (2005).
Yagi et al., "DC-STAMP is essential for cell-cell fusion in osteoclasts and foreign body giant cells," J. Exp. Med. 202:345-51 (2005).
Yagi et al., "Role of DC-STAMP in cellular fusion of osteoclasts and macrophage giant cells," J. Bone Miner. Metab. 24:355-8 (2006).
Yagi et al., "Induction of DC-STAMP by alternative activation and downstream signaling mechanisms," J. Bone Miner. Res. 22:992-1001 (2007).
Yang et al., "Osteoclast stimulatory transmembrane protein (OC-STAMP), a novel protein induced by RANKL that promotes osteoclast differentiation," J. Cell Physiol. 215:497-505 (2008).
Yao et al., "Tumor necrosis factor alpha increases circulating osteoclast precursor numbers by promoting their proliferation and differentiation in the bone marrow through upregulation of c-fms expression," J. Biol. Chem. 281:11846-55 (2006).
Chiu et al., "Regulation of human osteoclast development by dendritic cell-specific transmembrane protein (DC-STAMP)," J. Bone Mineral Res. 27(1):79-92 (2011).
Mensah et al., "Mediation of nonerosive arthritis in a mouse model of lupus by interferon-a-stimulated monocyte differentiation that is nonpermissive of osteoclastogenesis," Arthritis Rheum. 62(4):1127-37 (2010).

(Continued)

*Primary Examiner* — Amy Juedes
(74) *Attorney, Agent, or Firm* — Kilpatrick Townsend & Stockton, LLP

(57) ABSTRACT

Provided herein are antibodies that specifically bind an epitope of DC-STAMP. Specifically, provided herein are monoclonal antibodies that bind an epitope of DC-STAMP, wherein the epitope comprises the amino acid sequence Glu-Val-His-Leu-Lys-Leu-His-Gly-Glu-Lys-Gln-Gly-Thr-Gln (SEQ ID NO:1). Optionally, the epitope comprises the amino acid sequence His-Gly-Glu-Lys-Gln-Gly-Thr-Gln (SEQ ID NO:2). Optionally, the epitope comprises the amino acid sequence Lys-Gln-Gly-Thr-Gln (SEQ ID NO:3).

15 Claims, 28 Drawing Sheets

(56) References Cited

OTHER PUBLICATIONS

European Patent Application No. 10770383.7, Communication Pursuant to Article 94(3) EPC, mailed Sep. 30, 2013, 6 pages.
Adachi et al., "Marked increase in number of dendritic cells in autoimmune-prone (NZW X BXSB) F1 mice with age," Stem Cells 20:61-72 (2002).
Anandarajah et al., "The effect of etanercept on osteoclast precursor frequency and enhancing bone marrow cedema in patients with psioratic arthritis," Ann. Rheum. Dis. 67:296-301 (2008).
Boyle et al., "Osteoclast differentiation and activation," Nature 423:337-42 (2003).
Chen et al., "Cell-cell fusion," FEBS Lett. 581:2181-93 (2007).
Chiu et al., "Dendritic Cell-Specific Transmembrane Protein (DC-STAMP) is a Biomarker for Osteoclast Precursors in Psoriatic Arthritis," Arthritis Rheum. 58:S945. Presented by G. Chiu at the American College of Rheumatology Scientific Meeting, San Francisco, CA (Abstract) (Oct. 24-29, 2008).
Chiu et al., "CD16 (FcRgammaIII) as a potential marker of osteoclast precursors in psoriatic arthritis," Arthritis Res. Ther. 12:R14 (2010).
Dalbeth et al., "Enhanced osteoclastogenesis in patients with tophaceous gout: urate crystals promote osteoclast development through interactions with stromal cells," Arthritis Rheum. 58:1854-65 (2008).
De Vries et al., "Effect of CD44 deficiency on in vitro and in vivo osteoclast formation," J. Cell Biochem. 94:954-66 (2005).
Eleveld-Trancikova et al., "The DC-derived protein DC-STAMP influences differentiation of myeloid cells," Leukemia 22:455-9 (2008).
Eleveld-Trancikova et al., "The dendritic cell-derived protein DC-STAMP is highly conserved and localizes to the endoplasmic reticulum," J. Leukoc. Biol. 77:337-43 (2005).
Eswarakumar et al., "RT-PCR cloning and characterization of mouse immunoglobulin variable domains with high affinity for HLA-DR antigens," Immunogenetics 46:249-50 (1997).
Flick et al., "Effects of receptor activator of NFkB (RANK) signaling blockade on fracture healing," J. Orthop. Res. 21:676-84 (2003).
Hartgers et al., "DC-STAMP, a novel multimembrane-spanning molecule preferentially expressed by dendritic cells," Eur. J. Immunol. 30:3585-90 (2000).
Hayashi et al., "Regulation of receptor activator of NF-kappa B ligand-induced osteoclastogenesis by endogenous interferon-beta (INF-beta) and suppressors of cytokine signaling (SOCS). The possible counteracting role of SOCs-in IFNbeta inhibited osteoclast formation," J. Biol. Chem. 277:27880-6 (2002).
Hayer et al., "CD44 is a determinant of inflammatory bone loss," J. Exp. Med. 201:903-14 (2005).
Heinemann et al., "Alkaline phosphatase expression during monocyte differentiation. Overlapping markers as a link between monocytic cells, dendritic cells, osteoclasts and osteoblasts," Immunobiol. 202:68-81 (2000).
Helming et al., "Essential role of DAP12 signaling in macrophage programming into a fusion-competent state," Sci. Signal 1:ra11 (2008).
Hua et al., "Functional assay of type I interferon in systemic lupus erythematosus plasma and association with anti-RNA binding protein autoantibodies," Arthritis Rheum. 54:1906-16 (2006).
Huang et al., "Exposure to receptor-activator of NFkB ligand renders pre-osteoclasts resistant to IFN-gamma by inducing terminal differentiation," Arthritis Res. Ther. 5:R49-59 (2003).
Ishii et al., "RANKL-induced expression of tetraspanin CD9 in lipid raft membrane microdomain is essential for cell fusion during osteoclastogenesis," J. Bone Miner. Res. 21:965-76 (2006).
Iwaski et al., "Cell fusion in osteoclasts plays a critical role in controlling bone mass and osteoblastic activity," Biochem. Biophys. Res. Commun. 377:899-904 (2008).
Jacquin et al., "Identification of multiple osteoclast precursor populations in murine bone marrow," J. Bone Min. Res. 21:67-77 (2006).
Jansen et al., "OS9 interacts with DC-STAMP and modulates its intracellular localization in response to TLR ligation," Mol. Immunol. 46:505-15 (2009).
Jarrett et al., "Preliminary evidence for a structural benefit of the new bisphosphonate zoledronic acid in early rheumatoid arthritis," Arthritis Rheum. 54:1410-4 (2006).
Jarrin and Andrieux, "Sequencing of antibodies," Methods Mol. Biol. 96:21-8 (1999).
Keffer et al., "Transgenic mice expressing human tumour necrosis factor: a predictive genetic model of arthritis," EMBO J. 10:4025-31 (1991).
Kouskoff et al., "Organ-specific disease provoked by systemic autoimmunity," Cell 87:811-22 (1996).
Kukita et al., "RANKL-induced DC-STAMP is essential for osteoclastogenesis," J. Exp. Med. 200:941-6 (2004).
Li et al., "Systemic tumor necrosis factor alpha mediates an increase in peripheral CD IIbhigh osteoclast precursors in tumor necrosis factor alpha-transgenic mice," Arthritis Rheum. 50:265-76 (2004).
Lisenbee et al., "Overexpression and mislocalization of a tail-anchored GFP redefines the identity of peroxisomal ER," Traffic 4:491-501 (2003).
Lundberg et al., "Osteoclast formation is strongly reduced both in vivo and in vitro in the absence of CD47/SIRPalpha-interaction," Biochem. Biophys. Res. Commun. 352:444-8 (2007).
Mathian et al., "IFNalpha induces early lethal lupus in preautoimmune (New Zealand Black x New Zealand White) F1 but not in BALB/c mice," J. Immunol. 174:2499-506 (2005).
Mensah et al., "DC-STAMP as a surface marker of erosive vs. non-erosive arthritis," Arthritis Rheum. 59:S107 Presented at the Americal College of Rheumatology Scientific Meeting, Boston, MA (Abstract) (Nov. 6-11, 2007).
Mensah et al., "Differential Expression of Fusion-related genes correlates with the osteoclastogenic potential of DC-STAMPlo vs. DC-STAMPhi precursors," Arthritis Rheum. 58:S646 Presented at American College of Rheumatology Scientific Meeting, San Fran., CA (Abstract) (Oct. 24-29, 2008).
Mensah et al., "IFN-a Effects on Expression of Fusion-Related Molecules in Osteoclast Precursors: Insights into Non-Erosive SLE Arthropathy," Arthritis Rheum. 58:S668. Presented at the American College of Rheumatology Scientific Meeting, San Fran., CA (Abstract) (Oct. 24-29, 2008).
Mensah et al., "Altered bone remodeling in psoriatic arthritis," Curr. Rheumatol. Rep. 10(4):311-7 (2008).
Mensah et al., "RANKL induces heterogeneous DC-STAMPlo and DC-STAMPhi osteoclast precursors of which the DC-STAMPlo precursors are the master fusogens," J. Cell Physiol. 223:76-83 (2009).
Metlay et al., "The distinct leukocyte integrins of mouse spleen dendritic cells as identified with new hamster monoclonal antibodies," J. Exp. Med. 171:1753-71 (1990).
Milligan, "G protein-coupled receptor dimerization: function and ligand pharmacology," Mol. Pharmacol. 66:1-7 (2004).
Morrison, Curr. Protoc. Immunol. Chap. 10, Unit 10.25 (2001).
Nimmerjahn and Ravetch, "FC-gamma receptors as regulators of immune responses," Nat. Rev. Immunol. 8:34-47 (2008).
Nose et al., "Comparison of osteoclast precursors in peripheral blood mononuclear cells from rheumatoid arthritis and osteoporosis patients," J. Bone Miner. Metab. 27:57-65 (2009).
Proulx et al., "Longitudinal assessment of synovial, lymph node, and bone volumes in inflammatory arthritis in mice by in vivo magnetic resonance imaging and microfocal computed tomography," Arthritis Rheum. 56:4024-37 (2007).
Ralston et al., "Clinical, biochemical, and radiographic effects of aminohydroxypropylidene bisphosphonate treatment in rheumatoid arthritis," Ann. Rheum. Dis. 48:396-9 (1989).
Rivollier et al., "Immature dendritic cell transdifferentiation into osteoclasts: a novel pathway sustained by the rheumatoid arthritis microenvironment," Blood 104:4029-37 (2004).
Rozzo et al., "Evidence for an interferon-inducible gene, Ifi2002, in the susceptibility to systemic lupus," Immunity 15:435-43 (2001).
Sandor et al., "Developmentally regulated Fcgamma expression in lymphopoiesis Fcgamma receptor III (CD16) provides an ITAM motif for pro-T and pro-B cells," Immunol. Lett. 54:123-7 (1996).
Santiago-Raber et al., "Type-I interferon receptor deficiency reduces lupus-like disease in NZB mice," J. Exp. Med. 197:777-88 (2003).

(56) References Cited

OTHER PUBLICATIONS

Santini et al., "Type I Interferon as a powerful adjuvant for monocyte-derived dendritic cell development and activity in vitro and in Hu-Pbl-Scid mice," J. Exp. Med. 191:1777-88 (2000).

Sato et al., "Th17 functions as an osteoclastogenic helper T cell subset that links T cell activation and bone destruction," J. Exp. Med. 203:2673-82 (2006).

European Patent Application No. 10770383.7, Extended European Search Report, mailed Nov. 21, 2012, 8 pages.

Miyamoto et al., "Regulation of 1-15 osteoclastogenesis by ganoderic acid DM isolated from *Ganoderma lucidum*", European Journal of Pharmacology, vol. 602, No. 1, Jan. 5, 2009, pp. 1-7.

International Search Report and Written Opinion for PCT/US2010/033057, mailed Jan. 13, 2011.

International Preliminary Report on Patentability for PCT/US2010/033057, mailed Nov. 10, 2011.

European Patent Application No. 10770383.7, Invitation pursuant to Article 94(3) and Rule 71(1) EPC, mailed Dec. 3, 2014, 3 pages.

* cited by examiner

| Gene | DC-STAMP[lo] | DC-STAMP[hi] |
|---|---|---|
| trap | 1.41 | 0.67 |
| cd9 | 0.60 | 0.48 |
| cd44 | 1.38 | 0.60 |
| cd47 | 0.05 | 2.97 |
| sirpα | 17.73 | 4.90 |

| DC-STAMP pattern | I | II | III | IV |
|---|---|---|---|---|
| # of subjects | | | | |
| healthy control | 11 | 0 | 0 | 0 |
| PsA patients | 4 | 6 | 5 | 6 |
| OC# (per 10⁵ PBMC) | | | | |
| median | 50 | 98 | 105 | 203 |
| inter-quartile range | 17 - 105 | 21 - 390 | 62 - 131 | 35 - 340 |
Figure 17B
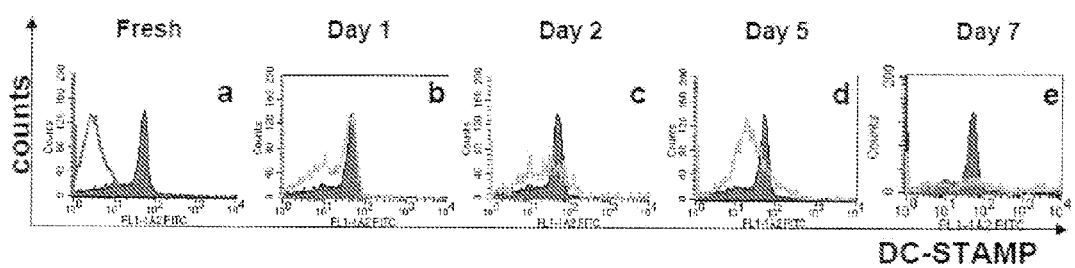
Figure 18A
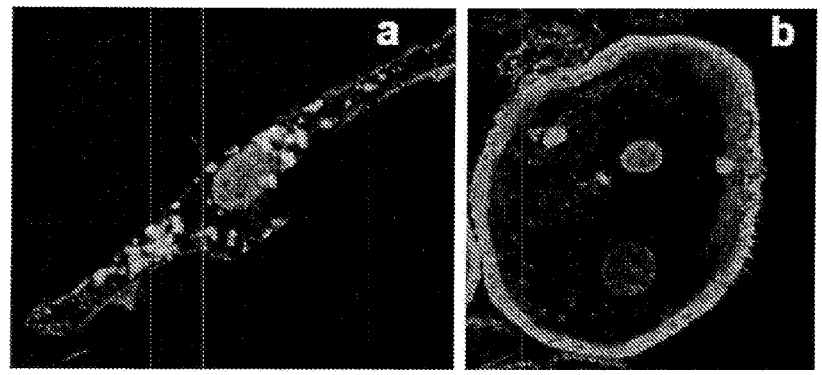
Figure 18B

SEQUENCE LISTING

<160> NUMBER OF SEQ ID NOS: 8

<210> SEQ ID NO 1
<211> LENGTH: 14
<212> TYPE: PRT
<213> ORGANISM: Artificial Sequence
<220> FEATURE:
<223> OTHER INFORMATION: Synthetic construct

<400> SEQUENCE: 1

Glu Val His Leu Lys Leu His Gly Glu Lys Gln Gly Thr Gln
1               5                   10

<210> SEQ ID NO 2
<211> LENGTH: 8
<212> TYPE: PRT
<213> ORGANISM: Artificial sequence
<220> FEATURE:
<223> OTHER INFORMATION: Synthetic construct

<400> SEQUENCE: 2

His Gly Glu Lys Gln Gly Thr Gln
1               5

<210> SEQ ID NO 3
<211> LENGTH: 5
<212> TYPE: PRT
<213> ORGANISM: Artificial sequence
<220> FEATURE:
<223> OTHER INFORMATION: Synthetic construct

<400> SEQUENCE: 3

Lys Gln Gly Thr Gln
1               5

<210> SEQ ID NO 4
<211> LENGTH: 6
<212> TYPE: PRT
<213> ORGANISM: Artificial sequence
<220> FEATURE:
<223> OTHER INFORMATION: Synthetic construct

<400> SEQUENCE: 4

Ser Phe Tyr Pro Ser Val
1               5

<210> SEQ ID NO 5
<211> LENGTH: 134
<212> TYPE: PRT
<213> ORGANISM: Artificial sequence
<220> FEATURE:
<223> OTHER INFORMATION: Synthetic construct

<400> SEQUENCE: 5

Met Arg Phe Ser Ala Gln Leu Leu Gly Leu Leu Val Leu Trp Ile Pro
1               5                   10                  15

Gly Ser Thr Ala Asp Ile Val Met Thr Gln Ala Ala Phe Ser Asn Pro
                20                  25                  30

Val Thr Leu Gly Thr Ser Ala Ser Ile Ser Cys Arg Ser Ser Lys Ser
            35                  40                  45

Leu Leu His Ser Asn Gly Ile Thr Tyr Leu Tyr Trp Tyr Leu Gln Lys
        50                  55                  60

Pro Gly Gln Ser Pro Gln Val Leu Ile Tyr Gln Met Ser Asn Leu Ala
65                  70                  75                  80

```
Ser Gly Val Pro Asp Arg Phe Ser Ser Gly Ser Gly Thr Asp Phe
                85                  90                  95

Thr Leu Arg Ile Ser Arg Val Glu Ala Glu Asp Val Gly Val Tyr Tyr
            100                 105                 110

Cys Ala Gln Asn Leu Glu Leu Pro Trp Thr Phe Gly Gly Gly Thr Lys
        115                 120                 125

Leu Glu Ile Lys Arg Thr
    130
```

<210> SEQ ID NO 6
<211> LENGTH: 138
<212> TYPE: PRT
<213> ORGANISM: Artificial sequence
<220> FEATURE:
<223> OTHER INFORMATION: Synthetic construct

<400> SEQUENCE: 6

```
Met Gly Arg Leu Thr Phe Ser Phe Leu Leu Leu Thr Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Phe Gly Met Gly Val Gly Trp Ile Arg Gln Pro Ser Gly Lys
    50                  55                  60

Gly Leu Glu Trp Leu Ala His Ile Trp Trp Asp Asp Lys Tyr Tyr
65                  70                  75                  80

Ser Pro Ala Leu Lys Ser Arg Leu Thr Ile Ser Lys Asp Thr Ser Lys
                85                  90                  95

Asn Gln Val Phe Leu Lys Ile Ala Asn Val Asp Thr Ala Asp Thr Ala
            100                 105                 110

Thr Tyr Tyr Cys Val Arg Ile Gly Ser Arg Ser Pro Phe Ala Tyr Trp
        115                 120                 125

Gly Pro Gly Thr Leu Val Thr Val Ser Ser
    130                 135
```

<210> SEQ ID NO 7
<211> LENGTH: 402
<212> TYPE: DNA
<213> ORGANISM: Artificial sequence
<220> FEATURE:
<223> OTHER INFORMATION: Synthetic construct

<400> SEQUENCE: 7

```
atgaggttct ctgctcagct tctggggctg cttgtgctct ggatccctgg atccactgca      60
gatattgtga tgacgcaggc tgcattctcc aatccagtca ctcttggaac atcagcttcc     120
atctcctgca ggtctagtaa gagtctccta catagtaatg catcactta tttgtattgg      180
tatctgcaga agccaggcca gtctcctcag gtcctgattt atcagatgtc caaccttgcc     240
tcaggagtcc cagacaggtt cagtagcagt gggtcaggaa ctgatttcac actgagaatc     300
agcagagtgg aggctgagga tgtgggtgtt tattactgtg ctcaaaatct agaacttccg     360
tggacgttcg gtggaggcac caagctggaa ataaaacgta cg                       402
```

<210> SEQ ID NO 8
<211> LENGTH: 414
<212> TYPE: DNA
<213> ORGANISM: Artificial sequence
<220> FEATURE:

<223> OTHER INFORMATION: Synthetic construct

<400> SEQUENCE: 8

```
atgggcagac ttacattctc attcctgtta ctgactgtcc ctgcatatgt cctgtcccag      60
gttactctga aagagtctgg ccctgggata ttgcagccct cccagaccct cagtctgact     120
tgttctttct ctgggttttc actgagcact tttggtatgg gtgtaggctg gattcgtcag     180
ccttcaggga agggtctgga gtggctggca cacatttggt gggatgatga taagtactat     240
agtccagccc tgaagagtcg gctcacaatc tccaaggata cctccaaaaa ccaggtattc     300
ctcaagatcg ccaatgtgga cactgcagat actgccacat actattgtgt tcgaatagga     360
tcacggtccc cttttgctta ctggggccca ggaactctgg tcacagtctc gagt           414
```

DC-STAMP ANTIBODIES

CROSS-REFERENCE TO RELATED APPLICATIONS

This application claims the benefit of U.S. Provisional Application No. 61/174,219, filed on Apr. 30, 2009.

BACKGROUND

Bone is a very dynamic organ as evidenced by the process of bone remodeling which relies on a delicate balance between bone formation and bone resorption and is orchestrated by osteoblasts (OB) and osteoclasts (OC). The coordinated interplay of OB and OC continuously remodels bone through highly regulated molecular and cellular events such that the entire human skeleton is replaced over the course of each decade of life. Disruption of the homeostatic balance of bone removal and replacement can manifest as pathologic bone loss observed in osteoporosis, periodontal disease, and some inflammatory arthritides or as inappropriate new bone formation (for example spondyloarthritis).

SUMMARY

Provided herein are antibodies, including monoclonal antibodies, that specifically bind to an epitope of dendritic cell-specific transmembrane protein (DC-STAMP). Specifically, the antibody binds to an epitope of DC-STAMP comprising the amino acid sequence Glu-Val-His-Leu-Lys-Leu-His-Gly-Glu-Lys-Gln-Gly-Thr-Gln (SEQ ID NO:1). Optionally, the epitope comprises the amino acid sequence Lys-Gln-Gly-Thr-Gln (SEQ ID NO:3)

Also provided are compositions comprising the antibody. Specifically, the composition comprises an antibody that specifically binds to an epitope of DC-STAMP, wherein the epitope of DC-STAMP comprises SEQ ID NO:3.

Also provided are methods of inhibiting osteoclastogenesis in a cell (e.g., an osteoclast or osteoclast precursor cell). The methods comprise administering to the cell a composition comprising an antibody that specifically binds an epitope of DC-STAMP.

Further provided are nucleic acid sequences and amino acid sequences encoding the heavy and light chain immunoglobulins of the antibody that specifically binds DC-STAMP. Also detailed are vectors that include the nucleic acid sequences that encodes the heavy and/or light chain immunoglobulins or portions thereof (e.g., complementarity determining regions (CDRs)) of the antibody that specifically binds DC-STAMP and the host cells transformed with the vector or vectors that encode the heavy and/or light chain immunoglobulins or portions thereof.

DESCRIPTION OF DRAWINGS

FIG. 1 shows that the 1A2 mAb recognizes DC-STAMP and indicates its protein levels in mature OC.

FIG. 2 shows surface DC-STAMP+ cells express myeloid lineage markers.

FIG. 3 shows the temporal dynamics of DC-STAMP gene expression during OC and mDC differentiation conditions. FIG. 3A (right panel) shows a representative fluorescent image of bone marrow derived cells cultured with IL-4+GM-CSF and stained with phalloidin to highlight actin in dendritic processes.

FIG. 4 shows that the surface and intracellular flow cytometry reveal differential expression patterns for DC-STAMP protein in OC and mDC development as well as heterogeny in OCP during osteoclastogenesis.

FIG. 5 shows surface flow cytometry and intracellular immunofluorescence reveal differential expression patterns for DC-STAMP protein in human OC and mDC development similar to that seen in murine cells.

FIG. 6 shows phenotyping of the RANKL-induced surface DC-STAMP$^{lo}$ and surface DC-STAMP$^{hi}$ cells.

FIG. 7 shows Gr1$^{lo}$ PBMC contain both DC-STAMP$^{lo}$ and DC-STAMP$^{hi}$ populations while Gr1$^{hi}$ PBMC contain a DC-STAMP$^{hi}$ population. FIG. 7B (right panel) shows representative flow cytometry dot plots of the R2 region further electronically gated into Gr1$^{lo}$ (R3) and Gr1$^{hi}$ (R4) regions. Numbers indicate relative percentage of cells in each region.

FIG. 8 shows RANKL-induced DC-STAMP$^{lo}$ cells represent a more osteoclastogenic subtype of OCP and are necessary for the formation of large TRAP+ multinucleated cells. FIG. 8B (right panel) shows a bar graph demonstrating relative DC-STAMP mRNA fold change in human RANKL-induced DC-STAMP$^{lo}$ (black bar) and DC-STAMP$^{hi}$ (white bar) cells. Graphs are representative of experiments done in triplicate and data are normalized to β-actin. * P<0.05 vs. DC-STAMP$^{lo}$ gene expression levels.

FIG. 9 shows a surface DC-STAMP-expressing subset of cells exists among CD14+ human monocytes bearing fusion-related surface proteins.

FIG. 10 shows a greater percentage of CD11b+ express surface DC-STAMP in inflammatory erosive arthritis.

FIG. 11 shows IFN-α prevents RANKL-induced development of a DC-STAMP$^{lo}$ cell and maintains the DC-STAMP$^{hi}$ phenotype.

FIG. 12 shows RANKL-induced DC-STAMP$^{lo}$ OCP express more type I IFN than DC-STAMP$^{hi}$ OCP and are capable of generating TRAP+ multinucleated cells in co-culture with cells exposed to IFN-α.

FIG. 13 shows NZB×NZW F1 mice with non-erosive and Ad-IFN-α treated NZW mice with SIA have a smaller CD11b+DC-STAMP$^{lo}$ PBMC frequency and a prominent CD11b+DC-STAMP$^{hi}$ PBMC population.

FIG. 14 shows an elevated IFN-α transcriptome correlates significantly with lower CD11b+DC-STAMP$^{lo}$ PBMC frequency. A lower CD11b+DC-STAMP$^{lo}$ PBMC frequency correlates significantly with higher bone volume.

FIG. 15 shows a functional characterization of the DC-STAMP mAb 1A2. FIG. 15D(c) shows a graph of the average OC counts in the absence (left bar, 489±284) or presence (right bar, 60±107) of 1A2 in the cell culture. The permutation test with $10^5$ re-samplings for statistic analysis was employed. The permutation test showed a significant difference between two culture conditions (p=0.013). Data shown were for 6 subjects analyzed and listed in Table 2.

FIG. 16 shows that DC-STAMP is expressed on the surface of monocytes and a small subset of CD3+ cells on human PBMC.

FIG. 17 shows that human PBMC have four distinct DC-STAMP expression patterns that differ between Ps/PsA and HC subjects. FIG. 17B shows the number of subjects observed in each pattern. Fisher's exact shows significant difference among HC, Ps and PsA in the DC-STAMP patterns (pvalue=0.0119). Table 3 summarizes the DC-STAMP patterns and the distribution of HC and Ps/PsA patients in these four patterns.

FIG. 18 shows that DC-STAMP is down-regulated in human monocytes during ostoeclastogenesis. FIG. 18A shows a dynamic changes of DC-STAMP surface expression on human monocytes during osteoclastogenesis. Enriched human monocytes were cultured in media supplemented with RANKL and M-CSF, and the surface expression of DC-STAMP was examined at different time points (a: day0, b: day1, c: day2, d: day5, e: day7). Solid lines in each panel represent the original DC-STAMP expression level on fresh monocytes and open lines show the expression of DC-STAMP at the various time points. FIG. 18B shows images demonstrating the cellular localization of DC-STAMP. Human monocytes were cultured with RANKL+M-CSF for 8 days, fixed and immunostained with DAPI which binds to nuclei, 1A2 anti-DC-STAMP-FITC, and rhodamine phalloidin for actin. The images show the localization of DC-STAMP on a spindle-shaped pro-OC (a) and on mature OC (b). Cells shown in (a) and (b) were cultured on a single slide with the same magnification. The images are representative of ten cells with similar phenotypes (mononuclear vs. multi-nucleated, and spindle-shaped vs. large round shape).

FIG. 19 shows DC-STAMP$^{high}$ cells demonstrate higher osteoclastogenesis potential.

FIG. 20 shows that DC-STAMP proteins are phosphorylated on tyrosine residues and associate with CD16 and SHP-1.

DETAILED DESCRIPTION

Figure 1A:
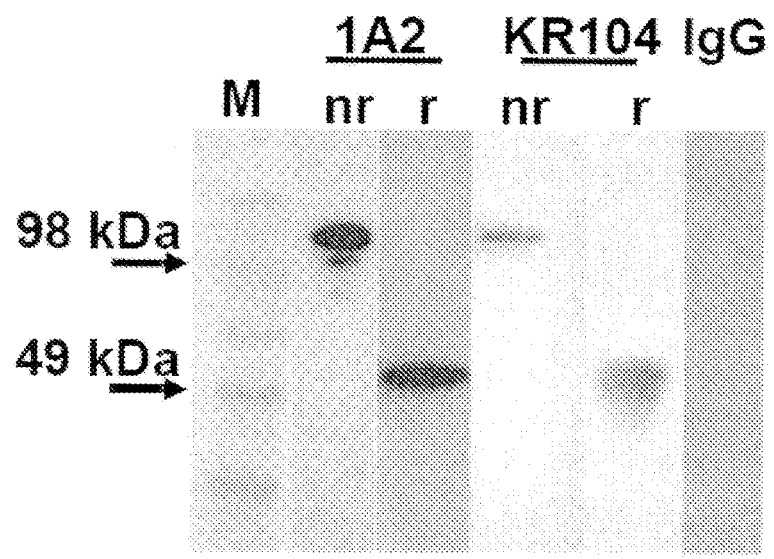
FIG. 1A shows immunoprecipitation-immunoblotting of cell lysate from CD11b+ RAW 264.7 cells treated with RANKL for 2 days to generate OCP. After immunoprecipitation with the 1A2 mAb, immunoblotting was performed with either the 1A2 mAb, the KR104 rabbit polyclonal antibody (positive control), or an anti-mouse IgG antibody (negative control) under non-reducing (nr: −β-mercaptoethanol) or reducing (r: +β-mercaptoethanol) conditions. M: protein marker, black and white scanned overlay. Blot is representative of 4 separate trials.

Provided herein are antibodies that specifically bind an epitope of DC-STAMP. Specifically, provided herein are monoclonal antibodies that bind an epitope of DC-STAMP, wherein the epitope comprises the amino acid sequence Glu-Val-His-Leu-Lys-Leu-His-Gly-Glu-Lys-Gln-Gly-Thr-Gln (SEQ ID NO:1). Optionally, the epitope comprises the amino acid sequence His-Gly-Glu-Lys-Gln-Gly-Thr-Gln (SEQ ID NO:2). Optionally, the epitope comprises the amino acid sequence Lys-Gln-Gly-Thr-Gln (SEQ ID NO:3). Optionally, a light chain of the monoclonal antibody comprises SEQ ID NO:5 or one or more variable regions thereof. Optionally, a heavy chain of the monoclonal antibody comprises SEQ ID NO:6 or one or more variable regions thereof.

Also provided are compositions comprising an antibody, wherein the composition comprises an antibody that specifically binds to an epitope of DC-STAMP, and wherein the epitope of DC-STAMP comprises SEQ ID NO:1, SEQ ID NO:2, or SEQ ID NO:3. The antibody can, for example comprise a light chain comprising SEQ ID NO:5 or one or more variable regions thereof. The antibody can, for example, comprise a heavy chain comprising SEQ ID NO:6 or one or more variable regions thereof. The antibody can, for example, be a monoclonal antibody. The composition can, for example, further comprise a pharmaceutically acceptable carrier.

Further provided are methods of inhibiting osteoclastogenesis in a cell. The methods comprise administering to the cell a composition comprising an antibody (e.g., a blocking antibody) that specifically binds to an epitope of DC-STAMP. Optionally, a light chain of the antibody comprises SEQ ID NO:5 or one or more variable regions thereof. Optionally, a heavy chain of the antibody comprises SEQ ID NO:6 or one or more variable regions thereof. Optionally, the antibody is a monoclonal antibody. Optionally, the epitope of DC-STAMP comprises SEQ ID NO:1, SEQ ID NO:2, or SEQ ID NO:3. The composition can, for example, be administered in vitro or to a subject in vivo. The cell can, for example, be a mammalian cell. Optionally, the mammalian cell can be a human cell. Cells can include progenitor cells, stem cells osteoclasts, and the like.

As used herein, the term antibody encompasses, but is not limited to, whole immunoglobulin (i.e., an intact antibody) of any class. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called alpha, delta, epsilon, gamma, and mu, respectively.

The term variable is used herein to describe certain portions of the antibody domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a β-sheet configuration, connected by three CDRs, which form loops connecting, and in some cases forming part of the β-sheet structure. The CDRs in each chain are held together in close proximity by the FR regions and, with the CDRs from the other chain, contribute to the formation of the antigen binding site of antibodies. The constant domains are not involved directly in binding an antibody to an antigen, but exhibit various effector functions, such as participation of the antibody in antibody-dependent cellular toxicity.

As used herein, the term epitope is meant to include any determinant capable of specific interaction with the provided antibodies. Epitopic determinants usually consist of chemically active surface groupings of molecules such as amino acids or sugar side chains and usually have specific three dimensional structural characteristics, as well as specific charge characteristics. Identification of the epitope that the antibody recognizes is performed as follows. First, various partial structures of the target molecule that the monoclonal antibody recognizes are prepared. The partial structures are prepared by preparing partial peptides of the molecule. Such peptides are prepared by, for example, known oligopeptide synthesis technique or by incorporating DNA encoding the desired partial polypeptide in a suitable expression plasmid. The expression plasmid is delivered to a suitable host, such as E. coli, to produce the peptides. For example, a series of polypeptides having appropriately reduced lengths, working from the C- or N-terminus of the target molecule, can be prepared by established genetic engineering techniques. By establishing which fragments react with the antibody, the epitope region is identified. The epitope is more closely identified by synthesizing a variety of smaller peptides or mutants of the peptides using established oligopeptide synthesis techniques. The smaller peptides are used, for example, in a competitive inhibition assay to determine whether a specific peptide interferes with binding of the antibody to the target molecule. If so, the peptide is the epitope to which the antibody binds. Commercially available kits, such as the SPOTs Kit (Genosys Biotechnologies, Inc., The Woodlands, Tex.) and a series of multipin peptide synthesis kits based on the multipin synthesis method (Chiron Corporation, Emeryvile, Calif.) may be used to obtain a large variety of oligopeptides.

The term antibody or fragments thereof can also encompass chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain DC-STAMP binding activity are included within the meaning of the term antibody or fragment thereof. Such antibodies and fragments can be made by techniques known in the art and can be screened for specificity and activity according to general methods for producing antibodies and screening antibodies for specificity and activity (See Harlow and Lane. Antibodies, A Laboratory Manual. Cold Spring Harbor Publications, New York (1988)).

Also included within the meaning of antibody or fragments thereof are conjugates of antibody fragments and antigen binding proteins (single chain antibodies) as described, for example, in U.S. Pat. No. 4,704,692.

Optionally, the antibody is a monoclonal antibody. The term monoclonal antibody as used herein refers to an antibody from a substantially homogeneous population of antibodies, i.e., the individual antibodies comprising the population are identical except for possible naturally occurring mutations that may be present in minor amounts. Monoclonal antibodies may be prepared using hybridoma methods, such as those described by Kohler and Milstein, Nature, 256:495 (1975) or Harlow and Lane, Antibodies, A Laboratory Manual. Cold Spring Harbor Publications, New York (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent can be DC-STAMP or an immunogenic fragment thereof.

Generally, either peripheral blood lymphocytes (PBLs) are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, pp. 59-103 (1986)). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium") substances that prevent the growth of HGPRT-deficient cells.

Immortalized cell lines useful here are those that fuse efficiently, support stable high level expression of antibody by the selected antibody-producing cells, and are sensitive to a medium such as HAT medium. Immortalized cell lines include murine myeloma lines, which can be obtained, for instance, from the Salk Institute Cell Distribution Center; San Diego, Calif. and the American Type Culture Collection; Rockville, Md. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, pp. 51-63 (1987)).

The culture medium in which the hybridoma cells are cultured can then be assayed for the presence of monoclonal antibodies directed against DC-STAMP or selected epitopes thereof. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art, and are described further in Harlow and Lane Antibodies, A Laboratory Manual, Cold Spring Harbor Publications, New York (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells can serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567) or by covalently joining to the immunoglobulin coding sequence all or part of the coding sequence for a non-immunoglobulin polypeptide. Such a non-immunoglobulin polypeptide can be substituted for the constant domains of an antibody provided herein, or can be substituted for the variable domains of one antigen-combining site of an antibody to create a chimeric bivalent antibody comprising one antigen-combining site having specificity for DC-STAMP and another antigen-combining site having specificity for a different antigen.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment that has two antigen combining sites and is still capable of cross-linking antigen.

The Fab fragments produced in the antibody digestion can also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group.

One method of producing proteins comprising the provided antibodies or polypeptides is to link two or more peptides or polypeptides together by protein chemistry techniques. For example, peptides or polypeptides can be chemically synthesized using currently available laboratory equipment using either Fmoc (9-fluorenylmethyl-oxycarbonyl) or Boc (tert-butyloxycarbonoyl) chemistry (Applied Biosystems, Inc.; Foster City, Calif.). Those of skill in the art readily appreciate that a peptide or polypeptide corresponding to the antibody provided herein, for example, can be synthesized by standard chemical reactions. For example, a peptide or polypeptide can be synthesized and not cleaved from its synthesis resin whereas the other fragment of an antibody can be synthesized and subsequently cleaved from the resin, thereby exposing a terminal group that is functionally blocked on the other fragment. By peptide condensation reactions, these two fragments can be covalently joined via a peptide bond at their carboxyl and amino termini, respectively, to form an antibody, or fragment thereof. (Grant, Synthetic Peptides: A User Guide. W.H. Freeman and Co., N.Y. (1992); Bodansky and Trost, Ed., Principles of Peptide Synthesis, Springer Verlag Inc., NY (1993)). Alternatively, the peptide or polypeptide can by independently synthesized in vivo. Once isolated, these independent peptides or polypeptides may be linked to form an antibody or fragment thereof via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-9 (1994)). The first step is the chemoselective reaction of an unprotected synthetic peptide a thioester with another unprotected peptide segment containing an amino terminal Cys residue to give a thioester linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Baggiolini et al., FEBS Lett. 307:97-101 (1992); Clark et al., J. Biol. Chem. 269:16075 (1994); Clark et al., Biochemistry 30:3128 (1991); Rajarathnam et al., Biochemistry 33:6623-30 (1994)).

Alternatively, unprotected peptide segments can be chemically linked where the bond formed between the peptide segments as a result of the chemical ligation is an unnatural (non peptide) bond (Schnolzer et al., Science 256:221 (1992)). This technique has been used to synthesize analogs of protein domains as well as large amounts of relatively pure proteins with full biological activity (deLisle et al., Techniques in Protein Chemistry IV. Academic Press, New York, pp. 257-67 (1992)).

The provided polypeptide fragments can be recombinant proteins obtained by cloning nucleic acids encoding the polypeptide in an expression system capable of producing the polypeptide fragments thereof, such as a bacterial, adenovirus or baculovirus expression system. For example, one can determine the active domain of an antibody from a specific hybridoma that can cause a biological effect associated with the interaction of the antibody with DC-STAMP. For example, amino acids found to not contribute to either the activity or the binding specificity or affinity of the antibody can be deleted without a loss in the respective activity.

The provided fragments, whether attached to other sequences, can also include insertions, deletions, substitutions, or other selected modifications of particular regions or specific amino acids residues, provided the activity of the fragment is not significantly altered or impaired compared to the nonmodified antibody or epitope. These modifications can provide for some additional property, such as to remove or add amino acids capable of disulfide bonding, to increase its bio longevity, to alter its secretory characteristics, and the like. In any case, the fragment can possess a bioactive property, such as binding activity, regulation of binding at the binding domain, and the like. Functional or active regions may be identified by mutagenesis of a specific region of the protein, followed by expression and testing of the expressed polypeptide. Such methods are readily apparent to a skilled practitioner in the art and can include site specific mutagenesis of the nucleic acid encoding the antigen. (Zoller et al., Nucl. Acids Res. 10:6487-500 (1982)).

Further provided herein is a humanized or human version of the antibody. Optionally, the antibody modulates the activity of the DC-STAMP molecule by activating or inhibiting the DC-STAMP molecule. Optionally, the humanized or human antibody comprises at least one complementarity determining region (CDR) of an antibody having the same epitope specificity as an antibody produced by the hybridoma cell line disclosed herein. For example, the antibody can comprise all CDRs of an antibody having the same epitope specificity as an antibody produced by the hybridoma cell line.

Optionally, the humanized or human antibody can comprise at least one residue of the framework region of light or heavy chains provided in SEQ ID NO:5 or SEQ ID NO:6. Humanized and human antibodies can be made using methods known to a skilled artisan; for example, the human antibody can be produced using a germ-line mutant animal or by a phage display library.

Antibodies can also be generated in other species and humanized for administration to humans. Alternatively, fully human antibodies can also be made by immunizing a mouse or other species capable of making a fully human antibody (e.g., mice genetically modified to produce human antibodies) and screening clones that bind DC-STAMP. See, e.g., Lonberg and Huszar, Int. Rev. Immunol. 13:65-93, (1995), which is incorporated herein by reference in its entirety for methods of producing fully human antibodies. As used herein, the term humanized and human in relation to antibodies, relate to any antibody which is expected to elicit a therapeutically tolerable weak immunogenic response in a human subject. Thus, the terms include fully humanized or fully human as well as partially humanized or partially human.

Humanized forms of non-human (e.g., murine) antibodies are chimeric immunoglobulins, immunoglobulin chains or fragments thereof (such as Fv, Fab, Fab', F(ab')2, or other antigen-binding subsequences of antibodies) which contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues that are found neither in the recipient antibody nor in the imported CDR or framework sequences. In general, the humanized antibody will comprise substantially all or at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522-5 (1986); Riechmann et al., Nature, 332:323-7 (1988); and Presta, Curr. Op. Struct. Biol., 2:593-6 (1992)).

Generally, a humanized antibody has one or more amino acid residues introduced into it from a source that is non-human. These non-human amino acid residues are often referred to as import residues, which are typically taken from an import variable domain. Humanization can be essentially performed following the methods described in Jones et al., Nature 321:522-5 (1986); Riechmann et al., Nature 332:323-7 (1988); or Verhoeyen et al., Science 239:1534-6 (1988), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The nucleotide sequences encoding the provided antibodies can be readily isolated and sequenced using conventional procedures (e.g., by using oligonucleotide probes that are capable of binding specifically to genes encoding the heavy and light chains of murine antibodies). These nucleotide sequences can also be modified, or humanized, for example, by substituting the coding sequence for human heavy and light chain constant domains in place of the homologous murine sequences (see, e.g., U.S. Pat. No. 4,816,567). The nucleotide sequences encoding any of the provided antibodies can be expressed in appropriate host cells. These include prokaryotic host cells including, but not limited to, *E. coli, Bacillus subtilus*, other enterobacteriaceae such as *Salmonella typhimurium* or *Serratia marcesans*, and various *Pseudomonas* species. Eukaryotic host cells can also be utilized. These include, but are not limited to, yeast cells (for example, *Saccharomyces cerevisiae* and *Pichia pastoris*), and mammalian cells such as VERO cells, HeLa cells, Chinese hamster ovary (CHO) cells, W138 cells, BHK cells, COS-7 cells, 293T cells and MDCK cells. The antibodies produced by these cells can be purified from the culture medium and assayed for binding, activity, specificity or any other property of the monoclonal antibodies by utilizing the methods set forth herein and standard in the art.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA 90:2551-5 (1993); Jakobovits et al., Nature 362:255-8 (1993); Bruggemann et al., Year in Immuno. 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, ed., p. 77 (1985); Boerner et al., J. Immunol., 147(1):86-95 (1991)).

The provided antibody or fragment can be labeled or fused with another polypeptide or fragment thereof. For example, the provided antibodies or fragments thereof can be fused with a therapeutic agent. Thus, an antibody or fragment thereof that binds to DC-STAMP may be linked to a therapeutic agent. The linkage can be covalent or noncovalent (e.g., ionic). Therapeutic agents include but are not limited to toxins, including but not limited to plant and bacterial toxins, small molecules, peptides, polypeptides and proteins. Genetically engineered fusion proteins, in which genes encoding for an antibody or fragments thereof, including the Fv region, can be fused to the genes encoding a toxin to deliver a toxin to the target cell are also provided. As used herein, a target cell or target cells are DC-STAMP positive cells.

Other examples of therapeutic agents include chemotherapeutic agents, a radiotherapeutic agent, and immunotherapeutic agent, as well as combinations thereof. In this way, the antibody complex delivered to the subject can be multifunctional, in that it exerts one therapeutic effect by binding to the DC-STAMP and a second therapeutic by delivering a supplemental therapeutic agent.

The therapeutic agent can act extracellularly, for example by initiating or affecting an immune response, or it can act intracellularly, either directly by translocating through the cell membrane or indirectly by, for example, affecting transmembrane cell signaling. The therapeutic agent is optionally cleavable from the antibody or fragment. Cleavage can be autolytic, accomplished by proteolysis, or affected by contacting the cell with a cleavage agent. Moreover, the antibody or fragments thereof can also act extracellularly, for example by initiating, affecting, enhancing or reducing an immune response without being linked in a molecular complex with a therapeutic agent. Such an antibody is known in the art as an unconjugated antibody. An unconjugated antibody can directly induce negative growth signal or apoptosis or indirectly activate a subject's defense mechanism to mediate anti-tumor activity. The antibody or fragment can be modified to enhance antibody-dependent cell killing. For example, amino acid substitutions can be made in the Fc region of the antibodies or fragments disclosed herein to increase binding of Fc receptors for enhanced antibody dependent cell cytotoxicity or increased phagocytosis. The antibody or fragment can also be used to induce cell proliferation. By inducing cell proliferation, the effects of a chemotherapeutic or radiotherapeutic agent described herein can be enhanced.

Examples of toxins or toxin moieties include diphtheria, ricin, streptavidin, and modifications thereof. An antibody or antibody fragment may be conjugated to a therapeutic moiety such as a cytotoxin, a therapeutic agent or a radioactive metal ion. A cytotoxin or cytotoxic agent includes any agent that is detrimental to cells. Examples include paclitaxel, cisplatin, carboplatin, cytochalasin B, gramicidin D, ethidium bromide, emetine, etoposide, tenoposide, colchicin, dihydroxy anthracin dione, mitoxantrone, mithramycin, actinomycin D, 1-dehydrotestosterone, glucocorticoids, procaine, tetracaine, lidocaine, propranolol, puromycin and analogs or homologs thereof. Therapeutic agents include, but are not limited to, antimetabolites (e.g., methotrexate, 6-mercaptopurine, 6-thioguanine, cytarabine, 5-fluorouracil, decarbazine), alkylating agents (e.g., mechlorethamine, thiotepa, chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Techniques for conjugating such a therapeutic moiety to antibodies are well known, see, e.g., Amon et al., Monoclonal Antibodies And Cancer Therapy, Reisfeld et al. (eds.), pp. 243-56 (1985); Hellstrom et al., Controlled Drug Delivery (2nd Ed.), Robinson et al. (eds.), pp. 623-53 (1987); Thorpe, Monoclonal Antibodies '84:Biological And Clinical Applications, Pinchera et al. (eds.), pp. 475-506 (1985); "Analysis, Results, And Future Prospective Of The Therapeutic Use Of Radiolabeled Antibody In Cancer Therapy" in Monoclonal Antibodies For Cancer Detection And Therapy, Baldwin et al. (eds.), pp. 303-16 (1985), and Thorpe et al., Immunol. Rev. 62:119-58 (1982). Alternatively, an antibody can be conjugated to a second antibody to form an antibody heteroconjugate as described in U.S. Pat. No. 4,676,980.

Provided herein is a DC-STAMP antibody, a humanized DC STAMP antibody, heavy and light chain immunoglobulins of a DC-STAMP antibody, CDRs of the DC-STAMP antibody, and certain truncations of these antibodies or immunoglobulins that perform the functions of the full length antibody or immunoglobulin. For example, the nucleic acid sequence coding for the DC-STAMP antibodies can be altered. As such, nucleic acids that encode the polypeptide sequences, variants, and fragments of thereof are disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

As with all peptides, polypeptides, and proteins, including fragments thereof, it is understood that additional modifications in the amino acid sequence of the DC-STAMP antibodies can occur that do not alter the nature or function of the peptides, polypeptides, or proteins. Such modifications include conservative amino acids substitutions and are discussed in greater detail below.

The DC-STAMP antibodies provided herein have a desired function. The DC-STAMP antibody binds a specific epitope of the DC-STAMP protein. Binding of the epitope can, for example, inhibit osteoclastogenesis.

The DC-STAMP antibodies described herein can be further modified and varied so long as the desired function is maintained. It is understood that one way to define any known modifications and derivatives or those that might arise, of the disclosed nucleic acid sequences and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the DC-STAMP antibodies provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman, Adv. Appl. Math 2:482 (1981), by the identity alignment algorithm of Needleman and Wunsch, J. Mol Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Protein modifications include amino acid sequence modifications. Modifications in amino acid sequence may arise naturally as allelic variations (e.g., due to genetic polymorphism) or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at lease one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Provided herein are methods of inhibiting osteoclastogenesis in a cell. Such methods include administering a composition comprising any of the DC-STAMP antibodies provided herein.

Provided herein are compositions comprising the DC-STAMP antibodies described herein. The herein provided compositions are suitable of administration in vitro or in vivo. Optionally, the compositions comprising the DC-STAMP antibodies can further comprise a pharmaceutically acceptable carrier. By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. The carrier is selected to minimize any degradation of the active ingredient and to minimize any adverse side effects in the subject.

Suitable carriers and their formulations are described in *Remington: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the composition, e.g., the polypeptides described herein and the adenovirus encoding an antigen to humans or other subjects.

The compositions are administered in a number of ways depending on whether local or systemic treatment is desired, and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally to present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the nucleic acid molecules or polypeptides are administered by a vector comprising the nucleic acid molecule or a nucleic acid sequence encoding the DC-STAMP antibody. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based deliver systems. Such methods are well known in the art and readily adaptable for use with the compositions and methods described herein.

As used herein, plasmid or viral vectors are agents that transport the disclosed nucleic acids into the cell without undesired degradation and include a promoter yielding expression of the nucleic acid molecule and/or adapter polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virology 61:1213-20 (1987); Massie et al., Mol. Cell. Biol. 6:2872-83 (1986); Haj-Ahmad et al., J. Virology 57:267-74 (1986); Davidson et al., J. Virology 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infections viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided DC-STAMP antibodies and/or nucleic acid molecules encoding the DC-STAMP antibodies can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided DC-STAMP antibodies can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided DC-STAMP antibodies can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding the adapter polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters (e.g., β-actin promoter or EF1α promoter), or from hybrid or chimeric promoters (e.g., CMV promoter fused to the β-actin promoter). Promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g., chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and the term patient or subject includes human and veterinary subjects.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

Isolation of a Novel Monoclonal Antibody to DC-STAMP and the Role of DC-STAMP in Osteoclastogenesis General Methods Reagents. Recombinant RANKL, M-CSF, IL-4, and GM-CSF cytokines were obtained from Cell Sciences (Canton, Mass.). IFN-α was purchased from PBL Biomedical Laboratories (Piscataway, N.J.). The recombinant adenovirus vector containing the mIFN-α subtype 5 cDNA (Ad-IFN-α) was propagated as previously described (Mathian et al., J. Immunol. 174:2499-506 (2005)). Anti-murine antibodies used include: anti-CD16/CD32 to block Fc-receptors (BD Pharmingen; San Jose, Calif.), CD11b-APC clone M1/70 (BD Pharmingen), CD4-PE clone RM2504 (Caltag; Burlingame, Calif.), CD8α-PE/Cy5 clone 53-6.7 (Biolegend; San Diego, Calif.), Gr-1-APC/Cy7 clone RB6-8C5 (Biolegend), STAT1-PE pY701 (BD Biosciences), and CD11c-PE Cy5.5 clone N418 (eBioscience; San Diego, Calif.). Rabbit anti-mouse DC-STAMP polyclonal antibody clone KR104 was purchased from Cosmo Bio (Tokyo, Japan), and mouse IgG isotype control was obtained from Caltag. Anti-human antibodies used include: CD14-APC clone M5E2 (BD Biosciences), CD44-PE/Cy5 clone IM7, SIRPα-PE/Cy7 clone SE5A5, CD47-PerCP/Cy5.5 clone CC2C6, and CD9-PE clone HI9a (Biolegend).

Animals. New Zealand Black (NZB)×New Zealand White (NZW) F1 and NZW/LacJ mice were obtained from Jackson Laboratories (Bar Harbor, Me.). Experiments were performed on 2-, 5-, and 9-month-old female NZB×NZW F1 mice, and age-matched female NZW/LacJ controls. C57Bl/6 and Balb/c mice were also purchased from Jackson Laboratories. The 3647 line of TNF-Tg mice (Keifer et al., EMBO J. 10:4025-31 (1991)), were originally obtained from Dr. G. Kollias (Institute of Immunology, Biomedical Sciences Research Center Alexander Fleming, Vari, Greece) and are maintained as heterozygotes on a C57Bl/6 background. Experiments were performed on female 6-month-old TNF-Tg mice and their non-transgenic littermates as controls.

Cell culture. RAW 264.7 murine monocyte/macrophage-lineage cells were obtained from ATCC (Manassas, Va.). Murine bone marrow cells were obtained as previously described (Takeshita et al., J. Bone Miner. Res. 15:1477-88 (2000)) by flushing mouse femurs and tibias with sterile 1× phosphate-buffered saline (PBS). Splenocytes were obtained by homogenizing the spleen over a cell-strainer into a tube containing 1×PBS. All organs were dissected out of the mice using aseptic technique. Red blood cells (RBC) were removed from the cell suspensions using ACK lysing buffer (BioWhittaker; Walkersville, Md.). Bone marrow-derived cells and splenocytes were cultured in minimal essential media-alpha modification (alpha-MEM, Invitrogen; Carlsbad, Calif.) supplemented with 10% heat-inactivated fetal calf serum (FCS, Hyclone Laboratories; Logan, Utah), 5% penicillin/streptomycin, and 5% minimal essential medium nonessential amino acids (Invitrogen) with a final pH of 7.4. M-CSF (50 ng/mL) was added to the bone marrow-derived cells for 3 days to enrich the adherent CD11b+ population as previously described (Hayashi et al., J. Biol. Chem. 277: 27880-6 (2002)). Other cytokines were added to the CD11b+ enriched bone marrow-derived cells, RAW 264.7 cells, or splenocytes if needed for the specific experiment. RAW 264.7 cells, bone marrow cells, and splenocytes in culture media were incubated at 37° C. in 5% $CO_2$ atmosphere.

Ex-vivo and in-vitro osteoclastogenesis and mDC generation. To generate osteoclasts (OCs) ex-vivo, 10 ng/mL of M-CSF and 5 ng/mL of RANKL were added to $2 \times 10^5$ splenocytes in alpha-MEM in 96-well plates for 7 days with fresh media and cytokines added every 2 days. OC were generated from $2 \times 10^5$ CD11b+ bone marrow-derived cells after 3 days of culture with M-CSF by adding 100 ng/mL of RANKL in alpha-MEM to the cells for 3 more days. Fresh media and cytokines were added every other day. OC were generated in-vitro from RAW 264.7 cells adding 100 ng/mL RANKL to alpha-MEM for 4 days in either 96-well dishes or 100 mm culture plates. To study the effects of IFN-α on OC development, IFN-α (PBL Biomedical Laboratories) was added at 750 U/mL as previously described (Santini et al., J. Exp. Med. 191:1777-88 (2000)). Fresh media and cytokines were added every other day. Cells were then fixed and stained for tartrate-resistant acid phosphatase (TRAP) activity using the Diagnostics Acid Phosphatase Kit (Sigma-Aldrich; St. Louis, Mo.) to identify OC (TRAP+ cells with >3 nuclei), which were quantified as OC area as previously described (Flick et al., J. Orthop. Res. 21:676-84 (2003)).

For the generation of mDC, $2 \times 10^5$ bone marrow cells were cultured for 3 days with 50 ng/mL of M-CSF to enrich the adherent CD11b+ population as previously described (Hayashi et al., J. Biol. Chem. 277:27880-6 (2002)). The CD11b+ bone marrow-derived cells were then cultured in RPMI-1640 (Invitrogen) containing 20 ng/mL IL-4 and 20 ng/mL GM-CSF for 3 more days with fresh media and cytokines added every two days. The generation of mDC by this culture method was evaluated by immunofluorescent staining to visualize dendritic processes.

Immunofluorescent staining. Murine bone marrow-derived cells or human PBMC were cultured on glass coverslips in 12-well dishes with appropriate cytokines. Cells were fixed in 4% PFA for 20 minutes at room temperature for immunofluorescent staining. The cells were then blocked and permeabilized with PBS containing 0.2% BSA and 0.1% saponin for 15 minutes. The coverslips were incubated at room temperature for 2 hours in a humid chamber after which antibodies, DAPI, or phalloidin was added for 45 minutes at room temperature in the blocking and permeabilization solution. Following the incubation, the coverslips were washed with PBS and mounted on slides for imaging. Images were then assembled, pseudo-colored, and overlaid using Adobe Photoshop 7.0 software (Adobe Systems; San Jose, Calif.).

Histology. Long bones from one leg of each mouse were fixed in 10% phosphate-buffered formalin, decalcified in 10% EDTA solution for two weeks at room temperature with gentle stirring and embedded in paraffin. Histology sections were prepared from three contiguous 3 μm sections 500 μm apart, which were stained with alcian blue hematoxylin/orange G (ABH/orange G) or for TRAP using the Diagnostics Acid Phosphatase Kit (Sigma) as previously described (Flick et al., J. Orthop. Res. 21:676-84 (2003)). OC were quantified from TRAP stained sections as previously described using an osteomeasure image analysis software system (Osteometrics; Atlanta, Ga.) and expressed as OC number per mm of bone or culture dish surface (Flick et al., J. Orthop. Res. 21:676-84 (2003)).

Generation of a novel monoclonal antibody against DC-STAMP. A monoclonal antibody (mAb) against DC-STAMP was generated by immunizing mice with a fourteen-amino acid peptide (Glu-Val-His-Leu-Lys-Leu-His-Gly-Glu-Lys-Gln-Gly-Thr-Gln (SEQ ID NO:1)) sharing homology to a sequence in the fourth extracellular domain of both murine and human DC-STAMP. Hybridoma clones with strong signals by EIA generated by this immunization procedure were expanded in SAFC EX-CELL 610 HSF serum-free media (Sigma; St. Louis, Mo.) and used to generate antibody, which was purified using HiTrap protein G and PD10 columns (GE Healthcare Biosciences; Piscataway, N.J.). The 1A2 clone from this process was evaluated and used for all analyses because of its strong EIA response and high yield after purification. The isotype of the 1A2 clone was determined using the Isostrip Monoclonal Antibody Isotyping Kit according to the manufacturer's instructions (Santa Cruz Biotechnology; Santa Cruz, Calif.). Conjugation to FITC was performed using the Molecular Probes labeling kit (Invitrogen).

Immunoblotting. The DC-STAMP mAb was used to immunoprecipitate DC-STAMP from cultured cells. The Native Membrane Protein Extraction Kit (Calbiochem; San Diego, Calif.) was used to extract membrane fraction proteins according to the manufacturer's instructions. The extracted membrane fraction proteins were immunoprecipitated using the EZView Red Protein A Affinity Gel beads (Sigma) after incubation for 1 hour at 4° C. with anti-DC-STAMP mAb to form antibody-antigen complexes.

Following immunoprecipitation, immunoblotting was done using by loading the immunoprecipitated protein onto a 10% gel for SDS-PAGE. The separated proteins were blotted onto a PVDF membrane using a wet-transfer method. After transfer, the membrane was blocked for 1 hour at room temperature with 5% BSA (Sigma) in TBST. Then, either the DC-STAMP mAb clone 1A2, commercially-available rabbit anti-mouse DC-STAMP polyclonal antibody clone KR104, or mouse IgG was added at a 1:1000 dilution in the blocking solution overnight at 4° C. Following washes in TBST, goat anti-mouse IgG horse-radish peroxidase conjugate (BioRad) was added at a 1:3000 dilution, followed by more TBST washes. The blots were developed with the SuperSignal West Femto chemiluminescent substrate kit (Pierce; Rockford, Ill.) and imaged on Kodak scientific films (Eastman Kodak; Rochester, N.Y.).

Flow cytometry and fluorescence activated cell-sorting (FACS). Surface protein staining was performed on murine peripheral blood mononuclear cells (PBMC) and either RAW 264.7 cells or murine bone marrow cells cultured with cytokines as appropriate for the experiment. Peripheral blood was obtained by cardiac puncture and placed into a tube with 0.5% EDTA to prevent clotting. RBC were then removed from the PBMC with ACK lysing buffer. Anti-CD16/CD32 was added to PBMC to block Fc-receptors for 15 minutes. PBMC were then stained in the dark on ice with FITC-conjugated anti-DC-STAMP mAb for 30 minutes in 1×PBS containing 4% FCS (for flow cytometry) or sterile 1×PBS without FCS (for FACS). 7AAD (Invitrogen) was also added to some cells during the 30 minute incubation, and it was used to determine gating for subsequent analysis of DC-STAMP surface protein expression. Permeabilization of the cells for internal staining was performed using the Cytofix/Cytoperm kit (BD Biosciences). CD11b-APC clone M1/70, CD11c-PE Cy5.5 clone N418, CD4-PE clone RM2504, CD8a-PE/Cy5 clone 53-6.7, STAT1pY701-PE, and Gr-1-APC/Cy7 clone RB6-8C5 were used for murine multicolor flow cytometry analyses. CD14-APC clone M5E2, CD44-PE/Cy5 clone IM7, SIRPα-PE/Cy7 clone SE5A5, CD47-PerCP/Cy5.5 clone CC2C6, and CD9-PE clone HI9a were used for human multicolor flow cytometry analysis. If cells could not be analyzed by flow cytometry the same day, they were fixed in 1% PFA and analyzed the following day. Flow cytometry was performed using either a FacsCalibur or an LSR II (Becton Dickinson). FACS was performed on the same day of staining using either a FACS Vantage or a FACS Aria (Becton Dickinson). Data analysis was done with WinMDI 2.9 software (Scripps Research Institute; La Jolla, Calif.).

Serum-induced arthritis (SIA) and in-vivo Ad-IFN-α treatment. Arthritogenic serum was derived from K/BxN mice (Kouskoff et al., Cell 87:811-22 (1996)). The serum was assessed for ability to induce arthritis by intraperitoneal (IP) injection of Balb/c mice (Jackson Laboratories; Bar Harbor, Me.), which are a highly susceptible strain for SIA. Serum in PBS was administered to NZW and NZBxNZW F1 mice by IP injection at a dose of 250 μL per mouse for 5 days, after which spleens, blood and limbs were harvested for subsequent analyses. A titer of $1 \times 10^{11}$ virus particles/mL in PBS was retro-orbitally injected into mice 2 days before arthritogenic serum and 7 days before harvesting spleens, blood and limbs for further analysis.

Volumetric assessment of bone erosion via micro-CT. Bone volume was quantified via high-resolution in-vivo micro-CT (VivaCT 40; Scanco, Southeastern, Pa.) as previously described (Proulx et al., Arthritis Rheum. 56:4024-37 (2007)). Briefly, each joint was scanned at an isotropic resolution of 17.5 m in a custom sample holder at 55 keV, with cone beam mode. The data were reconstructed via Scanco software into Dicom files for analysis. Amira 3.1 software was used to segment and visualize the bones of the ankle or knee joint on the micro-CT scans. The bones were specifically labeled using the Segmentation Editor feature. A density threshold>11,000 AU was set as representing bone, and the labels were reconstructed using the SurfaceGen module to visualize the bone. The threshold was kept constant throughout the study. Since the entire bone is scanned, its volume, as determined from the TissueStatistics module, was used as a quantitative measure of bone erosion.

IFN-α ELISA. The mouse IFN-α ELISA kit (PBL Biomedical Laboratories) was used to evaluate IFN-α production by cells transfected with the Ad-IFN-α vector. The ELISA was performed according to manufacturer instructions on supernatants from 293T cells cultured in media with $1\times10^{11}$ virus particles/mL of either Ad-IFN-α or Ad-Null for 4 days. The control untreated cell supernatant and supernatant from cells treated with Ad-Null virus produced no IFN-α while the supernatant from cells treated with Ad-IFN-α showed a mean OD at 450 nm of 1.089±0.081 corresponding to about 641.5 pg/mL. The ELISA kit was also used to measure serum IFN-α levels in NZB×NZW F1 mice. Serum was collected by centrifuging clotted peripheral blood at 10,000 rpm at room temperature for 5 minutes. There was no detectable IFN-α above background in NZB×NZW F1 mice despite the presence of proteinuria. Though unexpected, these results were in line with previous findings that ELISA for serum IFN-α is not reliable (Hua et al., Arthritis Rheum. 54:1906-16 (2006)).

Anti-dsDNA antibody ELISA. To measure dsDNA antibody titers in the serum of the NZB×NZW F1 and NZW mice in all treatment groups, peripheral blood was obtained by cardiac puncture and allowed to clot. The clotted blood was then centrifuged at 10,000 rpm at room temperature for 5 minutes to separate serum from the cellular components. The serum was then transferred to a new tube and used with a mouse dsDNA total Ig ELISA kit (Alpha Diagnostic International; San Antonio, Tex.) according to the manufacturer's instructions.

Statistical analysis. Data are presented as means±standard error of the mean. Student's t-test or analysis of variance (ANOVA) were performed with a significance level of P<0.05. Linear regression and chi-square analyses were performed with a minimum confidence level of 95%. Statistics were calculated using either Microsoft Excel 9.0 software (Microsoft; Redmond, Wash.) or the GraphPad PRISM software package (GraphPad Software; La Jolla, Calif.).

Results

Figure 1B:
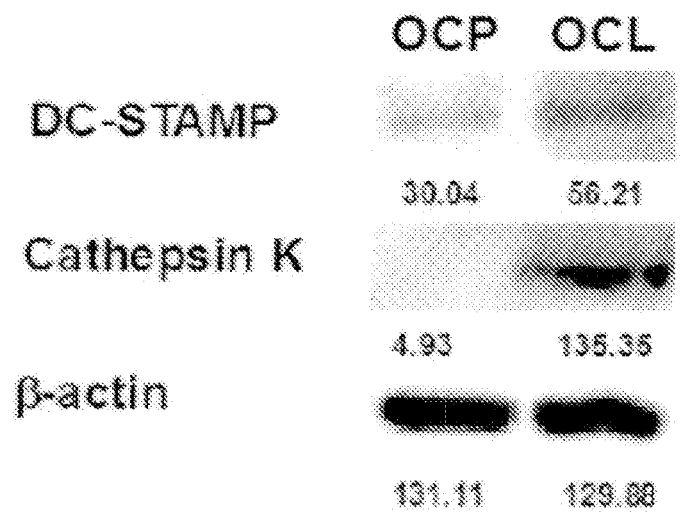
FIG. 1B shows cell lysates from murine bone marrow macrophages cultured with M-CSF and RANKL for 2 days (to generate OCP—osteoclast precursors) or 4 days to generate (OCL—osteoclasts) were immunoblotted with the 1A2 anti-DC-STAMP mAb, cathepsin K (mature OCL marker), and β-actin (loading control). Numbers below bands represent densitometry values used as a semiquantitative measure of relative protein level. Blot is representative of 2 separate trials.
Figure 2A:
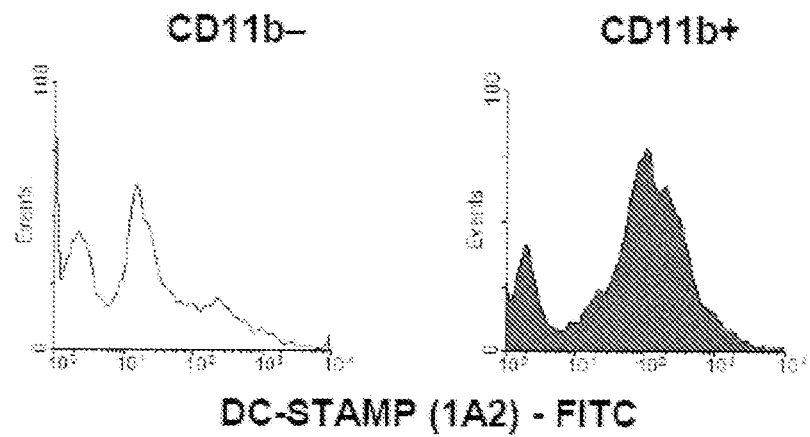
FIG. 2A shows flow cytometry on pooled PBMC from 20-week-old WT C57Bl/6 mice (n=3) showing staining for DC-STAMP-FITC among CD11b+ (solid, right panel) and CD11b− cells (outline, left panel). Histogram is representative of >3 experiments.

A novel monoclonal antibody to detect DC-STAMP surface expression on OCP. To study surface protein expression, a mAb was generated against a peptide in the fourth extracellular domain of DC-STAMP. For comparison, a polyclonal DC-STAMP antibody was used that has histologically shown surface expression on OC (Kukita et al., J. Exp. Med. 200:941-6 (2004)). CD11b+ cells were cultured for 2 days with RANKL and extracted membrane fraction proteins for immunoprecipitation with the 1A2 mAb. FIG. 1A shows that clone 1A2 of the mAb recognizes a protein a little larger than 50 kDa under reducing conditions (r) that is also recognized by the commercially available rabbit polyclonal antibody. Both antibodies also recognize a protein at double the molecular weight (~100 kDa) under non-reducing (nr) conditions. In both reducing and non-reducing conditions, the 1A2 DC-STAMP mAb has a more intense band for the same amount of protein loaded in each lane. Immunoblot analysis of DC-STAMP from total cellular protein lysate during the course of osteoclastogenesis shows DC-STAMP to increase over time as cells mature from OCP to OC in culture with RANKL. Cathepsin K protein levels confirmed the mature state of the cultured OC (FIG. 1B). The 1A2 mAb clone was conjugated to FITC and used to determine if surface membrane DC-STAMP on CD11b+ cells could be detected by flow cytometry. FIG. 2A shows that CD11b+ cells express a higher average amount of DC-STAMP per cell compared to CD11b− cells.

Figure 2B:
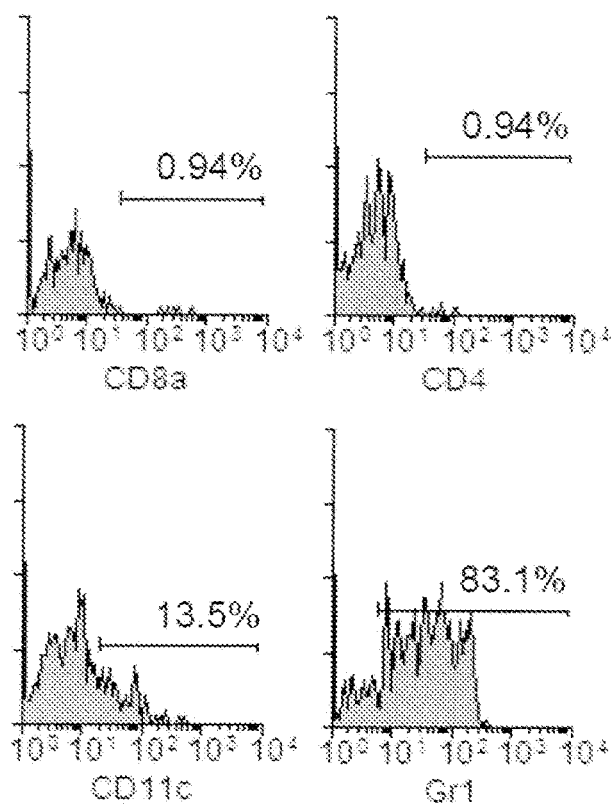
FIG. 2B shows flow cytometry on electronically gated CD11b+DC-STAMP+ pooled bone marrow cells from 20-week-old WT C57Bl/6 mice (n=3) showing multicolor staining for myeloid markers (CD11c and Gr1) and T lymphocyte markers (CD4 and CD8a). Numbers represent percentage of cells in indicated regions.

Since it has previously been shown that OCP arise from CD11b+ bone marrow cells, DC-STAMP+CD11b+ bone marrow cells were immunophenotyped for further characterization. DC-STAMP+CD11b+ cells in C57Bl/6 bone marrow expressed low levels of T cell markers CD4 and CD8 (both about 1%). In contrast, myeloid-lineage markers were more highly expressed among these cells. Of the DC-STAMP+CD11b+ bone marrow cell population, 13.5% were surface CD11c+ and 83.1% were Gr1+ (FIG. 2B).

Figure 3A:
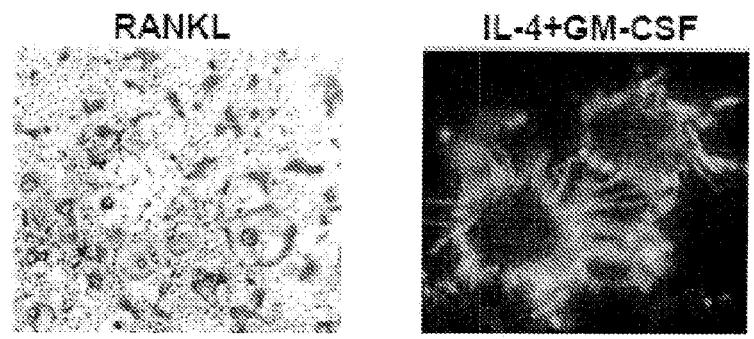
FIG. 3A (left panel) shows a representative TRAP staining of multinucleated cells generated from RANKL culture of bone marrow macrophages.
Figure 3B:
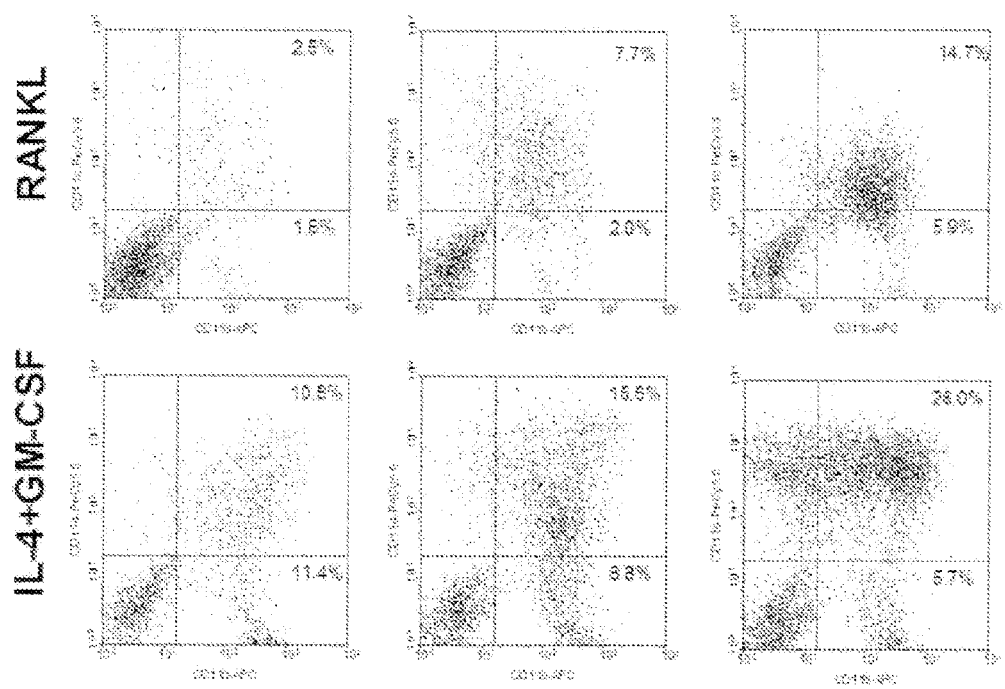
FIG. 3B shows histograms of flow cytometry performed on bone marrow derived cells stained with fluorescently labeled antibodies specific for CD11b and CD11c that were cultured for 3 days with M-CSF to enrich the adherent CD11b+ population. The cells were then further cultured with RANKL or IL-4+GM-CSF for 1, 2, or 3 days. Representative dot plots of >3 experiments are shown.

Conditions favoring osteoclastogenesis exhibit a different DC-STAMP surface and internal protein expression pattern compared to conditions supporting mDC formation. Finding that DC-STAMP surface protein expression could identify cells that have osteoclastogenic potential by flow cytometry, the expression profile of DC-STAMP along the process of OC formation was determined. Since DC-STAMP was originally discovered in mDC, and OC and mDC share a common CD11b+ precursor, the DC-STAMP expression profile in both cell types was compared. To determine if any differences' existed in surface DC-STAMP expression profile under OC-promoting versus mDC-promoting conditions, bone marrow cells from C57Bl/6 mice were treated with M-CSF for 3 days to enrich for the monocyte/macrophage CD11b+ population as previously established (Hayashi et al., J. Biol. Chem. 277:27880-6 (2002)). These cells were then treated with either pro-osteoclastogenic RANKL or with pro-mDC IL-4 plus GM-CSF. After 3 days of culture, the development of either OC via TRAP staining or mDCs by immunofluorescently observing dendrite process formation was assessed (FIG. 3A). The cells were also immunophenotyped at each of the 3 days in the pro-OC or pro-mDC conditions for CD11b and CD11c expression. MDC have previously been described to exhibit a CD11b+CD11c+ phenotype and CD11c expression has been reported to increase during differentiation into mDC (Metlay et al., J. Exp. Med. 171:1753-71 (1990), Adachi et al., Stem Cells 20:61-72 (2002)). Under RANKL exposure, an increase in the proportion of CD11b+ CD11c− cells was noted, which has been shown to represent a population containing OCP (Li et al., Arthritis Rheum. 50:265-76 (2004)). In contrast, there was a decrease in the percentage of this population in cells exposed to IL-4 and GM-CSF. However, culture with IL-4 and GM-CSF increased the percentage of the CD11b+CD11c+ population, as expected (FIG. 3B).

Figure 4A:
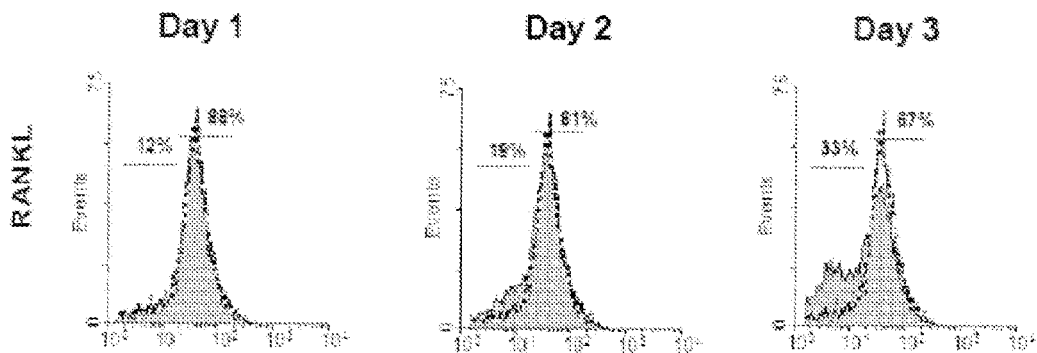
FIG. 4A shows a representative surface flow cytometric histogram showing DC-STAMP-FITC staining of M-CSF enriched CD11b+ adherent bone marrow cells cultured with RANKL for 1, 2, or 3 days. Dotted line indicates level on day 1 while shaded grey histograms represent value for the indicated day. Numbers indicate percentage of cells in the indicated region.
Figure 4B:
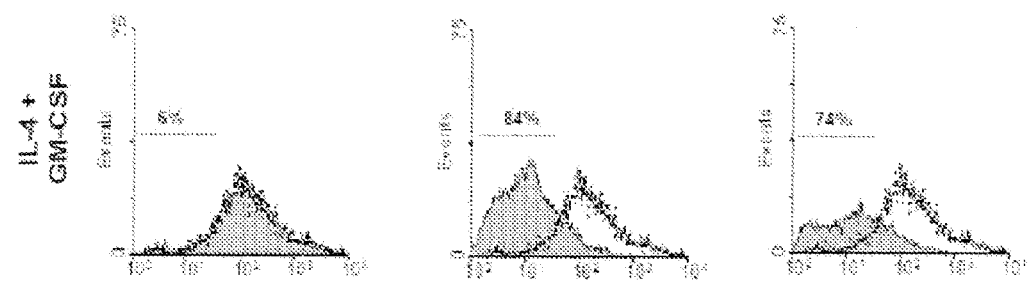
FIG. 4B shows a representative surface flow cytometric histogram showing DC-STAMP-FITC staining of M-CSF enriched CD11b+ adherent bone marrow cells cultured with IL-4+GM-CSF for 1, 2, or 3 days. Dotted line indicates level on day 1 while shaded grey histograms represent value for the indicated day. Numbers indicate percentage of cells in the indicated region.

When bone marrow cells were cultured in osteoclastogenic conditions and analyzed by flow cytometry, a strong single peak for DC-STAMP surface expression was observed at day one of RANKL culture expressed fairly homogeneously among 88% of the CD11b+ cells (FIG. 4A). This is in-line with the finding among CD11b+ cells in murine peripheral blood (FIG. 2A). On day two of culture with RANKL, the percentage of CD11b+ cells expressing surface DC-STAMP began to decline, while a second population of CD11b+DC-STAMP$^{lo}$ cells became more prominent. After 3 days of RANKL culture, this population of RANKL-induced DC-STAMP$^{lo}$ cells increased to 1/3 of the total cultured cells, leaving 67% expressing the original level of DC-STAMP seen on day 1 of culture (FIG. 4A). When this observation was compared to the situation of cells cultured with IL-4+GM-CSF, the shift to cells expressing a lower amount of surface DC-STAMP compared to that observed on the first day of exposure to IL-4+GM-CSF occurred more rapidly and among a greater percentage of the cells compared to the shift seen in culture with RANKL. By day 3 of culture with IL-4+GM-CSF, almost 75% of the cells were expressing a lower amount of surface DC-STAMP compared to day one levels (FIG. 4B).

Figure 4C:
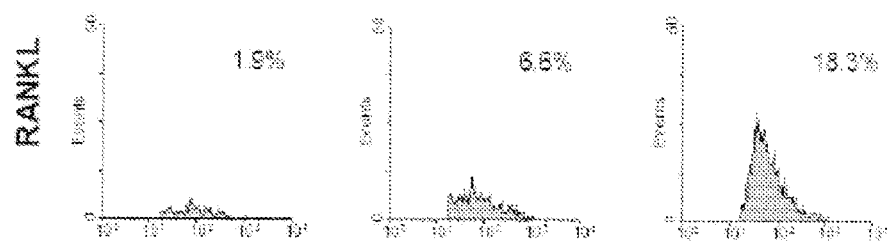
FIG. 4C shows a representative intracellular flow cytometric histogram showing DC-STAMP-FITC staining of M-CSF enriched CD11b+ adherent bone marrow cells cultured with RANKL for 1, 2, or 3 days. Numbers indicate percentage of cells expressing intracellular DC-STAMP.
Figure 4D:
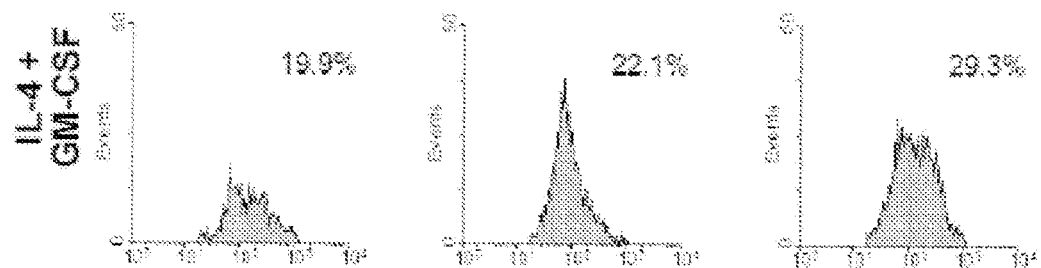
FIG. 4D shows a representative intracellular flow cytometric histogram showing DC-STAMP-FITC staining of M-CSF enriched CD11b+ adherent bone marrow cells cultured with IL-4+GM-CSF for 1, 2, or 3 days. Numbers indicate percentage of cells expressing intracellular DC-STAMP.

To determine what may account for these shifts in surface DC-STAMP expression, internal levels of DC-STAMP were measured over the same period of time under the same culture conditions as surface DC-STAMP analysis. Flow cytometry for internal DC-STAMP protein expression revealed that a very low percentage of cells expressed internal DC-STAMP after 1 day of culture with RANKL compared to the percentage expressing internal DC-STAMP after 1 day of culture with IL-4+GM-CSF (FIGS. 4C and 4D). A higher percentage of cells under pro-mDC culture conditions expressed internal DC-STAMP in relation to the percentage of cells under pro-OC conditions for the 3 days of culture (29% versus 18.3%, respectively).

Figure 5A:
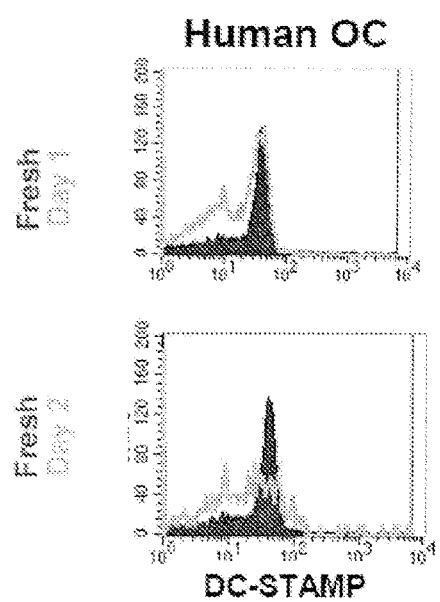
FIGS. 5A and 5B show representative surface flow cytometric histogram showing DC-STAMP-FITC staining of enriched human CD14+ monocytes from peripheral blood of a healthy individual cultured with RANKL and M-CSF (A) or IL-4+GM-CSF (B) for 1, or 2 days. Solid histogram indicates level on day 0 while outlined histograms represent value for the indicated day.
Figure 5B:
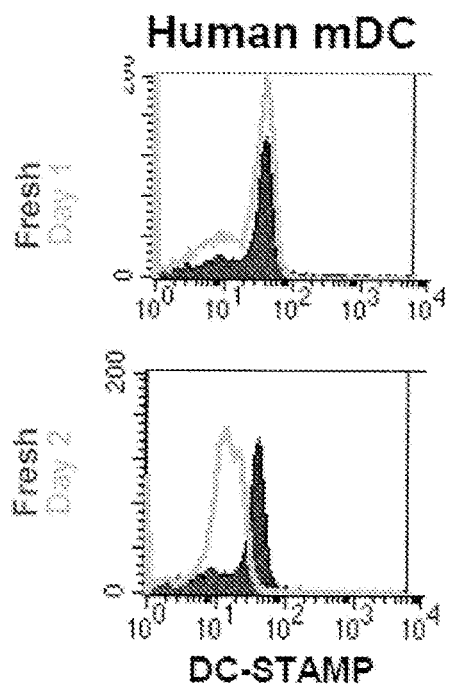
Figure 5C:
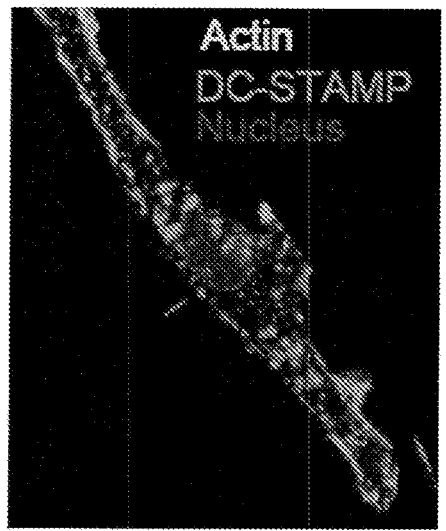
FIG. 5C shows a representative immunofluorescent image demonstrating an enriched human CD14+ monocyte cultured with RANKL and M-CSF and displaying the elongated morphology previously described to be characteristic of OCP as they respond to RANKL stimuli during osteoclastogenesis.
Figure 5D:
FIG. 5D shows a representative immunofluorescent image demonstrating an enriched CD14+ human monocyte cultured with IL-4+GM-CSF and displaying dendritic processes.

Similar findings were observed in human PBMC-derived monocytes treated with either RANKL and M-CSF or IL-4+GM-CSF. As in primary murine cells, human monocytes cultured with RANKL and M-CSF generated two populations of cells based on DC-STAMP surface expression (FIG. 5A). Also in line with the murine data, when cultured with IL-4+GM-CSF, the human monocytes homogeneously expressed lower amounts of surface DC-STAMP compared to the level seen when they were freshly isolated (FIG. 5B). Immunofluorescent staining of cells cultured with RANKL and M-CSF revealed that those cells which exhibited the elongated morphology shown to be characteristic of cells responding to pro-osteoclasteogenic stimuli (Takeshita et al., J. Bone Miner. Res. 15:1477-88 (2000)) had internalized DC-STAMP (FIG. 5C). Immunofluorescent staining of cells cultured with IL-4+GM-CSF also revealed intracellular DC-STAMP (FIG. 5D). Again, the pattern observed intracellularly by flow cytometry in murine cells was replicated by immunofluorescence staining of human cells under the same culture conditions.

Figure 6A:
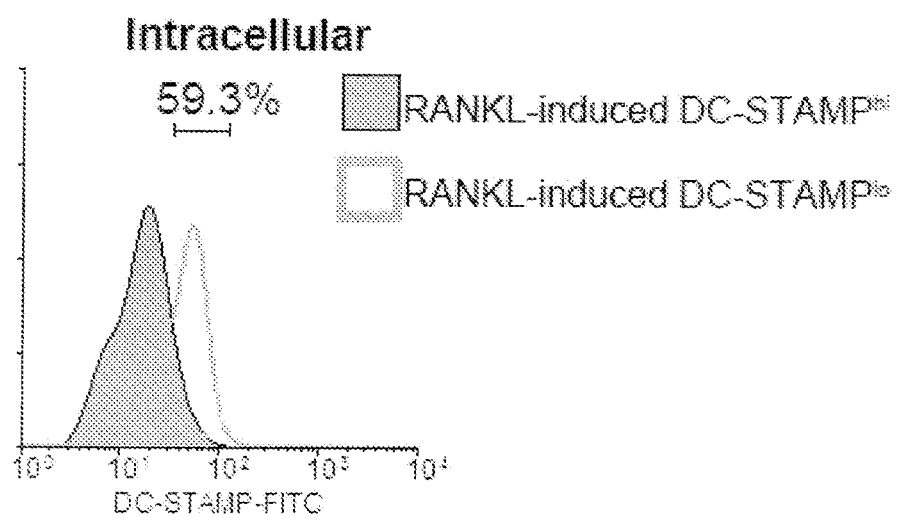
FIG. 6A shows a representative intracellular flow cytometry histogram showing DC-STAMP-FITC staining of sorted RAW 264.7 RANKL-induced surface DC-STAMP$^{lo}$ (open histogram) and DC-STAMP$^{lo}$ cells (shaded histogram).

FACS was used to sort OCP cultured with RANKL based on DC-STAMP$^{hi}$ and DC-STAMP$^{lo}$ surface expression and performed intracellular flow cytometry to determine if there were differences in the internal DC-STAMP levels between these two newly-identified populations (FIG. 6A). Flow cytometry for intracellular DC-STAMP showed that RANKL-induced DC-STAMP$^{lo}$ cells had a greater MFI of intracellular DC-STAMP compared to RANKL-induced DC-STAMP$^{hi}$ cells. There was a greater percentage of DC-STAMP$^{lo}$ cells (59%) with this level of intracellular DC-STAMP MFI compared to the percentage of DC-STAMP$^{hi}$ cells (11%).

Figure 6B:
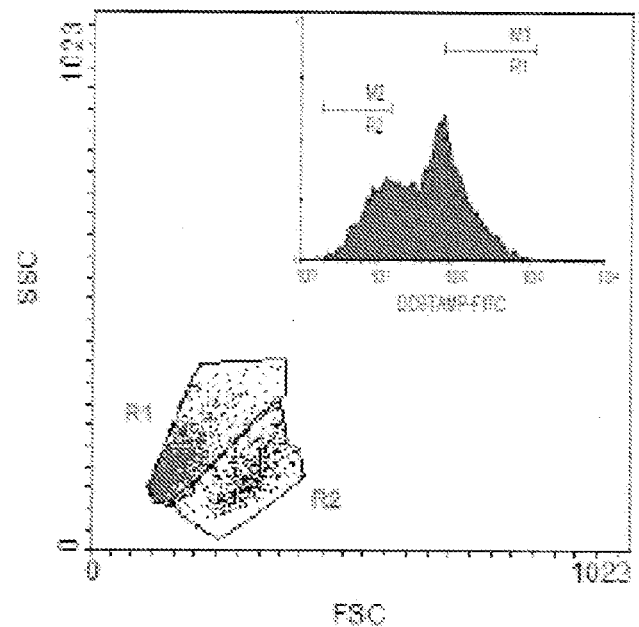
FIG. 6B shows a representative flow cytometry histogram of RAW 264.7 cells cultured with RANKL for 3 days and electronically gated as surface DC-STAMP$^{hi}$ (R1) and surface DC-STAMP$^{lo}$ (R2) then analyzed for forward scatter and side scatter (dot plot).
Figure 6C:
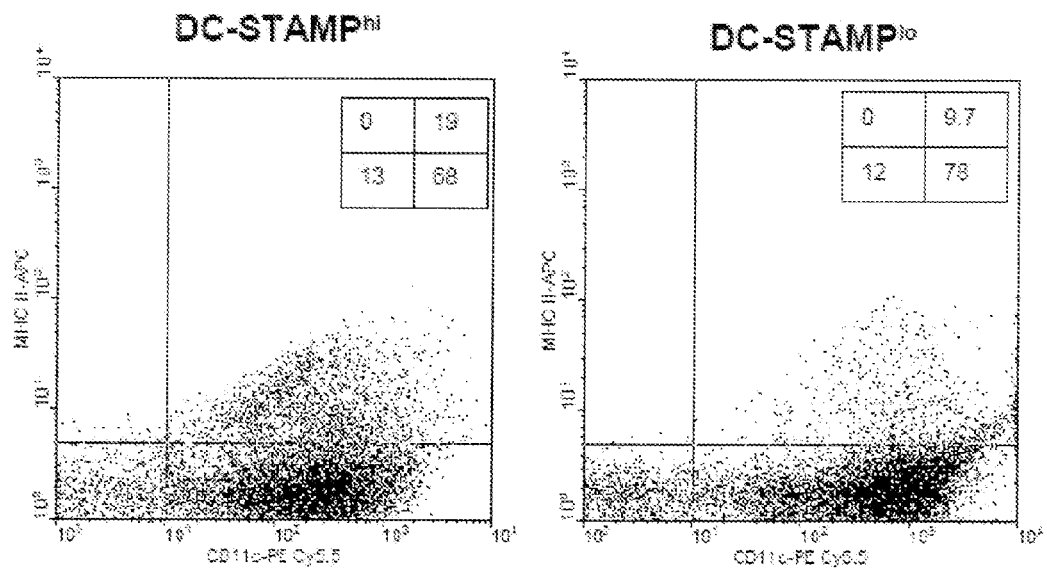
FIG. 6C shows representative dot plots of RANKL-induced DC-STAMP$^{hi}$ and RANKL-induced DC-STAMP$^{hi}$ cells that were sorted and recultured with IL-4 and GM-CSF for 3 days. After this time, the cells were stained for MHCII and CD11c expression using specific fluorescently labeled antibodies.
Figure 7A:
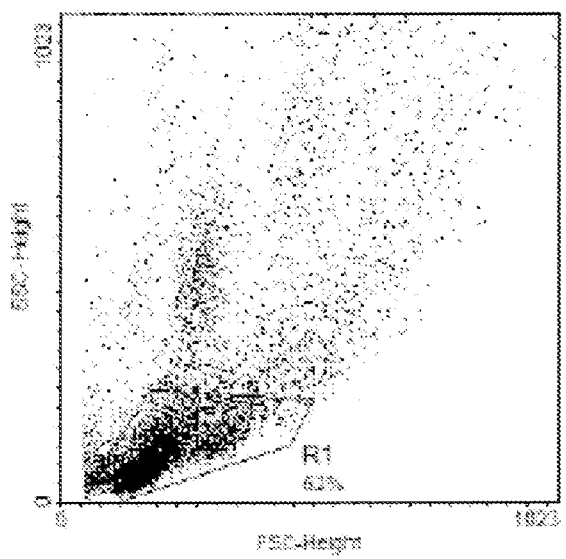
FIG. 7A shows a representative flow cytometry dot plot for forward scatter and side scatter of pooled PBMC from 12-week-old C57Bl/6 mice (n=3). The region as marking the monocytes (R1) is shown. Number indicates the proportion of PBMC in this region.
Figure 7B:
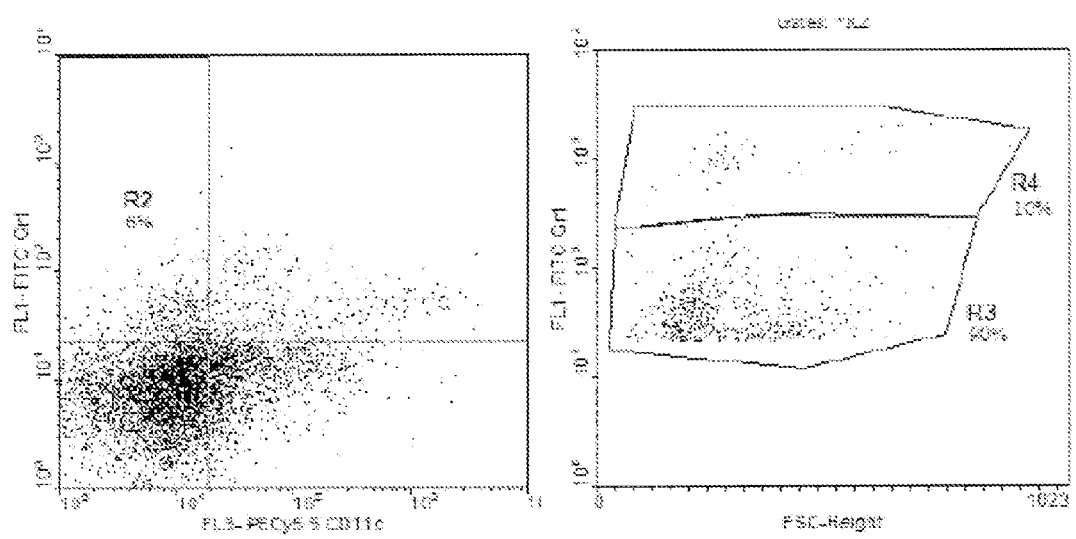
FIG. 7B (left panel) shows a representative flow cytometry of PBMC stained for Gr1 and CD11c. The R2 region represents Gr1+ CD11c– cells.
Figure 7C:
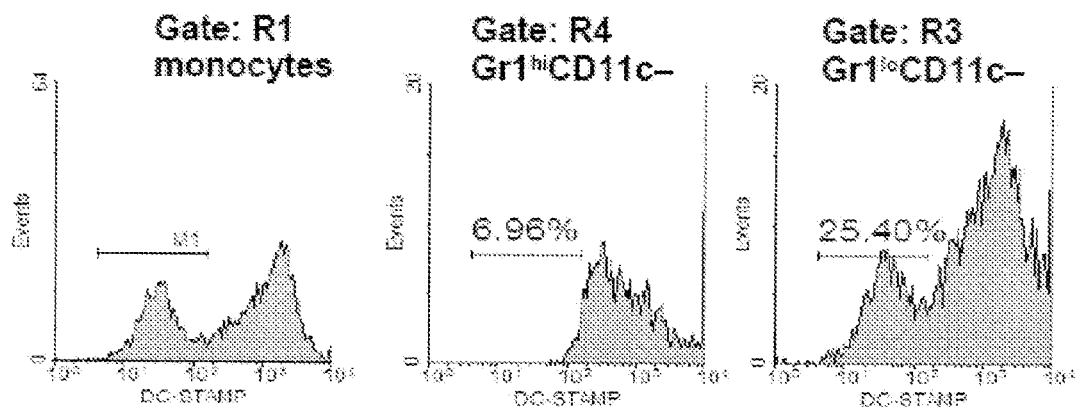
FIG. 7C shows representative flow cytometry histograms of PBMC from the R1 monocyte gate, the R3 Gr1$^{lo}$CD11c– gate or the R4 Gr1$^{hi}$CD11c– gate to indicate the presence or absence of DC-STAMP$^{lo}$ and DC-STAMP$^{hi}$ PBMC in the gated populations. Numbers represent the percentage of DC-STAMP$^{lo}$ cells.

Characteristics of the RC-STAMP$^{lo}$ and DC-STAMP$^{hi}$ cells induced by culture with RANKL. To characterize the newly identified DC-STAMP$^{lo}$ and DC-STAMP$^{hi}$ cells generated in culture with RANKL, a series of phenotyping analyses was performed. Using the forward-scatter parameter by flow cytometry, the RANKL-induced DC-STAMP$^{lo}$ cells were found to be larger than their DC-STAMP$^{hi}$ counterparts (FIG. 6B). Since the immunophenotyping analysis of CD11b+DC-STAMP expressing bone marrow cells revealed 13% of them to be CD11c+, whether this marker of mDC differed among the DC-STAMP$^{lo}$ and DC-STAMP$^{hi}$ cells after culture with IL-4+GM-CSF was examined. When these cells were sorted by FACS and cultured with IL-4+GM-CSF, it was found that they both had similar percentages of CD11c+ cells (87-88%). However, the DC-STAMP$^{hi}$ cells could generate a greater percentage of MHCII+CD11c+ cells (19%) compared to the DC-STAMP$^{lo}$ cells (9.7%) after the same period of time in culture (FIG. 6C). The immunophenotyping analysis of CD11b+DC-STAMP expressing bone marrow cells also revealed a high percentage of Gr1+ cells among this population. This is of note because a recent paper on the role of DC-STAMP in myeloid differentiation into granulocytes and non-granulocytes showed that DC-STAMP expression was associated with the non-granulocytic branch of myeloid cells (Eleveld-Trancikova et al., Leukemia 22:455-9 (2008)). Cells were compared based on whether they were Gr1$^{hi}$CD11c- or Gr1$^{hi}$CD11c-. It was found that DC-STAMP-GFP fusion protein expression allowed growth of Gr1$^{lo}$CD11c- cells but inhibited growth of Gr1$^{hi}$CD11c- cells. It has also been reported that ex-vivo culture of peripheral blood Gr1$^{lo}$ cells with RANKL and M-CSF can give rise to OC (Yao et al., J. Biol. Chem. 281:11846-55 (2006)). To see the expression pattern of surface DC-STAMP in these cells, peripheral blood cells were gated on the monocyte region as described previously (Sunderkotter et al., J. Immunol. 172:4410-7 (2004)), and also on gates for Gr1$^{lo}$ CD11c- cells and Gr1$^{hi}$CD11c- cells (FIGS. 7A and 7B). The cells in the monocyte gate showed both a DC-STAMP$^{lo}$ and DC-STAMP$^{hi}$ population. The majority of the Gr1$^{hi}$CD11c- cells were DC-STAMP$^{hi}$ with only about 7% being DC-STAMP$^{lo}$. In contrast, the Gr1$^{lo}$CD11c- population exhibited both DC-STAMP$^{hi}$ and DC-STAMP$^{lo}$ cells (FIG. 7C).

Figure 8A:
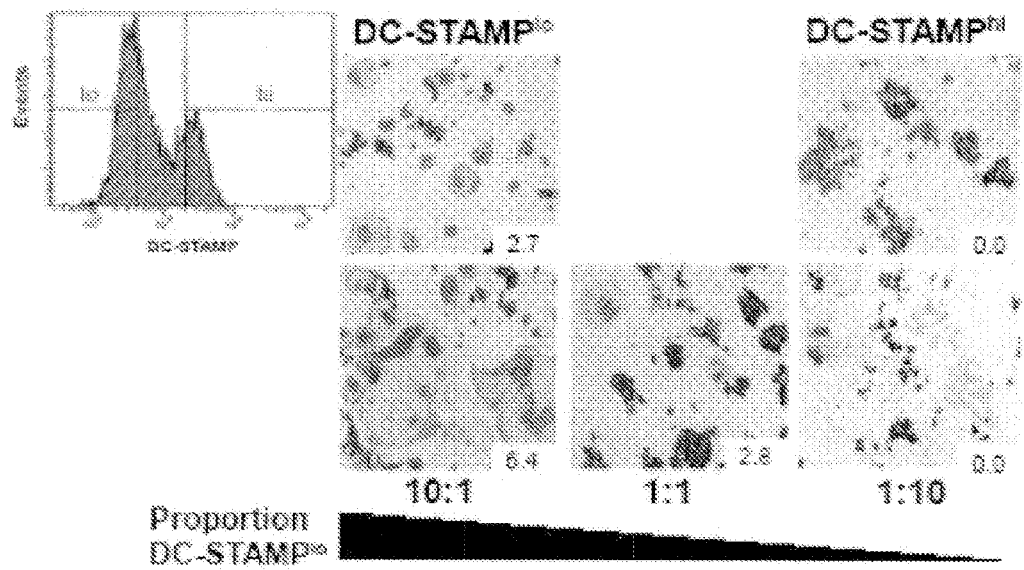
FIG. 8A shows RANKL-induced DC-STAMP$^{lo}$ and DC-STAMP$^{hi}$ RAW 264.7 cells were sorted based on surface DC-STAMP expression as indicated and recultured with RANKL for 3 more days either as homogeneous (DC-STAMP$^{lo}$ or DC-STAMP$^{hi}$) populations or mixed populations at ratios of 10:1, 1:1, or 1:10 DC-STAMP$^{lo}$:DC-STAMP$^{hi}$. Representative photographs are shown of the TRAP-stained cultures to demonstrate the relative osteoclastogenic potential of the different culture conditions. Numbers indicate the average area of the TRAP+ multinucleated cells and is reported in mm$^2$.

RANKL induces DC-STAMP$^{lo}$ and DC-STAMP$^{hi}$ cells which show different osteoclastogenic potential. The unexpected observation of the RANKL-induced surface DC-STAMP$^{hi}$ and RANKL-induced surface DC-STAMP$^{lo}$ populations prompted an investigation into the possibility of differential osteoclastogenic capability of these two groups. To determine whether there was a difference in the ability of the RANKL-induced DC-STAMP high and low populations to generate OC, RAW 264.7 cells were cultured with RANKL for 3 days to generate the two populations. TRAP staining following 3-day RANKL exposure after sorting revealed that TRAP+ multinucleated OC only formed when the RANKL-induced DC-STAMP$^{lo}$ population was present in culture. RANKL-induced DC-STAMP$^{lo}$ cells cultured alone had a mean OC area of 2.7±0.4 mm$^2$ while culture of RANKL-induced DC-STAMP$^{hi}$ cells alone yielded no TRAP+ multinucleated OC. A 1:1 culture ratio of RANKL-induced DC-STAMP$^{lo}$ to RANKL-induced DC-STAMP$^{hi}$ resulted in a mean OC area of 2.8±1.4 mm$^2$. A 10:1 culture ratio with the RANKL-induced DC-STAMP$^{lo}$ cells in excess resulted in a mean OC area of 5.8±0.6 mm$^2$ while having the RANKL-induced DC-STAMP$^{hi}$ cells in excess at a 10:1 ratio over the RANKL-induced DC-STAMP$^{lo}$ cells did not yield any large, multinucleated, TRAP+ OC (FIG. 8A).

Figure 8B:
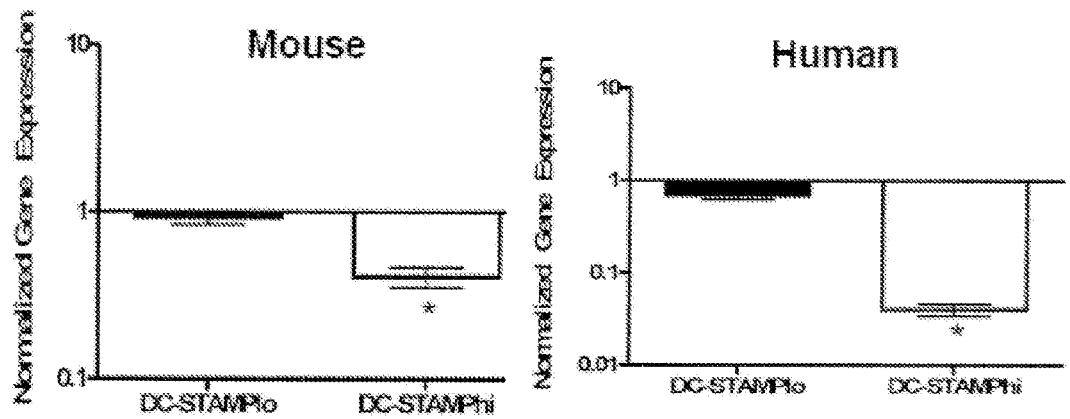
FIG. 8B (left panel) shows a bar graph demonstrating the relative DC-STAMP mRNA fold change in the murine RAW 264.7 RANKL-induced DC-STAMP$^{lo}$ (black bar) and DC-STAMP$^{hi}$ (white bar) cells.

RANKL-induced DC-STAMP$^{lo}$ OCPs express higher levels of OC marker and fusion-related genes. To explain the finding that RANKL-induced DC-STAMP$^{lo}$ OCP are better able to form TRAP+ multinucleated cells compared to their RANKL-induced DC-STAMP$^{hi}$ counterparts, differences in the expression of OCP markers between the two populations were examined. If the RANKL-induced DC-STAMP$^{lo}$ cells are indeed the more osteoclastogenic OCP subset, then the cells would be anticipated to express more OC marker genes. Since DC-STAMP is essential to OC fusion, genes for proteins that mediate the fusion process were also candidates for examination of any differences in OCPs exhibiting a dichotomy in their DC-STAMP cell surface profiles (Chen et al., FEBS Lett. 581:2181-93 (2007)). Real-time quantitative RT-PCR showed that dc-stamp gene expression is significantly lower by 60% in the RANKL-induced DC-STAMP$^{hi}$ OCP compared to RANKL-induced DC-STAMP$^{lo}$ OCP (FIG. 8B).

Figure 8C:
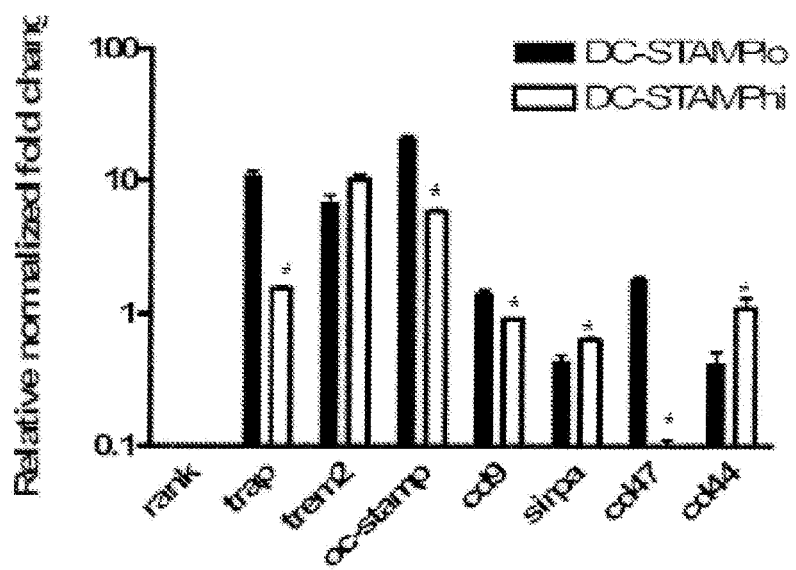
FIG. 8C shows a bar graph demonstrating relative mRNA fold change for OC marker genes or fusion-related genes in murine RAW 264.7 RANKL-induced DC-STAMP$^{lo}$ (black bars) and DC-STAMP$^{hi}$ (white bars) cells. Graphs are representative of experiments done in triplicate and data are normalized to β-actin. * P<0.05 vs. DC-STAMP$^{lo}$ gene expression levels.

Signaling through RANK induces dc-stamp expression in osteoclastogenesis, and TREM2 is a receptor upregulated by RANKL stimulation that associates with the adapter protein DAP12 to mediate multinucleation of OCP (Hehning et al., Sci. Signal 1:ra11 (2008)). Gene expression profiling for rank and trem2 showed no statistically significant difference between RANKL-induced DC-STAMP$^{hi}$ OCP and RANKL-induced DC-STAMP$^{lo}$ OCP. In fact, rank expression was decreased in both populations by an average of 98%. Interestingly, and in support of the in-vitro osteoclastogenesis results, trap expression was significantly greater by 11.3 fold in RANKL-induced DC-STAMP$^{lo}$ RAW 264.7 cells (FIG. 8C). The expression of oc-stamp, which was recently described as essential to OC differentiation (Yang et al., J. Cell. Physiol. 215:497-505 (2008)), was also examined. A 21-fold increase was found in the expression of oc-stamp in the RANKL-induced DC-STAMP$^{lo}$ OCP while only about a 5-fold increase in the RANKL-induced DC-STAMP$^{hi}$ group was found (FIG. 8C).

Important molecules involved in fusion during osteoclastogenesis, which include CD47, Sirpα, CD44, CD9, were chosen for analysis. The gene expression for these four fusion-related molecules was examined because of the open question of whether DC-STAMP was involved in the regulation of the expression of these factors (Chen et al., FEBS Lett. 581:2181-93 (2007)). Gene expression levels for cd9 and cd47 were significantly up-regulated 1.5- and 1.9-fold, respectively, in the RANKL-induced DC-STAMP$^{lo}$ population relative to RAW 264.7 cells cultured in plain media. These markers were down-regulated or unchanged in the RANKL-induced DC-STAMP$^{hi}$ cells. SirpαmRNA levels were significantly more upregulated in the RANKL-induced DC-STAMP$^{hi}$ population. This is of note because gene expression of its ligand, cd47, was higher in the DC-STAMP$^{lo}$ group. The cd44 gene expression level was significantly higher in RANKL-induced DC-STAMP$^{hi}$ cells (FIG. 8C).

Figures 9A, 9B:
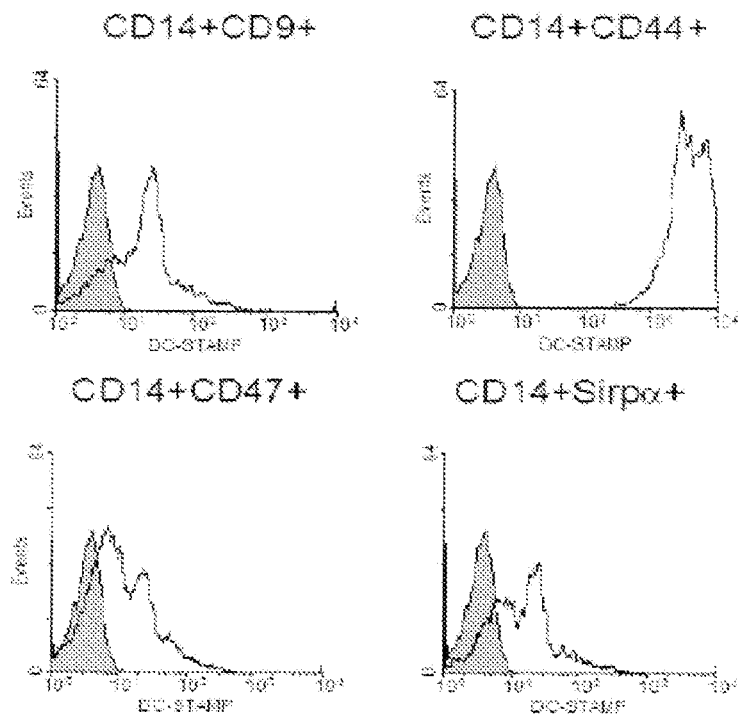
FIG. 9A shows a representative flow cytometry histogram of freshly-isolated PBMC from a healthy individual using fluorescently labeled specific antibodies to CD14, DC-STAMP and fusion-related proteins (CD9, CD44, CD47, and SIRPα).
FIG. 9B shows a table demonstrating the relative mRNA fold change for OC marker genes or fusion-related genes in human RANKL-induced DC-STAMP$^{lo}$ and DC-STAMP$^{hi}$ cells. The experiments were done in triplicate and data are normalized to β-actin.

Similar results were obtained in human CD14+ monocytes where flow cytometry demonstrated a DC-STAMP+ subset among CD14+CD9+ cells, CD14+CD44+ cells, CD14+CD47+ cells, and CD14+Sirpα+ cells (FIG. 9A). When CD14+ cells were cultured with RANKL and sorted into DC-STAMP$^{lo}$ and DC-STAMP$^{hi}$ groups, a significant 15-fold decrease in dc-stamp expression in DC-STAMP$^{hi}$ OCP was found compared to DC-STAMP$^{lo}$ OCP. Expression for trap was significantly higher by 2.3-fold in DC-STAMP$^{lo}$ OCP compared to DC-STAMP$^{hi}$ OCP. The expression of cd9, sirpα, and cd44 was also higher in the DC-STAMP$^{lo}$ OCP compared to the DC-STAMP$^{hi}$ OCP, while cd47 gene expression was higher in the DC-STAMP$^{hi}$ OCP (FIG. 9B). Again, the cd47-sirpαligand pair are differentially expressed between the two OCP as seen in RAW 264.7 cells.

Figure 10A:
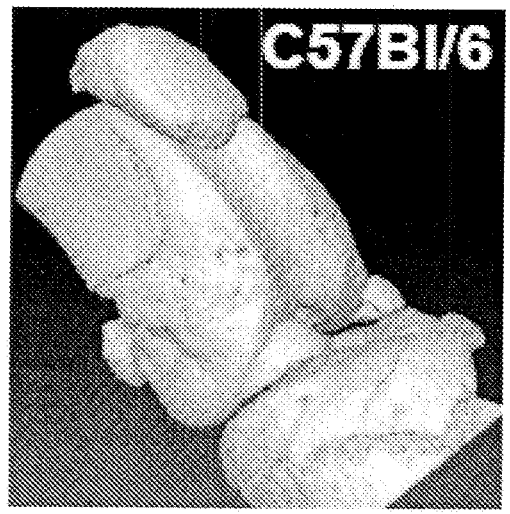
FIGS. 10A and 10B (left panels) show representative reconstructed 3D-CT images of the right knee joint from 20-week-old C57Bl/6 mice (A) or 20-week-old TNF-Tg mice (B) and associated flow cytometry dot plots (right panels) of pooled PBMC from the mice (n=3-5) stained with fluorescently labeled specific antibodies to CD11b and DC-STAMP. Numbers represent percentage of cells in the indicated quadrant.
Figure 10A:
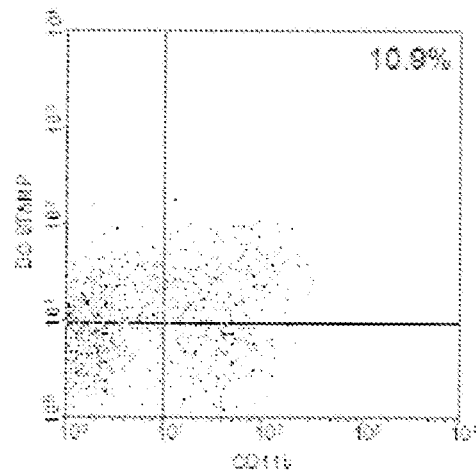
Figure 10B:
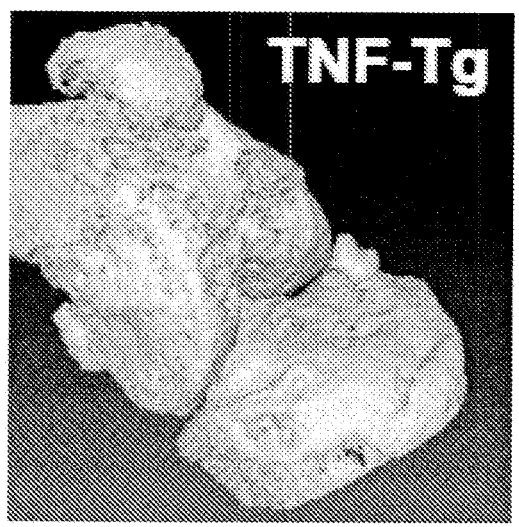
Figure 10B:
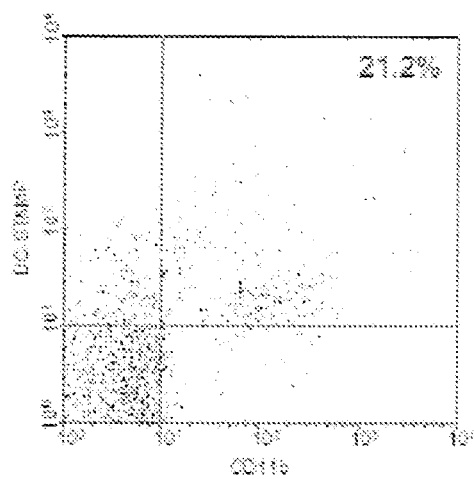
Figure 10C:
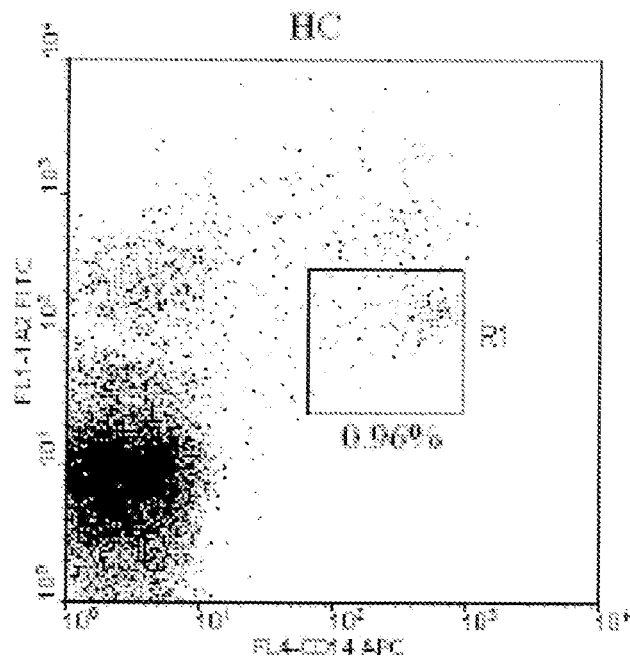
FIGS. 10C and 10D show representative flow cytometry dot plots of PBMC from a healthy individual (HC) (FIG. 10C) or an individual with RA (FIG. 10D) stained with fluorescently labeled specific antibodies to CD14 and DC-STAMP. Numbers represent percentage of cells in the indicated quadrants.
Figure 10D:
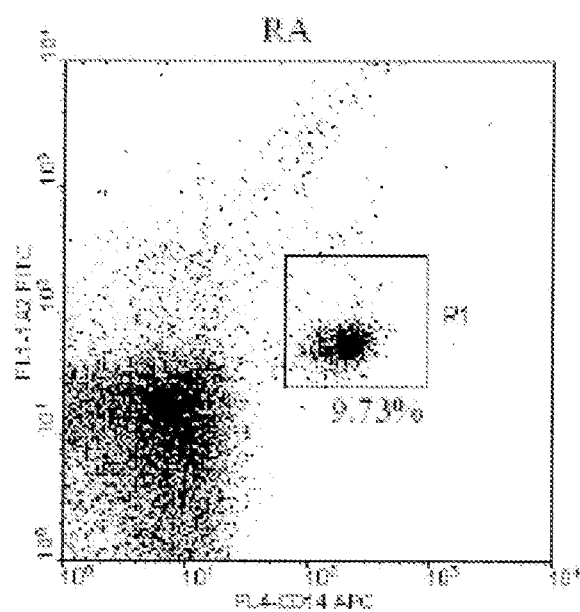
Figure 10E:
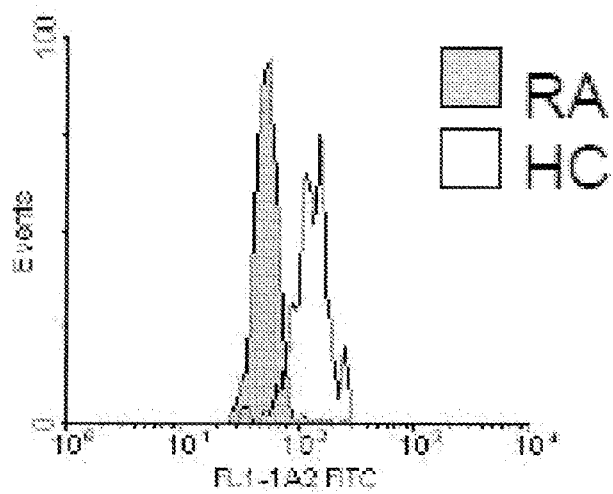
FIG. 10E shows representative flow cytometry histograms of PBMC in the regions boxed in C and D to show differences in the level of surface DC-STAMP.

Inflammatory erosive arthritis is associated with having a greater percentage of DC-STAMP expressing CD11b+ cells. To put these findings in the context of an IMID, DC-STAMP surface expression on CD11b+ cells was examined in the setting of inflammatory erosive arthritis where elevated numbers of OC result in bone destruction. To examine if there is a difference in the percentage of DC-STAMP-expressing CD11b+ OCP circulating in the PBMCs of arthritic mice compared to non-arthritic controls, micro-CT was performed on 20-week-old C57Bl/6 mice and age- and gender-matched TNF-Tg mice. Micro-CT analysis of the knee joint showed profound arthritic erosions present in the TNF-Tg mice while no erosions were observed in the C57Bl/6 mice (FIGS. 10A and 10B). When the percentage of circulating CD11b+ PBMC that were also expressing surface DC-STAMP was analyzed, it was found that there was about a 2-fold increase in this population among arthritic animals compared to non-arthritic animals (FIGS. 10A and 10B). The same flow cytometric analysis was performed on CD14+ human PBMC from a patient with RA and a healthy control. As in the TNF-Tg model of inflammatory erosive arthritis, the RA patient had a much greater percentage of CD14+ cells that also expressed surface DC-STAMP (FIGS. 10C and 10D). Furthermore, this DC-STAMP-expressing population was surface DC-STAMP$^{lo}$ compared to that in the healthy control which was surface DC-STAMP$^{hi}$ (FIG. 10E). This indicates that surface DC-STAMP expression can be a marker of OCP in peripheral blood and a higher percentage of circulating DC-STAMP-expressing OCP is associated with erosive disease.

IFN-α inhibits formation of the more osteoclastogenic DC-STAMP$^{lo}$ OCP and maintains high surface DC-STAMP levels in a stage-dependent manner. Non-erosive JA in SLE may be another characteristic of lupus mediated by the IFN-α gene signature. It has been shown that some cytokines only have an anti-osteoclastogenic effect in a stage-dependent manner (Huang et al., Arthritis Res. Ther. 5:R49-59 (2003), Sato et al., J. Exp. Med. 203:2673-82 (2006)). That is, the effect may depend on whether the cell is an early OCP (pre-RANKL exposure) or a later-stage OCP (post-RANKL).

Figure 11A:
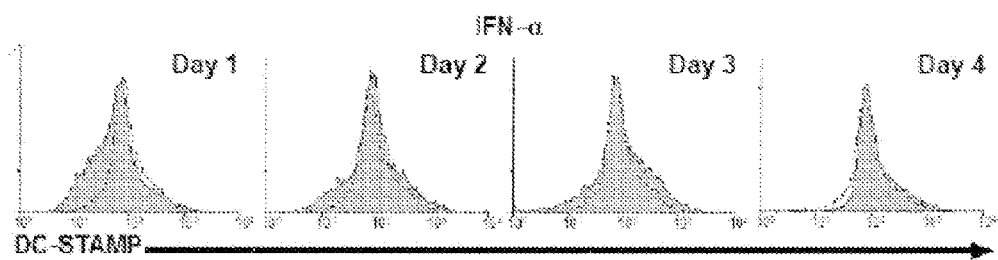
FIG. 11A shows a representative flow cytometry histogram of RAW 264.7 cells that were cultured for 1, 2, 3, or 4 days with IFN-α and stained with fluorescently labeled antibody to DC-STAMP for flow cytometry. Flow cytometry histograms representative of >3 experiments show the DC-STAMP surface expression pattern for each day (solid grey histogram) and for untreated cells (dotted histogram).
Figure 11B:
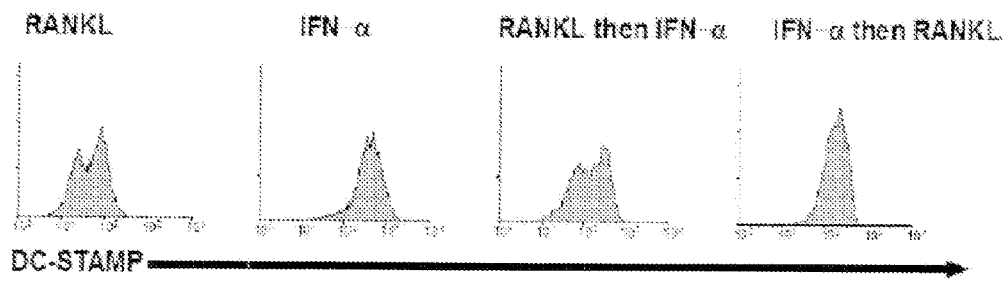
FIG. 11B shows a representative flow cytometry histogram as described in (A) on RAW 264.7 cells cultured for 3 days with RANKL, RANKL before IFN-α, or IFN-α before RANKL. Representative histograms show the DC-STAMP surface expression pattern for each culture condition to reveal the stage-dependent effect of IFN-α exposure.
Figure 11C:
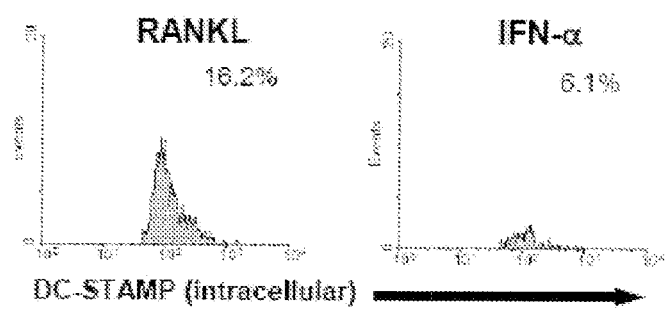
FIG. 11C shows a representative intracellular flow cytometry histogram performed using a fluorescently labeled antibody to DC-STAMP on cells treated with either RANKL or IFN-α for 3 days.

The effects of OCP exposure to IFN-α on the development of the DC-STAMP$^{lo}$ population were assessed. In contrast to the development of a DC-STAMP$^{lo}$ population as seen with RANKL culture, IFN-α culture of RAW 264.7 cells over 4 days did not result in a drop in DC-STAMP surface expression (FIG. 11A). When RAW 264.7 cells were pre-cultured with RANKL for 48 hours followed by exposure to IFN-α, a DC-STAMP$^{lo}$ and a DC-STAMP$^{hi}$ population were observed as in the RANKL-only culture group. In contrast, the RANKL induction of two DC-STAMP populations was suppressed by pre-culture of the cells with IFN-α for 48 hours followed by RANKL exposure (FIG. 11B). Intracellular flow cytometry showed that the percentage of cells expressing internal DC-STAMP was higher with 3 days of RANKL culture (16%) than with IFN-α (6%) (FIG. 11C). Thus, IFN-α can to prevent the formation of the DC-STAMP$^{lo}$ OCPs which are more osteoclastogenic and this is dependent on the OCPs encountering IFN-α before RANKL.

Figure 11D:
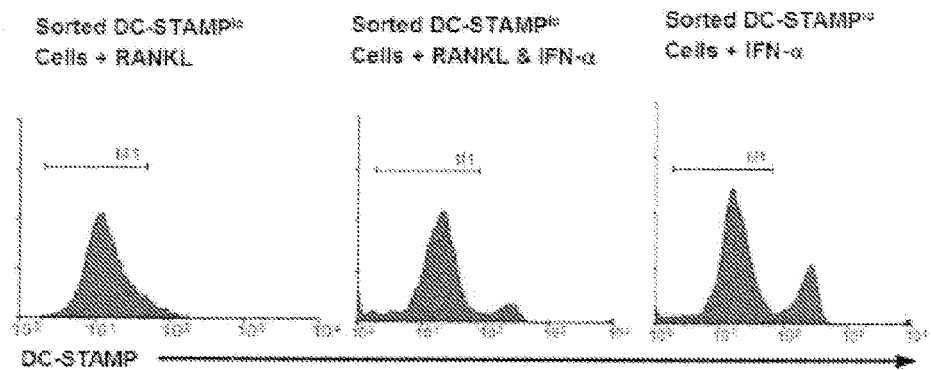
FIG. 11D shows representative flow cytometry for surface DC-STAMP on sorted RANKL-induced DC-STAMP$^{lo}$ cells re-cultured for 3 days with RANKL, RANKL and IFN-α, or IFN-α alone.

Whether the RANKL-induced DC-STAMP$^{lo}$ OCP could be affected by IFN-αadministration was then examined. Surprisingly, IFN-α culture of RANKL-induced DC-STAMP$^{lo}$ OCP resulted in the development of a DC-STAMP$^{hi}$ subset of cells. The ability of IFN-α to generate this DC-STAMP$^{hi}$ population from a sorted DC-STAMP$^{lo}$ group was mitigated by the simultaneous culture of the cells with RANKL and IFN-α (FIG. 11D).

Figure 11E:
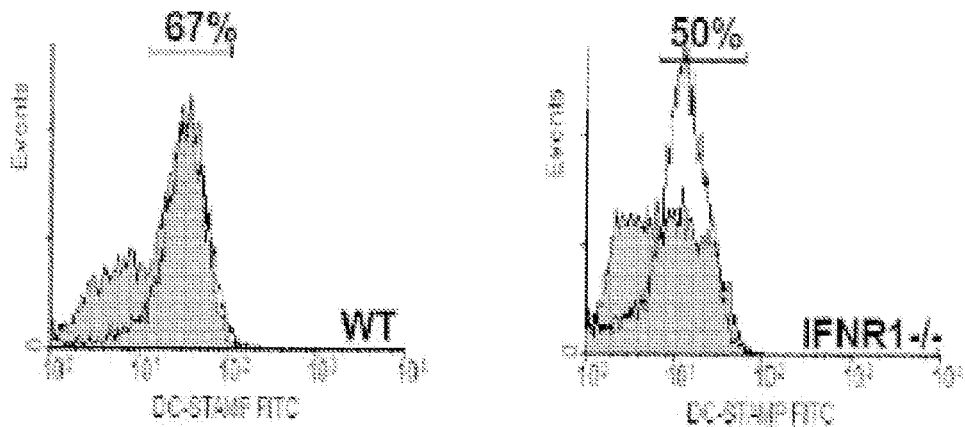
FIG. 11E shows representative flow cytometry for surface DC-STAMP on bone marrow macrophages from WT C57Bl/6 or IFNR1−/− mice cultured with RANKL for 4 days. Numbers indicate percentage of cells in the indicated DC-STAMP$^{lo}$ region.

RANKL induced DC-STAMP$^{lo}$ cells develop faster from IFNR1$^{-/-}$ OCP compared to WT OCP. Seeing these effects of IFN-α, the expression profile of DC-STAMP where IFN-α signaling is deficient was sought to be determined. IFNR1$^{-/-}$ mice exhibit generalized osteopenia as a result of elevated OC numbers (Takayanagi et al., Nature 416:744-9 (2002)). In contrast to the IFN-α treated OCP, OCP from IFNR1$^{-/-}$ mice developed a DC-STAMP$^{lo}$ population in response to RANKL. Interestingly, the development of this population occurred faster in IFNR1$^{-/-}$ mice compared to WT mice. By day 4 of culture, only ⅓ of WT OCP had become DC-STAMP$^{lo}$ in response to RANKL compared to 50% in the IFNR1$^{-/-}$ mice (FIG. 11E).

Figure 12A:
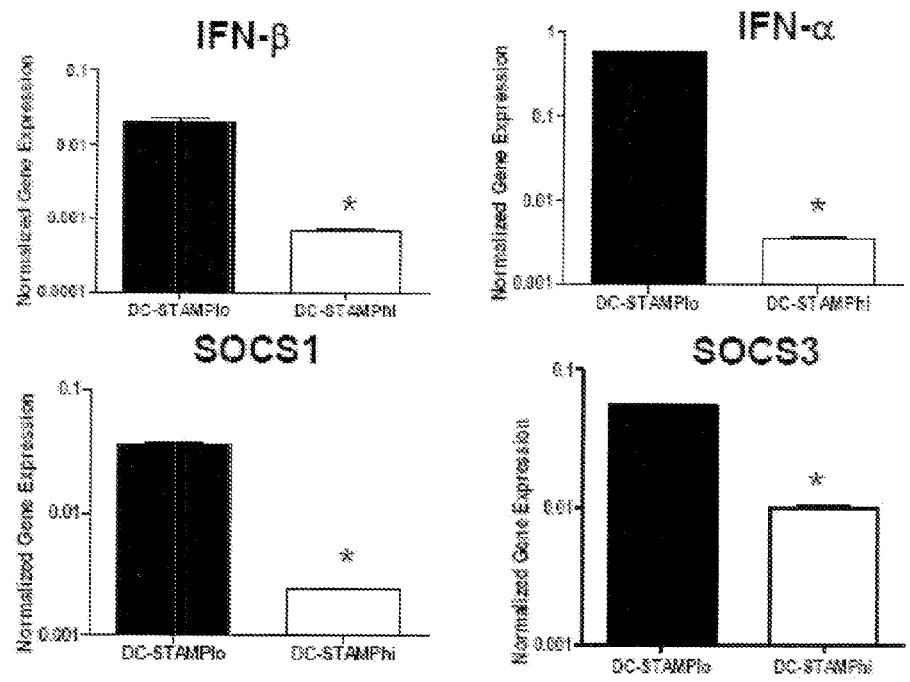
FIG. 12A shows bar graphs demonstrating the relative mRNA fold change (±SEM) for type I IFNs and SOCS1 and SOCS3 which counteract the effects of the type I IFNs in FACS sorted RANKL-induced DC-STAMP$^{lo}$ OCP (black bars) and DC-STAMP$^{hi}$ OCP (white bars). Graphs are representative of experiments done in triplicate and data are normalized to β-actin. *P<0.05 versus DC-STAMP$^{lo}$.
Figure 12B:
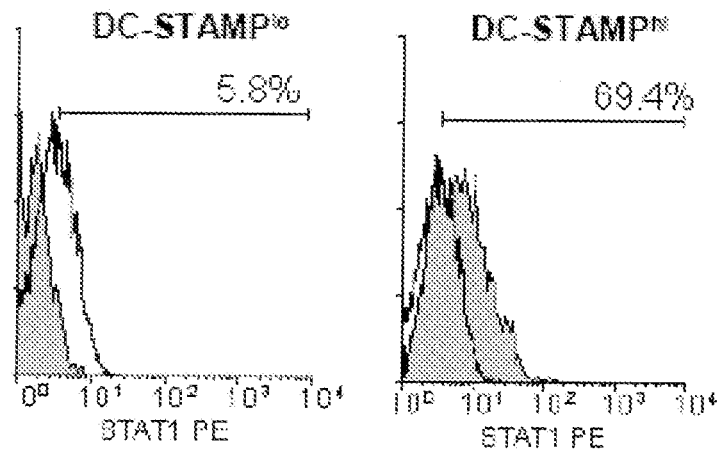
FIG. 12B shows representative flow cytometry histograms demonstrating intracellular pSTAT1 in RANKL-induced DC-STAMP$^{lo}$ and DC-STAMP$^{hi}$ OCP from C57Bl/6 bone marrow macrophages after 4 days of culture with RANKL (solid grey histograms) compared to bone marrow macrophages pre-RANKL exposure (black outlined histogram). Numbers represent the percentage of cells in the indicated regions.

RANKL-induced DC-STAMP$^{lo}$ OCP have greater IFN-α, SOCS1, and SOCS3 gene expression and lower pSTAT1 compared to RANKL-induced DC-STAMP$^{hi}$ OCP. Following from the work that identified IFN-β production by OCP were studies showing that SOCS1 and SOCS3 could counteract the inhibitory role of IFN-β during osteoclastogenesis (Hayashi et al., J. Biol. Chem. 277:27880-6 (2002)). Therefore, whether heterogeneity existed in the expression levels for IFN-β, IFN-α, SOCS1 and SOCS3 genes in RANKL-induced DC-STAMP$^{lo}$ versus DC-STAMP$^{hi}$ cells was examined. Real-time quantitative RT-PCR revealed significantly higher gene expression levels for these four genes in the more osteoclastogenic RANKL-induced DC-STAMP$^{lo}$ OCP compared to the RANKL-induced DC-STAMP$^{hi}$ OCP (FIG. 12A). When pSTAT1 levels were compared, a higher percentage (69%) of RANKL-induced DC-STAMP$^{hi}$ OCP expressed pSTAT1 at a level higher than that seen in bone marrow macrophages prior to RANKL exposure. In contrast, a lower percentage (6%) of RANKL-induced DC-STAMP$^{lo}$ OCP showed evidence of STAT1 phosphorylation (FIG. 12B).

Figure 12C:
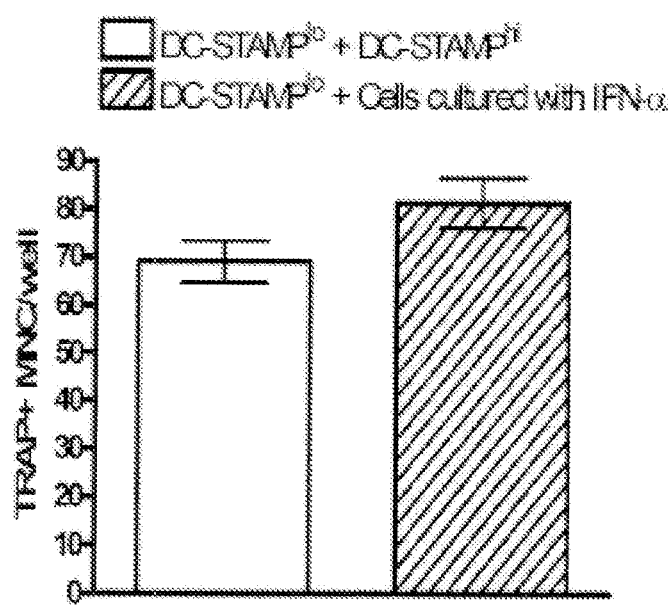
FIG. 12C shows a bar graph demonstrating either FACS sorted RANKL-induced DC-STAMP$^{lo}$ and DC-STAMP$^{hi}$ cells or FACS sorted RANKL-induced DC-STAMP$^{lo}$ and RAW 264.7 cells cultured with IFN-α for 3 days were co-cultured for 3 additional days with RANKL. The average number of TRAP+ multinucleated cells per well±SEM (n=4) was quantified for the RANKL-induced DC-STAMP$^{lo}$+DC-STAMP$^{hi}$ co-culture (white bar) or the RANKL-induced DC-STAMP$^{lo}$+ cells cultured with IFN-α (hatched bar).

Co-culture of RANKL-induced DC-STAMP$^{lo}$ cells with cells pre-treated with IFN-α results in TRAP+ multinucleated cells. Differential expression of type I interferon between RANKL-induced DC-STAMP$^{lo}$ and RANKL-induced DC-STAMP$^{hi}$ OCP was observed. Fusion-related gene expression was reduced in both RANKL-induced DC-STAMP$^{hi}$ cells and cells treated with IFN-α. Whether DC-STAMP$^{lo}$ cells could fuse with IFN-α treated cells as they do with DC-STAMP$^{hi}$ cells was examined. After three days of culture with RANKL, TRAP+ multinucleated cells were observed in co-culture of sorted DC-STAMP$^{lo}$ OCP with cells that had been pretreated with IFN-α. The average number of TRAP+ multinucleated cells/well was comparable between co-culture of DC-STAMP$^{lo}$ and DC-STAMP$^{hi}$ OCP and co-culture of DC-STAMP$^{lo}$ OCP and IFN-α pretreated cells (FIG. 12C).

Figure 13A:
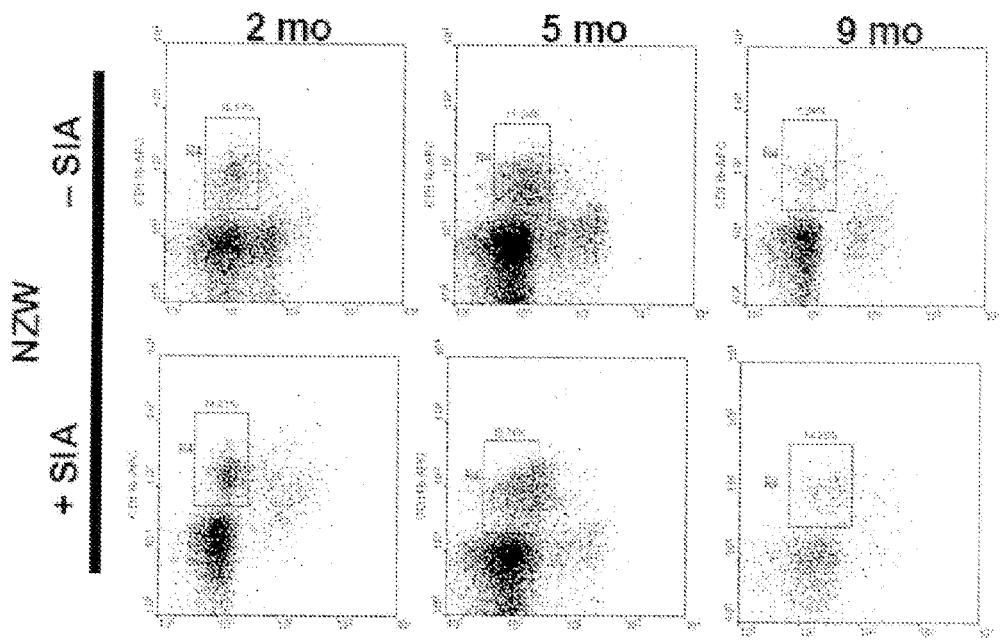
FIGS. 13A-13C show representative flow cytometry dot plots of blood that was pooled from the 2-, 5-, and 9-month-old NZW and NZB× NZW F1 mice (A, B), and the NZW mice treated with Ad-IFN-α and SIA (C). PBMC were stained with fluorescently labeled antibodies specific for CD11b and DC-STAMP, and analyzed by flow cytometry as described in Methods. Representative dot plots are shown to highlight the percentage of CD11b+DC-STAMP$^{lo}$ PBMC in the indicated boxed regions.
Figure 13B:
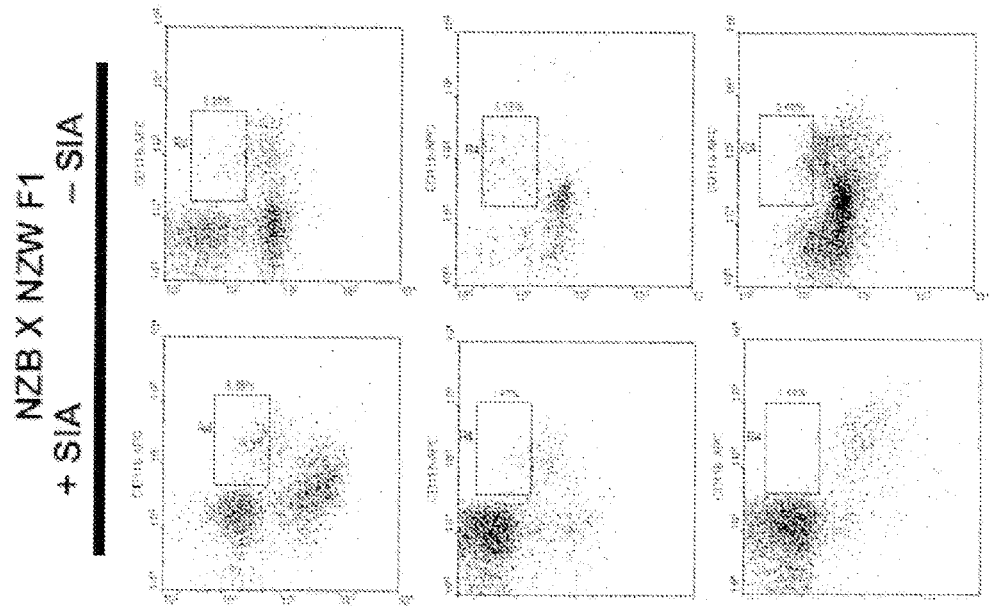
Figure 13C:
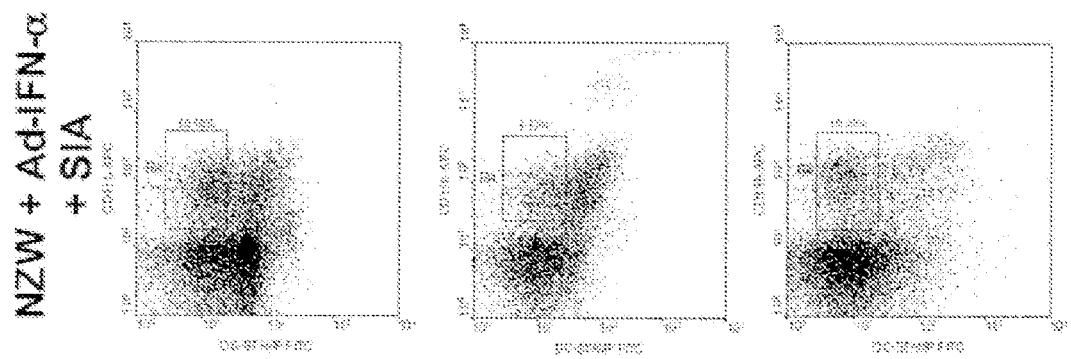
Figure 14A:
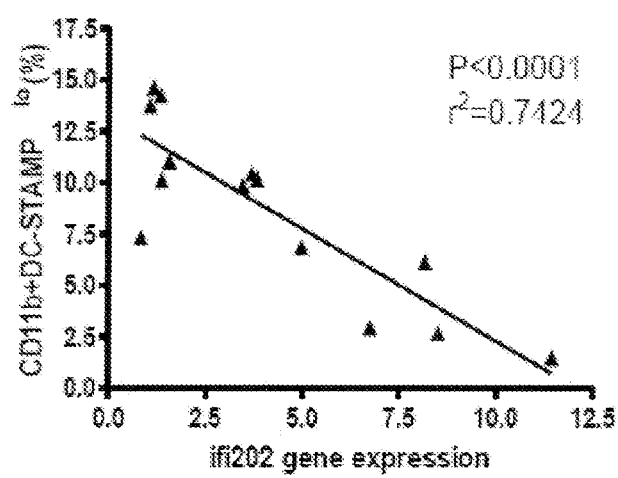
FIG. 14A shows a graph demonstrating a linear regression analysis of percentage of CD11b+DC-STAMP$^{lo}$ PBMC and ifi202 gene expression data.
Figure 14B:
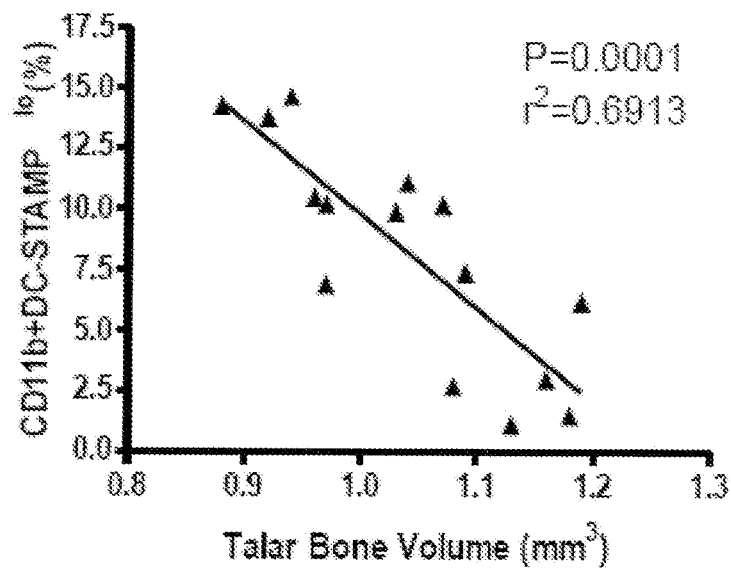
FIG. 14B shows a graph demonstrating a linear regression analysis of percentage of CD11b+DC-STAMP$^{lo}$ PBMC and talar bone volume. Individual points represent mean value for 3-5 mice.

NZBxNZW F1 mice with SLE-like disease and NZW mice treated with Ad-IFN-α have fewer DC-STAMP$^{lo}$ PBMCs and fewer erosions in the setting of inflammatory arthritis. To see if the findings of the effect of IFN-α on the development of the more osteoclastogenic DC-STAMP$^{lo}$ cells could explain nonerosive arthritis in SLE, the development of DC-STAMP$^{lo}$ cells in mice with SLE-like disease was examined. The NZBx NZW F1 model is an established murine model of SLE and has been found to have evidence of elevated IFN-α-inducible-ifi202 gene expression, which is a marker of SLE susceptibility (Rozzo et al., Immunity 15:435-43 (2001), Santiago-Raber et al., J. Exp. Med. 197:777-88 (2003)). The K/BxN serum transfer model was used to induce arthritis (SIA) in these animals and NZW (non-SLE) controls. Bone erosion monitored by talar bone volume measurements via micro-CT showed that NZW mice developed bone erosions in response to SIA. In contrast, NZBxNZW F1 mice with disease markers of SLE, like proteinuria and high titers of anti-dsDNA autoantibodies, did not exhibit bone loss with SIA. When CD11b+ OCP were examined for DC-STAMP expression, it was found that arthritogenic serum induced a greater DC-STAMP$^{lo}$ population in NZW mice (FIG. 13A). In contrast, lower levels of DC-STAMP$^{lo}$ cells were found in the NZBxNZW F1 mice, and this percentage did not increase with SIA (FIG. 13B). To examine whether this observation was a result of elevated IFN-α, NZW mice were pretreated with Ad-IFN-α and then induced SIA (FIG. 13C). Bone erosion was less pronounced in the Ad-IFN-α treated mice in the setting of SIA compared to NZW mice not treated with Ad-IFN-α. Interestingly, the CD11b+DC-STAMP$^{hi}$ population was elevated in both NZBxNZW F1 mice and NZW mice treated with Ad-IFN-α (FIGS. 13B and 13C). Linear regression analyses revealed highly significant inverse correlations between the percentage of CD11b+DC-STAMP$^{lo}$ cells and expression of the IFN-α-inducible ifi202 gene (P<0.0001) as well as between CD11b+DC-STAMP$^{lo}$ cells and bone volume (P=0.0001). Thus, the greater the ifi202 gene expression, the lower the percentage of CD11b+DC-STAMP$^{lo}$ PBMCs, and the greater the percentage of CD11b+DC-STAMP$^{lo}$ cells, the lower the bone volume (FIGS. 14A and 14B).

Example 2

Regulation of Human Osteoclast Development by Dendritic Cell-Specific Transmembrane Protein (DC-STAMP)

General Methods.

Reagents and antibodies. RANKL and MCSF were purchased from the R&D systems (Minneapolis, Minn.). Defined Fetal Bovine Serum (Hyclone) was used for all cell cultures. The DC-STAMP polyclonal antibody KR104 was purchased from CosmoBio Co., LTD. (Tokyo, Japan). Antibodies used were all purchased from BD Bioscience (San Jose, Calif.). 7-Amino-Actinomycin D (7-AAD) was included in all antibody cocktails as a vital dye to exclude dead cells. The antibody cocktail used for FIG. 19B included 1A2 (FITC), CD16 (PE), CD14 (APC), CD3 (Pacific Blue), CD19 (APC-Cy7) and 7-AAD. The other antibody cocktail used for FIG. 16C was composed of 1A2 (FITC), HLA-DR (PE-Texas Red), CD14 (Alexa Fluor 700), CD16 (Pacific Orange), CD15 (Pacific Blue), CD11b (APC-Cy7), CD11c (PE-Cy7), CD19 (PE), CD3 (APC), and 7-AAD. Cells were treated with 20% of Fc receptor blocker (Miltenyi Biotec; Bergisch Gladback, Germany) to block non-specific binding.

Production, purification and fluorochrome conjugation of monoclonal antibody 1A2. A synthetic DC-STAMP peptide corresponding to the fourth extracellular domain $^{447}$Glu-Val-His-Leu-Lys-Leu-His-Gly-Glu-Lys-Gln-Gly-Thr-Gln$^{460}$ (SEQ ID NO:1) (NCBI accession number Q9H295) was conjugated to KLH and was injected into mice for immunization using standard protocols (Yokoyama et al., Curr. Protoc. Immunol. Chap. 2, Unit 2.5 (2006)). Spleen cells from immunized mice were fused to myeloma tumor cells to generate a panel of hybridomas. Supernatants from each hybridoma were collected and their anti-DC-STAMP reactivity was screened by enzyme-linked immunosorbent assay (ETA). One monoclonal antibody (mAb) 1A2 was identified with specificity to DC-STAMP and used for all experiments. The FluoReporter FITC protein labeling kit (Molecular Probes; Invitrogen; Carlsbad, Calif.) was used to conjugate FITC to 1A2. Labeled antibodies were carefully titrated and their binding specificity to DC-STAMP was confirmed.

Cell isolation and monocyte enrichment. Peripheral blood mononuclear cells (PBMC) were separated from whole blood by Ficoll gradient as described previously (Chiu et al., Arthritis Res. Ther. 12:R14 (2010)). Human monocytes were enriched from whole peripheral blood by the Human Monocyte Enrichment Cocktail (StemCell technologies; Vancouver, BC, Canada) following the manufacturer's instructions.

Cell staining, sorting and FACS analysis. For sterile cell sorting, PBMC prepared from Ficoll gradient were resuspended in sterile PBS ($10 \times 10^6$ cells/ml) and incubated with 1A2-FITC for 20 minutes at room temperature. Cells were washed twice with PBS, resuspended in PBS ($5 \times 10^6$ cells/ml) and sterile sorted with the FACS Vantage sorter (Becton Dickinson Immunocytometry Systems; San Jose, Calif.). After sorting, the purity of cells was reexamined by flow cytometry and $1 \times 10^5$ cells were cultured in one well of a flat 96-well plate in triplicate with RANKL and M-CSF for 8 days. For flow cytometry analysis, cells were harvested, washed once with PBS, blocked with 5% normal mouse sera for 10 minutes at room temperature and stained with antibody for 20 minutes at 4° C. in the dark. Cells were thoroughly washed with PBS and fixed in 2% formaldehyde. FACS data were acquired using Canto or LSRII and analyzed using CellQuest (Becton Dickinson) or FlowJo (TreeStar; Ashland, Oreg.) software.

OC culture and TRAP staining. Purified PBMC or monocytes were cultured in RPMI (Gibco; Invitrogen; Carlsbad, Calif.), supplemented with 8% heat-inactivated fetal bovine serum (Hyclone; Thermo Scientific; Logan, Utah), 2 mM glutamine, 50 units/ml penicillin, 50 ug/ml streptomycin. RANKL (100 ng/ml) and CSF (25 ng/ml) were added to cell culture to stimulate OC generation. PBMC ($1 \times 10^5$ cells/ml) or monocytes ($1 \times 10^6$ cells/ml) per well were cultured in 96-well plates for 8 days in a humidified 37° C. incubator with 5% $CO_2$. Media were replenished every 2 days. On day 8, cells were fixed with 3% formaldehyde and stained for tartrate acid phosphatase (TRAP) (Sigma; St. Louis, Mo.). Cells were examined by light microscope and TRAP+ cells with three or more nuclei were counted as OC. For analysis of the 1A2 inhibitory effect on OC formation, 380 mg/ml 1A2 was constantly present in the cell culture.

Immunoprecipitation and western blot analysis. Human PBMC purified from Ficoll gradient were lysed using the CytoBuster Protein Extraction Reagent (Novagen; EMD Chemicals; Darmstadt, Germany). For immunoprecipitation, cell lysates were pulled down by anti-DC-STAMP 1A2 or anti-CD16 3G8 using the immunoprecipitation kit (Invitrogen). Immunoprecipitates were subject to SDS-PAGE analysis on 4-12% Bis-Tris gradient gels, followed by wet-transfer blotting using PVDF membrane. The membrane was first probed with phosphotyrosine mAb 4G10 (Millipore), CD16 (BD Biosciences) mAb, or DC-STAMP mAb 1A2, followed by HRP-conjugated light chain specific secondary antibody. The HRP-conjugated light chain specific antibody (Jackson ImmunoResearch; West Grove, Pa.) was chosen as the secondary antibody to avoid heavy chain signal close to 50 kDa. Blots were developed with the SuperSignal West Pico or Femto chemiluminescent substrate kit (Pierce; Rockford, Ill.) and imaged on Kodak scientific films (Eastman Kodak; Rochester, N.Y.).

Immunofluorescence staining. Monocytes were enriched by the Monocyte Enrichment Cocktail (StemCell) and were cultured on glass slides in culture media with RANKL and M-CSF for 8 days. Cells were fixed in cold methanol at −20° C. for 10 minutes and washed with PBS. Cells were permeabilized and blocked with 0.1% saponin and 0.2% BSA/PBS for 15 minutes at room temperature. Fixed cells were then stained with rhodamine phalloidin (Molecular Probes), FITC-conjugated DC-STAMP 1A2 antibody and DAPI for 2 hours at room temperature, followed by an additional wash with 0.1% saponin and 0.2% BSA/PBS for 5 minutes. Slides were mounted in 90% glycerol and 10% 1M Tris (pH8). Images were taken using a Zeiss phase contrast fluorescence microscope. For immunohistochemical staining (FIG. 15C), PBMC were spun down and fixed in 10% NBF (Cardinal Health; Dublin, Ohio) for one hour. The cell pellet was gently dislodged from the centrifuge tube, poured through specimen paper, and placed into a histology cassette. The cassette was processed on a standard VIP tissue processor using a short routine cycle. The cell pellet was then embedded into paraffin. Serial sections were cut at 4-microns and mounted on glass slides. The paraffin section was dried at 60° C. for one hour, and de-paraffinized through two changes of xylene and graded alcohols. The slides were pre-treated with Target Retrieval Solution, pH 6 (Dako, Carpinteria, Calif.) for 20 minutes at 99° C. with a brief cool down period then washed several times in fresh 1× Wash Buffer (Dako). The slides were incubated with 1A2 or mouse IgG2a isotype control (BD Biosciences) at 1:1500 dilutions for 60 minutes at room temperature. Unbound antibodies were removed by several rinses. Staining was visualized by the Flex polymer based detection kit with DAB as a chromogen (Dako) and counterstained with Flex Hematoxylin (Dako).

Statistical analysis. The permutation test was employed with $10^5$ re-samplings for statistic analysis to evaluate the inhibitory effect of 1A2 on OC formation for FIG. 16D(c). The distribution of 4 DC-STAMP patterns between HC and PsA was analyzed by the Fisher's exact analysis for FIG. 17(B).

Results

Figure 15A:
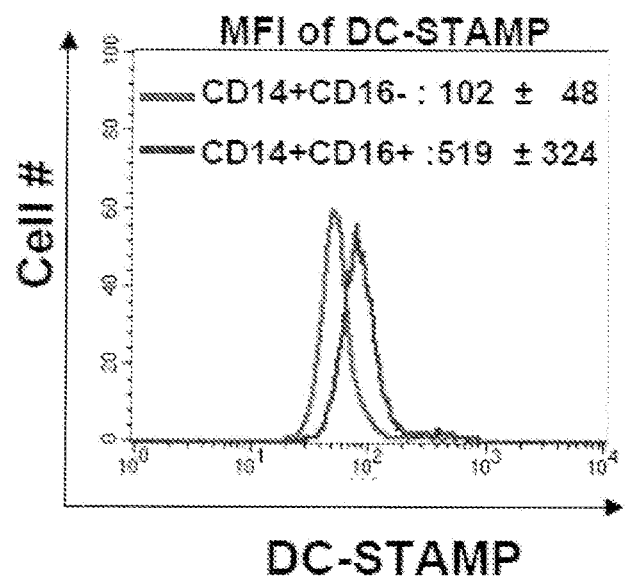
FIG. 15A is a graph demonstrating that there is a positive correlation between DC-STAMP and CD16 expression. Human CD14+CD16+ monocytes have a higher surface expression of DC-STAMP than CD14+CD16− cells. Human PBMC were purified by Ficoll gradient and stained with an antibody cocktail composed of 7-AAD, DC-STAMP and CD16 antibodies. The expression of DC-STAMP on CD14+CD16− and CD14+CD16+ cells were labeled in grey and black, respectively. The commercially available DC-STAMP polyclonal antibody KR104 was used for this analysis.

DC-STAMP is an ITIM-bearing protein. It has recently been shown that the CD14+CD16+ inflammatory monocyte subset is preferentially expanded in PsA patients with a condition associated with an elevated OCP frequency (Chiu et al., Arthritis Res. Ther. 12:R14 (2010). Based on this study, CD16 can serve as an OCP marker, but it lacks specificity. With an essential role of DC-STAMP in OC development, the relationship between the expression of DC-STAMP and CD16 was examined in order to identify an additional OCP marker that will increase specificity when combined with CD16. To this end, the surface expression of DC-STAMP was analyzed on CD14+CD16− and CD14+CD16+ monocytes with a commercially available anti-DC-STAMP polyclonal antibody KR1048 (FIG. 15A). The mean fluorescence intensity (MFI) of DC-STAMP on CD14+CD16+ monocytes was significantly greater than that on CD14+CD16− monocytes (519±324 vs. 102±48, n=10), which suggested a positive association between CD16 and DC-STAMP expression in fresh human monocytes (FIG. 15A).

CD16 bears an immunoreceptor tyrosine-based activation motif (ITAM) on the intracytoplasmic domain (Sandor et al., Immunol. Lett. 54:123-7 (1996)). The ITAM-mediated activation signal is often coupled with a counteracting inhibitory signal delivered by immunoreceptor tyrosine-based inhibitory motif (ITIM)-bearing receptor. An ITIM motif is a short peptide motif containing a consensus sequence (IN/L/S)-X-Y-X-X-(LN) where X denotes any amino acid (Nimmerjahn and Ravetch, Nat. Rev. Immunol. 8:34-47 (2008)). As shown in FIG. 15A, a positive correlation was observed between the surface expression of CD16 and DC-STAMP. This finding raised the possibility that DC-STAMP may have an ITIM-like motif able to counteract signals induced by ITAM on CD16. This speculation was based on the dynamic changes observed in CD16 and DC-STAMP surface expression during osteoclastogenesis in which the surface expression of CD16 increased over time, whereas DC-STAMP levels steadily declined (see below in FIG. 18A). To explore this possibility, the protein sequence of DC-STAMP was screened and a bona fide ITIM was identified, $^{407}$Ser-Phe-Tyr-Pro-Ser-Val$^{412}$ (SEQ ID NO:4), in the cytoplasmic domain of DC-STAMP.

Figure 15B:
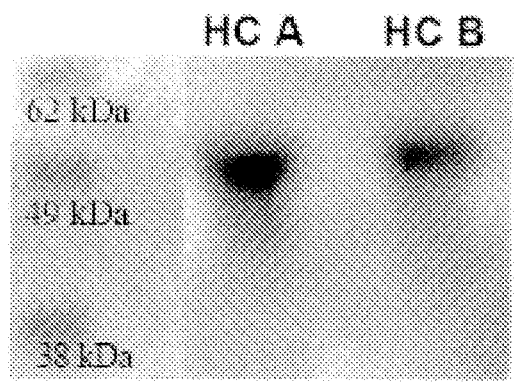
FIG. 15B is an image of a Western blot showing proteins from two healthy controls (HC A and HC B) were isolated, immunoprecipitated, separated by 10% gradient protein gel, and probed with the DC-STAMP mAb 1A2.

A novel monoclonal antibody 1A2 with anti-DC-STAMP specificity was established. No specific surface markers for OCP are currently available. Current methods of OCP quantification employ cell culture techniques, which are time-consuming, expensive and difficult to replicate. In addition to CD16, a potential OCP surface marker was recently identified (Chiu et al., Arthritis Res. Ther. 12:R14 (2010)). DC-STAMP was examined to determine if DC-STAMP was also expressed by OCP. To this end, as described above, a monoclonal antibody (mAb) against DC-STAMP was generated. The epitope ($^{447}$Glu-Val-His-Leu-Lys-Leu-His-Gly-Glu-Lys-Gln-Gly-Thr-Gln$^{460}$) (SEQ ID NO:1) used to generate the antibody is highly conserved between mice and humans and is located on the fourth extracellular domain of DC-STAMP. One clone, 1A2, with reactivity to DC-STAMP was identified by EIA from a panel of hybridomas, and the specificity of 1A2 was confirmed by western blot with murine cell lysates. To determine whether the 1A2 mAb can also recognize the human DC-STAMP protein, the protein lysates from monocytes were isolated from 2 healthy controls (HC), separated by SDS-PAGE, and probed by 1A2 on western blot. As shown in FIG. 15B, the 1A2 mAb recognized a single 53 kDa band specifically on western blot. These data demonstrated that 1A2 is a novel anti-DC-STAMP mAb that specifically recognizes an epitope common to both human and mouse DC-STAMP protein.

Figure 15C:
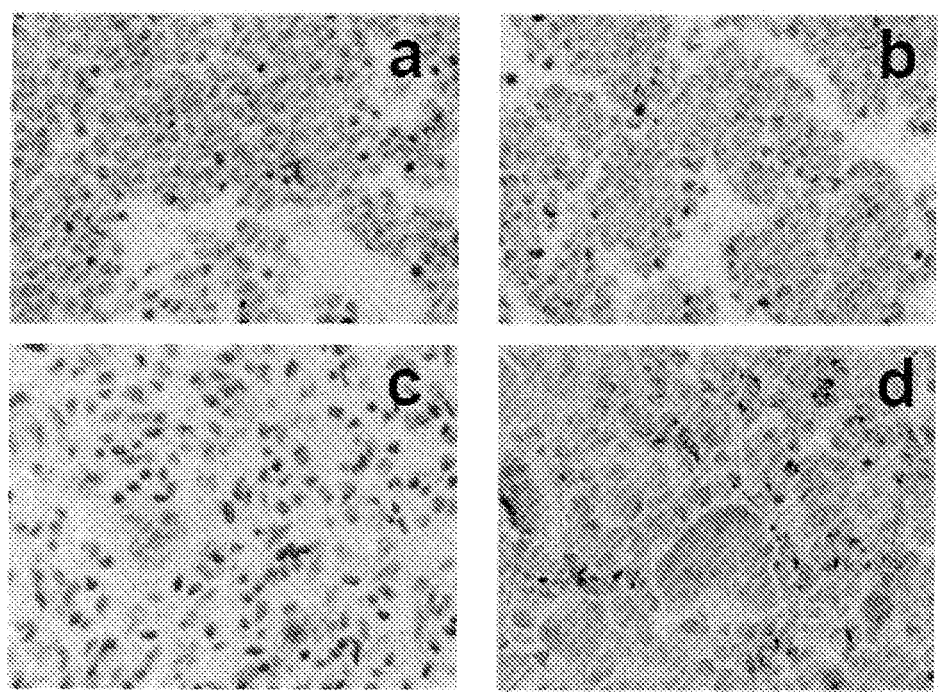
FIG. 15C shows images of DC-STAMP expression on human PBMC and giant cells (bone tumor) detected by immunohistochemical (IHC) staining using 1A2, (a) & (b). Human PBMC were purified by Ficoll gradient, embedded in paraffin for section, and stained with (a) mouse IgG2a isotype control, or (b) 1A2. Human biopsy samples collected from bone tumors were sectioned, and stained with (c) mouse IgG2a isotype control, or (d) 1A2. Both 1A2 and mouse IgG2a isotype control were diluted at 1:1500 for staining. The polarized expression of DC-STAMP in bone tumor cells was labeled by arrows.

Next, 1A2 was used to examine the expression of DC-STAMP on human PBMC by immunohistochemical (1HC) staining. A certain proportion of PBMC was bound by 1A2 (FIG. 15C(b)), suggesting the expression of DC-STAMP on these cells. Since DC-STAMP is also pivotal in the formation of giant cells, the expression of DC-STAMP on biopsy samples collected from human giant cells (tumor of bone) was examined. The expression of DC-STAMP on bone tumor cells was polarized as indicated by arrows shown in FIG. 15C(d). The control staining with mouse IgG2a is shown in FIGS. 15C(a) and 15C(c).

The DC-STAMP mAb 1A2 was sequenced according to known methods (Jarrin and Andrieux, Methods Mol. Biol. 96:21-8 (1999); Eswarakumar et al., Immunogenetics 46:249-50 (1997); Morrison, Curr. Protoc. Immunol. Chap. 10, Unit 10.25 (2001)). The light chain of the 1A2 mAb comprises the DNA sequence of SEQ ID NO:7 and the polypeptide sequence of SEQ ID NO:5. The heavy chain of the 1A2 mAb comprises the DNA sequence of SEQ ID NO:8 and the polypeptide sequence of SEQ ID NO:6.

Figure 15D:
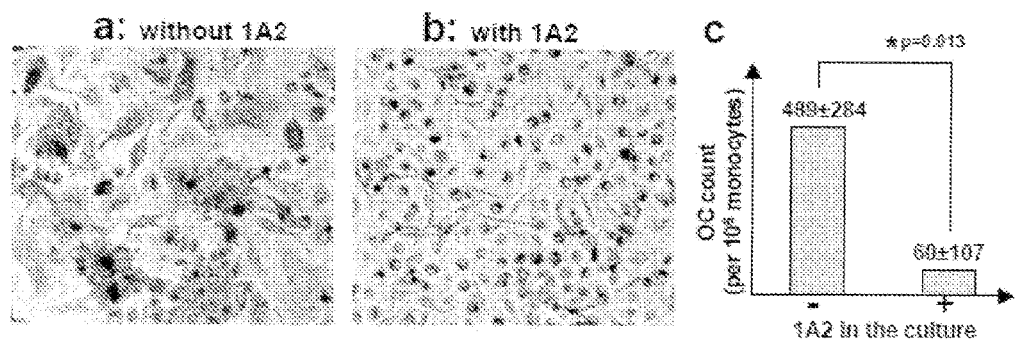
FIG. 15D shows the DC-STAMP mAb 1A2 was able to block OC formation in vitro. Enriched human monocytes were cultured in the absence (a) or presence (b) of 1A2 for 8 days and TRAP-stained for visualization and enumeration of OC.

The anti-DC-STAMP 1A2 mAb blocks OC formation in vitro. It was previously shown that anti-DC-STAMP polyclonal antibody KR104 inhibited osteoclastogenesis in RAW-D cells and bone marrow-derived multinucleated cells (MNCs) (Kukita et al., J. Exp. Med. 200:941-6 (2004)). Whether 1A2 can also block OC formation in human PBMC and monocyte cultures was examined. 1A2 was continuously present in OC culture and replenished after each medium exchange during 8-day OC culture. Interestingly, 1A2 blocked the formation of OC efficiently (FIG. 15D(a): without 1A2; FIG. 15D(b): with 1A2). 1A2 blocked OC formation in a dosage-dependent manner and was DC-STAMP-specific when compared to IgG2a isotype control. In the presence of 1A2, the majority of monocytes were arrested at the TRAP-positive pre-OC stage (FIG. 15D(b)). 1A2 also suppressed the formation of resorption pits on bone wafers. The inhibitory effect of 1A2 on OC formation in 6 subjects was summarized in Table 2. The presence of 1A2 in monocyte culture significantly inhibited OC formation. The average OC numbers derived from $10^6$ monocytes in the absence or presence of 1A2 are 489±284 and 61±107, respectively (p=0.013 by permutation test).

TABLE 2

The DC-STAMP mAb 1A2 had an inhibitory effect on OC formation.

| Subject[a] | Without 1A2[b] | With 1A2[b,c] |
|---|---|---|
| A | 125 | 0 |
| B | 740 | 0 |
| C | 500 | 15 |
| D | 155 | 80 |
| E | 745 | 0 |
| F | 670 | 270 |

Figure 16A:
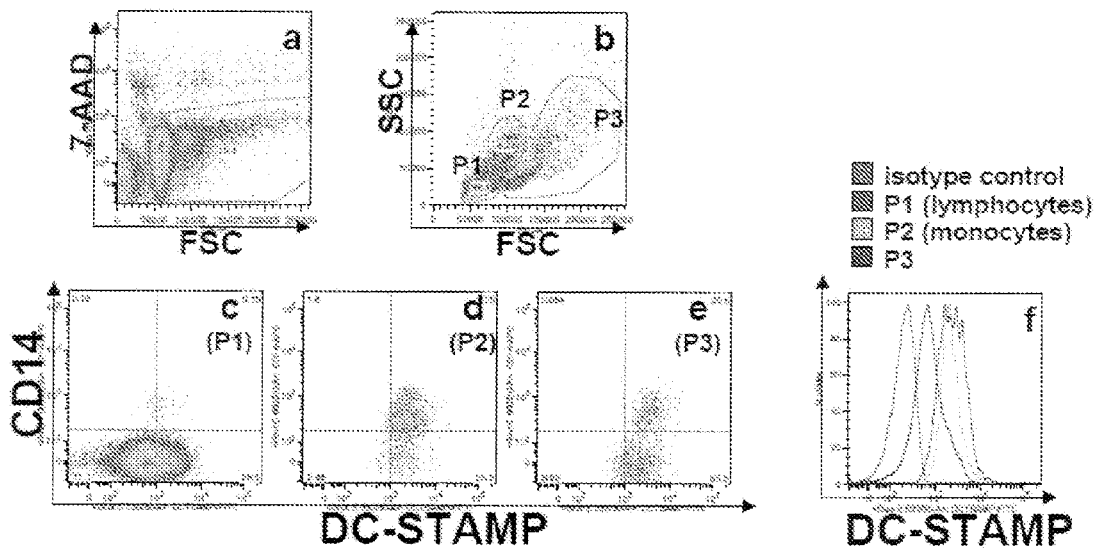
FIG. 16A shows an analysis of DC-STAMP expression on human PBMC. Human PBMC were purified from the whole blood by Ficoll gradient, subject to antibody staining and flow cytometry analysis. Human PBMC were stained with an antibody cocktail composed of 6 antibodies. Dead (7AAD+) cells were first excluded from our analysis (a); and live PBMC were gated based on cell size by FSC and cell granularity by SSC into 3 cell subsets (b) (P1, P2, P3). The expression of CD14 and DC-STAMP on the P1, P2 and P3 subset was shown in (c), (d) and (e), respectively. The surface expression of DC-STAMP in P1, P2, P3 gated cells (f). Data shown is representative of 4 HC and 4 PsA subjects.
Figure 16B:
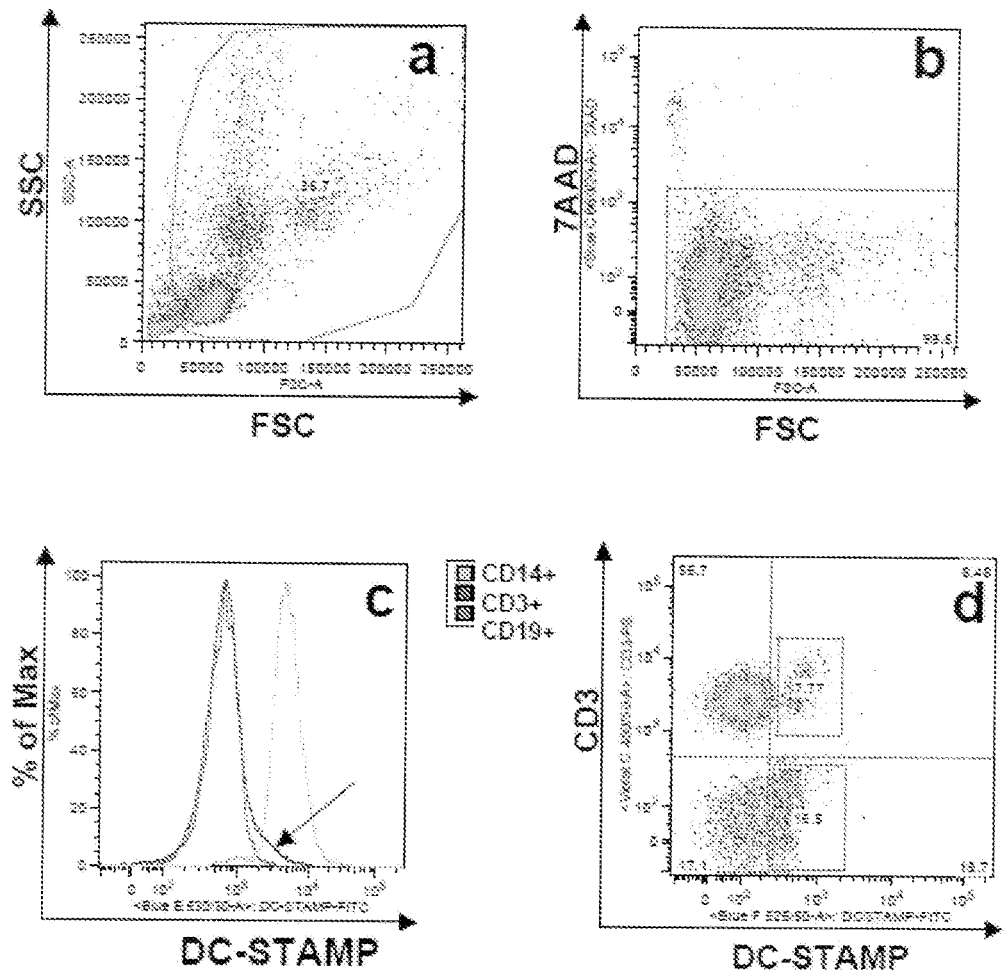
FIG. 16B shows that DC-STAMP is expressed on a small subset of CD3+ cells. Human PBMC were purified and stained with an antibody cocktail composed of 6 antibodies. PBMC were gated by FSC/SSC (a). Live cells were gated by 7AAD (b). Monocytes, T and B cells were identified by gating of CD14+, CD3+ and CD19+ cells, respectively (c). The histogram shows the overlay of DC-STAMP expression on CD14+ (light grey line), CD3+ (black line), and CD19+ (grey line) populations. A small percentage of CD3+ are DC-STAMP+ (indicated by arrow). The relative expression of DC-STAMP and CD3 on human PBMC is shown (d).
Figure 16C:
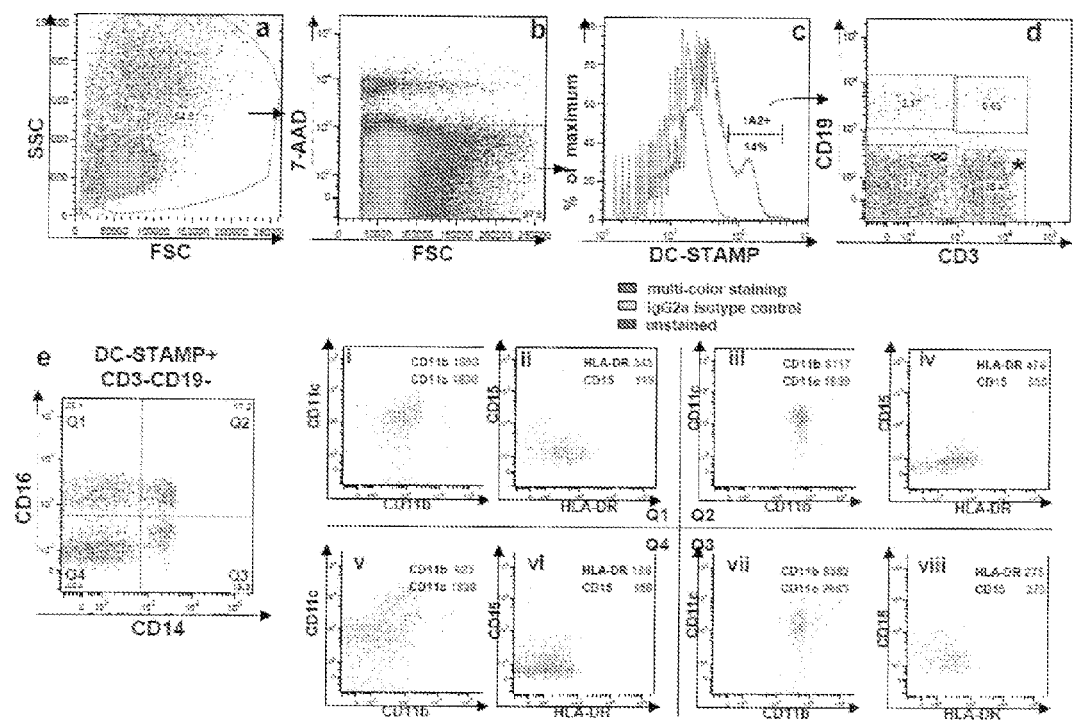
FIG. 16C shows the expression of DC-STAMP on human monocytes showed by the step-by-step gating strategies for analysis of human PBMC with an antibody cocktail composed of 10 antibodies. Total PBMC were gated on FSC and SSC (a); dead cells were excluded by 7AAD (b); live DC-STAMP+ cells were gated as 1A2+ (~14%) based on controls (c); 1A2+ cells were further classified into 4 subsets based on CD3 and CD19 expression (d). Two major 1A2+ cell populations, CD3−CD19− (31.9%) and CD3+CD19− (38.4%) were labeled by ∞ and *, respectively. The non-B, non-T, DC-STAMP+ cells (CD3−CD19−1A2+, indicated by ∞ in (d)) were further dissected into 4 subsets (Q1, Q2, Q3, Q4) by CD14 and CD16 expression (e). The expression of CD11b & CD11c (i, iii, v, vii) and HLA-DR & CD15 (ii, iv, vi, viii) on these 4 subsets were shown from (i) to (viii). Numbers in each dot plot represent the mean fluorescence intensity (MFI) of each individual marker. The experimental data is representative of 4 independent samples.

[a]HC, Ps, or PsA patients
[b]numbers of OC derived from 106 CD14+ cells
[c]constant presence of 1A2 in the culture at the concentration of 380 µg/µl Monocytes are the majority of DC-STAMP+ cells. The expression of DC-STAMP on human PBMC by 1A2 was examined. The expression of DC-STAMP on total PBMC, T cells, and monocytes is shown in FIGS. 16A, 16B and 16C, respectively. To examine DC-STAMP expression on total PBMC, human PBMC were stained with an antibody cocktail composed of 1A2-FITC, CD14-APC, and 7-AAD. After dead cell exclusion by 7-AAD (FIG. 16A(a)), PBMC were gated into monocytes (the P2 and P3 gates in FIG. 16A(b)) and lymphocytes (the P1 gate in FIG. 16A(b)) based on cell size and granularity using forward (FSC) and side scatter (SSC). The corresponding DC-STAMP expression on these distinct cell populations in relation to the monocyte specific marker CD14 are shown in FIG. 16A(c)-(e) and overlaid in FIG. 16A(f). The IgG2a isotype staining control was used to set up the cutoff lines between DC-STAMP+ and DC-STAMP- populations in FIG. 16A(c)-(e). It was clear that the monocyte populations (P2 and P3, FIG. 16A(d & e)) were the majority of DC-STAMP-expressing cells, although some cells gated in the lymphocyte population (P1 in FIG. 16A(b) and (c)) also expressed DC-STAMP (28.5% in FIG. 16A(c)). DC-STAMP was expressed on the surface of the majority of monocytes (FIG. 16A(d)-(e) & 16A(O). A higher mean fluorescence intensity (MFI) observed on monocytes suggested DC-STAMP proteins were expressed at higher levels on monocytes than lymphocytes (FIG. 16A(O).

To overcome the challenges of gating between lymphocytes and monocytes solely by FSC/SSC (FIG. 16A(b)), CD3 and CD19 antibodies were included to more accurately examine DC-STAMP expression on T and B cells. The antibody cocktail was composed of 1A2 (FITC), CD16 (PE), CD14 (APC), CD3 (Pacific Blue), CD19 (APCCy7) and 7-AAD. After FSC/SSC gating and dead cell exclusion (FIG. 16B(a) & (b)), CD14+, CD3+ and CD19+ cells were individually gated and the expression of DC-STAMP on these three populations was analyzed (FIG. 16B(c), CD14+: green; CD3+: blue; CD19+: red). The results were consistent with the data shown in FIG. 16A(f), indicating that monocytes are the major DC-STAMP+ cells. Interestingly, there was a small portion of CD3+ T cells which express DC-STAMP (indicated by arrow in FIG. 16B(c)). The relation between the expression of CD3 and DC-STAMP in human PBMC was examined. As shown in FIG. 16B(d), approximately 12% of total CD3+ T cells are DC-STAMP+ (FIG. 16B(d)). Six fluorescence-minus-one (FMO-FITC, FMOPE, FMO-APC, FMO-Pacific Blue, FMO-APC-Cy7, and FMO-7AAD) staining controls were included in all experiments. DC-STAMP expression was further analyzed on the non-T, non-B cell populations. The 10-color staining panel included antibodies against DC-STAMP, CD14, CD3, CD19, CD11c, CD11b, CD15, CD16, HLA-DR and 7AAD. CD14, CD3 and CD19 were used to identify monocytes, T cells, B cells, and CD11c, CD11b, and HLA-DR were used for monocyte and macrophage classification, respectively. FIG. 16C(a)-(d) depicts the step-by-step gating strategy for gating of the non-T, non-B population. Human PBMC was first gated by FSC/SSC (FIG. 16C(a)), followed by dead cell exclusion using 7-AAD (FIG. 16C(b)), DC-STAMP+ cells (FIG. 16C(c)) were gated, and further dissected by the CD3 and CD19 markers (FIG. 16C(d)). CD19−CD3−(31.9%, FIG. 16C(d), labeled as ∞) and CD19−CD3+ (38.4%, FIG. 16C(d), labeled as *) were two major DC-STAMP+ cell populations. Since the expression of DC-STAMP on CD3+ cells (FIG. 16C(d), labeled by *) was already analyzed and shown by FIG. 16B, here, the analyses focused on the non-T, non-B population (FIG. 16C(d), labeled as ∞). DC-STAMP+CD3−CD19− cells (∞ in FIG. 16C(d)) were further dissected into 4 quadrants based on the expression of CD14 and CD16 (FIG. 16C(c)). The expression of CD11b, CD11c (FIG. 16C(e), i, iii, v, vii) and HLA-DR, CD15 (FIG. 16C(e), ii, iv, vi, viii) on these 4 quadrants was analyzed. The expression intensities of these markers were shown by the Mean Fluorescence Intensity (MFI) (numbers in FIG. 16C(e), i to viii). Notably, both of the DC-STAMP+CD14+CD16+ (FIG. 16C(e), Q2: upper right quadrant) and DC-STAMP+CD14+CD16− (FIG. 16C(e), Q3: lower right quadrant) subsets express very high levels of CD11b and CD11c (FIG. 16C(e), iii and vii), suggesting that CD14+ cells (Q2 and Q3 in FIG. 16C(e)) were more homogenous than the CD16 single positive (Q1 in FIG. 16C(e)) and CD14−CD16− double negative (Q4 in FIG. 16C(e)) populations. There was a higher expression of CD11b and CD11c on the DC-STAMP+CD3−CD19−CD14+ cells (combination of Q2 & Q3 in FIG. 16C(e)), suggesting that these cells have a high potential to be the precursors of osteoclasts (OC), dendritic cells (DC) and macrophages.

Figure 17A:
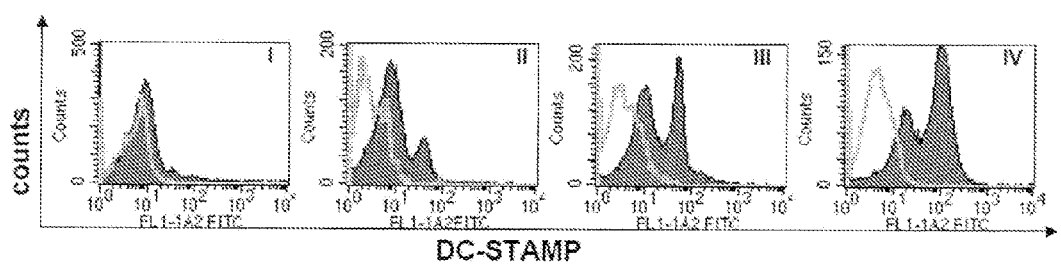
FIG. 17A shows four distinct DC-STAMP expression patterns were observed on human PBMC. PBMC were isolated from a cohort of human subjects (>100) and stained with the 1A2-FITC antibody. Dead cells were excluded by 7-ADD. See Table 3 for the classification criteria of these patterns.

DC-STAMP has the potential to serve as an OCP marker. After examining a cohort of human subjects (>100), four major DC-STAMP expression patterns were identified in human PBMC and designated patterns I to IV (FIG. 17A). Pattern I had the lowest number of DC-STAMP+ cells, whereas pattern IV had the highest number of DC-STAMP+ cells. Table 3 lists the criteria for classification of these patterns based on the ratio of DC-STAMP+ to DC-STAMP-cells. The ratio of DC-STAMP+ to DC-STAMP− was multiplied by 100 and used as the criteria to classify patterns. In short, the number for pattern I was <20, for pattern II was >20 but <67, for pattern III was >68 but <240, and for pattern IV was higher than 240, respectively. To determine whether DC-STAMP could be used as a biomarker of OCP, the correlation between these four DC-STAMP expression patterns and OCP frequency was examined. The pattern of DC-STAMP expression was examined on freshly isolated PBMC by flow cytometry, and OC enumeration was performed on day 8 by TRAP staining. OC culture was established on PBMC isolated from eleven HC and twenty-one PsA subjects. Intriguingly, HC and PsA patients showed an unequal distribution in DC-STAMP patterns (FIG. 17B). Eleven MC subjects demonstrated the DC-STAMP expression pattern I, whereas PsA patients were distributed in all patterns with 4, 6, 5, 6 subjects in pattern I, II, III, IV, respectively (FIG. 17B). The distribution of HC and PsA subjects within these four DC-STAMP patterns was examined by the Fisher's exact analysis. The results indicated that there was a significant difference in the distribution of HC and PsA within these patterns (p=0.011). The average OC numbers derived from DC-STAMP pattern I, II, III, and IV were 50, 98, 105, and 203, respectively (Table 4 and FIG. 17B). These results suggested that there is a correlation between OCP frequency and DC-STAMP patterns, given that OC frequency increased as the DC-STAMP pattern shifted from pattern I toward IV.

TABLE 3

Classification of four major DC-STAMP patterns in human PBMC.

| DC-STAMP Pattern | DC-STAMP+/− ratio* | # of HC subjects | # of PsA subjects |
|---|---|---|---|
| I | 1 to 20 | 11 | 4 |
| II | 20 to 67 | 0 | 6 |
| III | 68 to 240 | 0 | 5 |
| IV | >240 | 0 | 6 |

*The percentage of DC-STAMP+ cells in total human PBMC is divided by that of DC-STAMP− cells

TABLE 4

Statistical analysis of the relation between DC-STAMP expression patterns and OC counts.

| DC-STAMP pattern | OC median | 95% confidence interval of OC median | Inter-quartile range of OC |
|---|---|---|---|
| I | 50 | 15-105 | 17-105 |
| II | 98 | 13-385 | 21-390 |
| III | 105 | 30-131 | 62-131 |
| IV | 203 | 10-491 | 35-340 |

Human monocytes down-regulated DC-STAMP during osteoclastogenesis. It is well established that DC-STAMP is involved in cell fusion of murine monocytes but the variation of surface expression during the course of osteoclastogenesis in human monocytes has not been characterized. The alteration of DC-STAMP cell surface expression on human monocytes cultured in pro-osteoclastogenic media was examined to better understand the temporal sequence of DC-STAMP expression during osteoclastogenesis (FIG. 18A). Enriched human monocytes expressed a high level of surface DC-STAMP (FIG. 18A-*a*). DC-STAMP surface expression was down-regulated after 1 day of exposure to RANKL+M-CSF (FIG. 18A-*b*), and continued to decline after day 2 (FIG. 18A, c-e). Notably, DC-STAMP surface expression decreased dramatically after day 6 and became undetectable after day 7 (FIG. 18A-*e*), a time point when mature OC were visualized by TRAP staining.

Next, the cellular localization of DC-STAMP on OC was examined. In contrast to several studies in which DC-STAMP localization on DC was performed on cells transfected with a DC-STAMP-GFP fusion protein (Sawtani et al., Int. Immunol. 20:1259-68 (2008); Eleveld-Trancikova et al., J. Leukoc. Biol. 77:337-43 (2005); Jansen et al., 46:505-15 (2009)), the newly established anti-DC-STAMP mAb 1A2 was used to localize endogenous DC-STAMP. This approach is a more reliable method to track protein localization than GFP-tagging (Lisenbee et al., Traffic 4:491-501 (2003)). After 8 days of culture with RANKL+M-CSF, the majority of monocytes was unable to differentiate into OC and manifested a spindle-shaped morphology (FIG. 18B(a)), indicative of a pre-osteoclast differentiation stage. DC-STAMP protein localized intracellularly with a punctuate distribution in these cells (FIG. 18B(a)). In contrast, DC-STAMP protein could not be identified in multinucleated OC from the same cultures (FIG. 18B(b)). These polykaryons that lacked DC-STAMP protein displayed prominent actin rings, a structure associated with bone-resorbing capacity of OC. Taken together, the FACS (FIG. 18A) and confocal staining data (FIG. 18B) suggest that DC-STAMP is down-regulated when monocytes differentiate into OC.

Figure 19A:
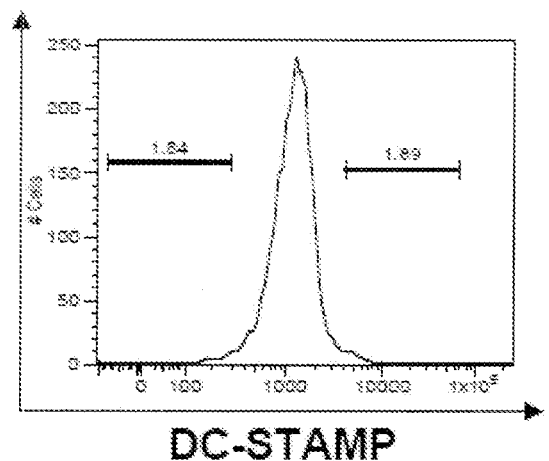
FIG. 19A shows a gating strategy of human monocytes based on the DC-STAMP expression. Human monocytes were enriched by negative selection, stained with 1A2-FITC and sorted into DC-STAMP$^{high}$ and DC-STAMP$^{low}$ (1.9% and 1.8% of the highest and lowest).

DC-STAMP$^{high}$ monocytes generate more osteoclasts than DC-STAMP$^{low}$ monocytes. To determine whether the level of DC-STAMP surface expression on monocytes correlates with the ability of these cells to undergo osteoclastogenesis, enriched, freshly-isolated human monocytes were stained (>85% purity) with the 1A2 DC-STAMP mAb and the cells were sorted into two populations, DC-STAMP$^{high}$ and DC-STAMP$^{low}$ (FIG. 19A, 1.9% highest and 1.8% lowest of total sorted monocytes, respectively). The bone resorption activities of these 2 populations were evaluated after cells were cultured for 8 days with RANKL and M-CSF.

Figure 19B:
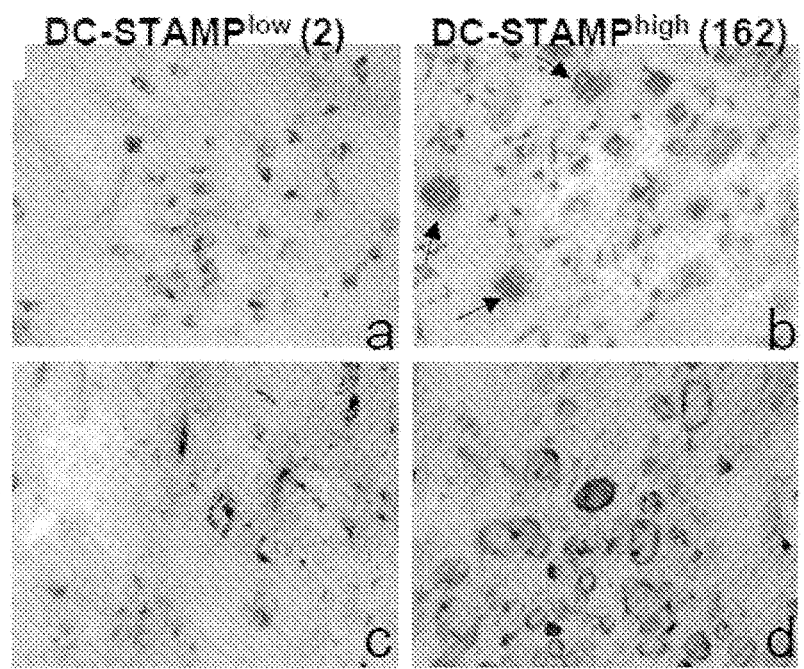
FIG. 19B shows images of the bone resorption activity of DC-STAMP$^{high}$ and DC-STAMP$^{low}$ cells. Sorted DC-STAMP$^{high}$ and DC-STAMP$^{low}$ cells shown in (A) were cultured with bone wafers for 14 days in the presence of RANKL and M-CSF. Numbers in parentheses represent the total number of TRAP+ OC per $10^5$ sorted cells. OC and erosion pits on bone wafers by DC-STAMP$^{low}$ and DC-STAMP$^{high}$ cells were shown in (a & b) and (c & d), respectively. Representative of three individual experiments performed on HC.

As shown in FIG. 19B, more TRAP+ mature OC were generated from freshly-isolated DC-STAMP$^{high}$ (162 per $10^5$) compared to DC-STAMP$^{low}$ (2 per $10^5$) cells. In addition, the bone resorption activities of these two cell populations was examined with the bone wafer assay (FIG. 19B(c) & (d)). More than 90% of bone surface was eroded deeply by OC derived from freshly-isolated DC-STAMP$^{high}$ human monocytes (FIG. 19B(d)), whereas cells derived from freshly-isolated DC-STAMP$^{low}$ human monocytes produced few, comparatively shallow erosion pits (<10%, FIG. 19B (c)). Taken together, the results suggest a positive association between DC-STAMP expression, osteoclastogenic potential and bone resorption activity in human monocytes.

Figure 20A:
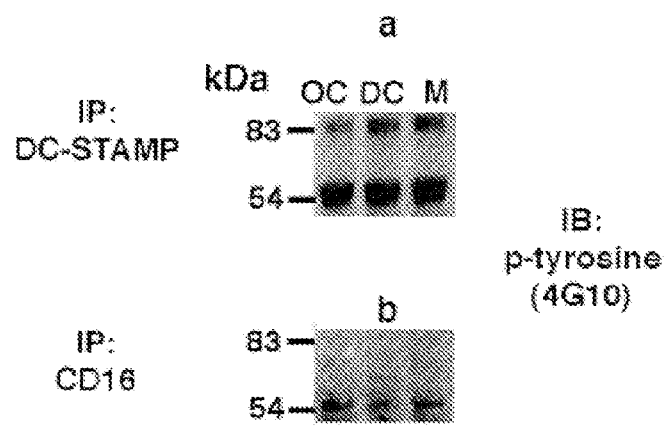
FIG. 20A were cellular lysates of OC, DC and monocytes (M) were subjected to immunoprecipitation (IP) with DC-STAMP mAb 1A2 (a) or CD16 mAb (b). The immunoprecipitates were separated by SDS-PAGE and immunoblotted (IB) with anti-phosphotyrosine mAb 4G10.
Figure 20B:
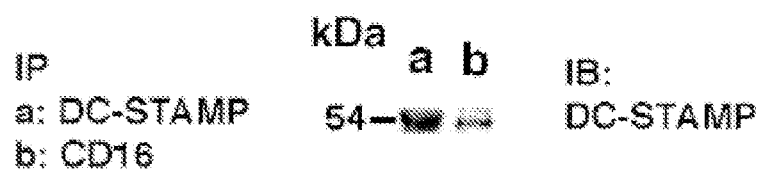
FIG. 20B shows cellular lysates of monocytes subjected to IP with DC-STAMP (a) or CD16 (b) mAbs, and IB with DC-STAMP mAb 1A2.

DC-STAMP is phosphorylated on its tyrosine residues and interacts with SHP-1. With the knowledge that DC-STAMP contains an ITIM motif, DC-STAMP phosphorylation at the protein level was further examined. The presence of one tyrosine residue ($^{407}$Ser-Phe-Tyr-Pro-Ser-Val$^{412}$) (SEQ ID NO:4) in the ITIM of DC-STAMP, suggested a possible phosphorylation site. Thus, the tyrosine phosphorylation profiles of DC-STAMP were examined by western blot analysis in monocytes that were cultured in the presence of M-CSF and RANKL or IL-4 and GM-CSF (FIG. 20A). Since the molecular weights (M.W.) of DC-STAMP and heavy chain (50 kDa) are very close, the light-chain-specific $2^{nd}$ antibody was used to avoid background from heavy chain on the western blots. Cellular lysates of OC, DC and monocytes were subjected to immunoprecipitation with DC-STAMP mAb 1A2. Immunoprecipitates were separated by SDS-PAGE and then immunoblotted with antiphosphotyrosine 4G10 (FIG. 20A(a)). One predominant 54 kDa band corresponding to the M.W. of DC-STAMP was detected in all 3 cell lineages. Besides this band, there was an extra band (~83 kDa) that may be an isoform of DC-STAMP with post-translational modification such as glycosylation. Next, cell lysates of OC were immunoprecipitated with either anti-DC-STAMP or anti-CD16 mAb, and the blot was probed with anti-DC-STAMP 1A2. As shown in FIG. 24B, the CD16 mAb was able to pull down DC-STAMP, indicative of a physical interaction between CD16 and DC-STAMP. Less DC-STAMP proteins were immunoprecipitated by the CD16 mAb than the DC-STAMP mAb (compare FIG. 20B(a) to (b)).

Figure 20C:
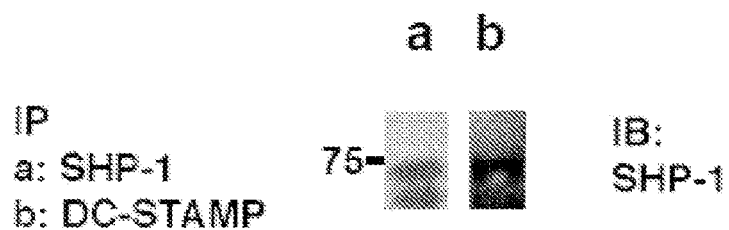
FIG. 20C shows cellular lysates of monocytes were subjected to IP with anti-DC-STAMP 1A2, and IB with anti-SHP-1 mAb.

Next, the same cell lysates were immunoprecipitated from OC, DC and monocytes with the CD16 mAb and then immunoblotted with anti-phosphotyrosine 4G10 (FIG. 20A(b)). In contrast to the cell lysates of OC and monocytes (FIG. 24A (b), $1^{st}$ and $3^{rd}$ lanes) with one single 54 kDa band corresponding to the DC-STAMP protein, the intensity of 54 kDa band in DC lysates was attenuated. Instead, there was an additional larger band (~70 kDa) in DC lysates which was not observed in OC or monocytes. The amount of DC-STAMP phosphorylation co-immunoprecipitated with CD16 was comparable between OC and monocytes (FIG. 20A(b), $1^{st}$ and $3^{rd}$ lanes). The data suggested that DC-STAMP demonstrated a lesser degree of phosphorylation in DC. LILRB and PIR-B, the other two ITIM-bearing immunoglobulin-like receptors, are known to recruit the phosphatase SHP-1 and suppress OC development in vitro. These are common features for Ig-like receptors with inhibitory functions. Thus, whether DC-STAMP, similar to their ITIM-bearing molecules, also signals via an interaction with SHP-1 as observed in LILRB and PIR-B was examined. Cell lysates were first immunoprecipitated by anti-DC-STAMP mAb 1A2 and immunoblotted with anti-SHP-1 mAb. One single 70 kDa band corresponding to SHP-1 was found in these immunoprecipitates (FIG. 20C), suggesting an interaction between DC-STAMP and SHP-1. Interestingly, two (~70 kDa and ~68 kDa) bands were present in the positive control (FIG. 20C(a), IP with SHP-1 and IB with SHP-1).

Example 3

Pharmokinetic characterization of DC-STAMP mAb 1A2. In order to determine the pharmokinetic properties of the DC-STAMP mAb 1A2, a single subcutaneous administration of 30 mg/kg was given to BALB/c mice. Four mice were dosed with the 1A2 mAb and serial blood samples were collected from the tail vein at 1, 4, 7, 24, 48, 72, 103, and 168 hours. The mean maximal concentration ($C_{max}$) was determined to be 305 mg/ml, which would be expected after a 30 mg/kg dose. The time taken to achieve the $C_{max}$ ($T_{max}$) was relatively short indicating that absorption of this antibody after subcutaneous dosing was not a problem. Mouse 1 was terminated after 72 hours due to weight loss, so PK analysis was not carried out on mouse 1. A summary of the results is shown in Tables 5 and 6 below.

TABLE 5

Subcutaneous serum pharmacokinetics of 1A2.

| Mouse ID | Mouse 2 | Mouse 3 | Mouse 4 | Mean | SE |
|---|---|---|---|---|---|
| $C_{max}$ (µg/ml) | 341 | 256 | 317 | 305 | 25 |
| $T_{max}$ (h) | 48 | 24 | 24 | 32 | 8 |
| AUC$_{(last)}$ (hr · mg/ml) | 44542 | 33562 | 39977 | 40027 | 2593 |
| AUC$_{(inf)}$ (hr · mg/ml) | 122893 | 96428 | 128894 | 116072 | 9973 |
| % Extrapolation | 63.8 | 63.1 | 69 | 65.3 | 1.9 |
| CL/F$_{sc}$ (ml/hr/kg) | 0.24 | 0.31 | 0.23 | 0.26 | 0.02 |
| MRT$_{inf}$ (h) | 350 | 366 | 425 | 380 | 23 |
| T$_{1/2}$ (h) | 231.9 | 253.4 | 285.9 | 257 | 15.7 |

$C_{max}$: concentration maximum; $T_{max}$: Time to reach maximum concentration; AUC$_{(last)}$: area under concentration curve to the last validated measurement; AUC$_{(inf)}$: area under concentration curve to infinity; CL/F$_{sc}$: systemic clearance; MRT$_{inf}$: mean residence time at infinity; T$_{1/2}$: half-life; h: hour; hr · mg/ml: hour · milligram per milliliter; ml/hr/kg: milliliter per hour per kilogram.

TABLE 6

Serum data

| | Concentration (µg/ml) | | | | | |
|---|---|---|---|---|---|---|
| Time (h) | Mouse 1 | Mouse 2 | Mouse 3 | Mouse 4 | Mean | SD |
| 1 | 26.4 | 33.3 | 38.1 | 33.1 | 32.7 | 4.8 |
| 4 | 154.3 | 209.7 | 217.4 | 178.3 | 189.9 | 29.1 |
| 7 | 218.9 | 224.1 | 238.6 | 232.9 | 228.6 | 8.8 |
| 24 | 273.8 | 299.5 | 255.6 | 317.4 | 286.6 | 27.3 |
| 48 | N/S | 341.1 | 242.6 | 295.8 | 293.2 | 49.3 |
| 72 | 231.5 | 292.1 | 233.7 | 247.3 | 251.1 | 28.2 |
| 103 | N/S | 242.4 | 198.9 | 200.7 | 214.0 | 24.6 |
| 168 | N/S | 234.2 | 166.5 | 215.6 | 205.4 | 35.0 |

N/S: no sample

What is claimed is:

1. A monoclonal antibody that specifically binds to an epitope of DC-STAMP, wherein the epitope comprises the amino acid sequence Glu-Val-His-Leu-Lys-Leu-His-Gly-Glu-Lys-Gln-Gly-Thr-Gln (SEQ ID NO:1).

2. The monoclonal antibody that specifically binds to an epitope of DC-STAMP, wherein the epitope consists of amino acid sequence His-Gly-Glu-Lys-Gln-Gly-Thr-Gln (SEQ ID NO:2).

3. The monoclonal antibody of claim 1, wherein a light chain of the monoclonal antibody comprises SEQ ID NO:5.

4. The monoclonal antibody of claim 1, wherein a heavy chain of the monoclonal antibody comprises SEQ ID NO:6.

5. A composition comprising a monoclonal antibody, wherein the composition comprises monoclonal antibody that specifically binds to an epitope of DC-STAMP, wherein the epitope consists of SEQ ID NO:1.

6. The composition of claim 5, wherein the antibody comprises a light chain comprising SEQ ID NO:5.

7. The composition of claim 5, wherein the antibody comprises a heavy chain comprising SEQ ID NO:6.

8. The composition of claim 5, wherein the composition further comprises a pharmaceutically acceptable carrier.

9. A method of inhibiting osteoclastogenesis in a DC-STAMP expressing osteoclast precursor cell, the method comprising administering to the cell the composition of claim 5.

10. The method of claim 9, wherein the composition is administered in vitro.

11. The method of claim 9, wherein the cell is a mammalian cell.

12. The method of claim 11, wherein the mammalian cell is a human cell.

13. The method of claim 9, wherein the composition is administered to a subject in vivo.

14. The method of claim 13, wherein the composition further comprises a pharmaceutically acceptable carrier.

15. A monoclonal antibody that specifically binds to an epitope of DC-STAMP, wherein a heavy chain of the antibody comprises SEQ ID NO: 6 or all complementarity determining regions (CDRs) thereof and a light chain of the antibody comprises SEQ ID NO: 5 or all CDRs thereof.

* * * * *

UNITED STATES PATENT AND TRADEMARK OFFICE
CERTIFICATE OF CORRECTION

PATENT NO. : 9,018,358 B2  
APPLICATION NO. : 13/266629  
DATED : April 28, 2015  
INVENTOR(S) : Edward M. Schwarz et al.

Page 1 of 1

It is certified that error appears in the above-identified patent and that said Letters Patent is hereby corrected as shown below:

Claims

At Column 45, Line 21, Claim 1:

Please cancel the text "comprises" and replace with --consists of--.

Signed and Sealed this
Twenty-third Day of February, 2016

Michelle K. Lee
*Director of the United States Patent and Trademark Office*